(12) United States Patent
Copeland et al.

(10) Patent No.: US 11,857,138 B2
(45) Date of Patent: Jan. 2, 2024

(54) SURFACE CLEANING DEVICE WITH ODOR MANAGEMENT

(71) Applicant: SHARKNINJA OPERATING LLC, Needham, MA (US)

(72) Inventors: Ryan M. Copeland, Watertown, MA (US); Samuel J. Levine, Needham, MA (US); Justin G. Riley, Needham, MA (US); Daniel R. Der Marderosian, Westwood, MA (US); Qiang Liu, Suzhou (CN); Peng Fei Liu, Needham, MA (US); Kui Liu, Suzhou (CN); Bo Gao, Needham, MA (US); Jiancheng Wang, Suzhou (CN); Jeremy McDaniel, Boston, MA (US)

(73) Assignee: SharkNinja Operating LLC, Needham, MA (US)

( * ) Notice: Subject to any disclaimer, the term of this patent is extended or adjusted under 35 U.S.C. 154(b) by 0 days.

(21) Appl. No.: 17/846,829

(22) Filed: Jun. 22, 2022

(65) Prior Publication Data
US 2023/0038659 A1 Feb. 9, 2023

Related U.S. Application Data

(63) Continuation of application No. 17/843,692, filed on Jun. 17, 2022.
(Continued)

(51) Int. Cl.
*A47L 7/00* (2006.01)
*A47L 5/30* (2006.01)
(Continued)

(52) U.S. Cl.
CPC ............ *A47L 7/0061* (2013.01); *A47L 5/30* (2013.01); *A47L 7/04* (2013.01); *A47L 9/0411* (2013.01);
(Continued)

(58) Field of Classification Search
CPC .. A47L 7/0061; A47L 5/30; A47L 7/04; A47L 9/0411; A47L 9/0477; A61L 9/042;
(Continued)

(56) References Cited

U.S. PATENT DOCUMENTS

| 1,446,456 A | 2/1923 | Frazee, Jr. |
|---|---|---|
| 2,070,643 A | 2/1937 | Becker |

(Continued)

FOREIGN PATENT DOCUMENTS

| CA | 2467286 | 9/2008 |
|---|---|---|
| CN | 2801057 | 8/2006 |

(Continued)

OTHER PUBLICATIONS

Chinese Office Action with English language Summary, dated Feb. 7, 2023, received in Chinese Patent Application No. 202222938452.7, 4 pages.
(Continued)

*Primary Examiner* — David Redding
(74) *Attorney, Agent, or Firm* — Grossman Tucker Perreault & Pfleger, PLLC

(57) ABSTRACT

A surface cleaning device includes a nozzle and an odor dial assembly. The nozzle includes a nozzle housing and a dirty air passageway. The odor dial assembly include a fragrance member and a dial body configured to be removably coupled to the nozzle housing. The dial body at least partially defines a fragrance cavity configured to at least partially receive the fragrance member and a fragrance passageway extending therethrough. The odor dial assembly is configured to transition between a plurality of user-selectable positions to adjust an amount of fragrance particles released by the fragrance member into the dirty air passageway.

22 Claims, 44 Drawing Sheets

Related U.S. Application Data

(60) Provisional application No. 63/228,905, filed on Aug. 3, 2021.

(51) Int. Cl.
    *A61L 9/12*     (2006.01)
    *A61L 9/04*     (2006.01)
    *A47L 7/04*     (2006.01)
    *A47L 9/04*     (2006.01)

(52) U.S. Cl.
    CPC ............ *A47L 9/0477* (2013.01); *A61L 9/042* (2013.01); *A61L 9/12* (2013.01)

(58) Field of Classification Search
    CPC .. A61L 9/12; A61L 2209/13; A61L 2209/133; A61L 9/127; A61L 9/015; A61L 9/04
    See application file for complete search history.

(56) References Cited

U.S. PATENT DOCUMENTS

| | | | |
|---|---|---|---|
| 4,154,398 A | 5/1979 | Gualandi | |
| 4,545,917 A | 10/1985 | Smith et al. | |
| 4,554,698 A | 11/1985 | Rennecker et al. | |
| D381,477 S | 7/1997 | Ingram | |
| 5,766,547 A | 6/1998 | Kay et al. | |
| 5,922,093 A | 7/1999 | James et al. | |
| 5,946,770 A | 9/1999 | Bijma et al. | |
| 6,090,184 A | 7/2000 | Cartellone | |
| 6,156,088 A | 12/2000 | Cardarelli | |
| 6,156,099 A | 12/2000 | Hironaka et al. | |
| 6,171,375 B1* | 1/2001 | Howie | B01D 46/50 96/57 |
| 6,174,350 B1 | 1/2001 | Rohn et al. | |
| 6,295,695 B1 | 10/2001 | Park | |
| 6,459,955 B1 | 10/2002 | Bartsch et al. | |
| 6,499,183 B1 | 12/2002 | Paterson et al. | |
| 6,511,548 B1* | 1/2003 | Oreck | A47L 9/00 422/5 |
| 6,589,323 B1 | 7/2003 | Korin | |
| 6,802,460 B2 | 10/2004 | Hess et al. | |
| 6,941,199 B1 | 9/2005 | Bottomley et al. | |
| 7,093,773 B2* | 8/2006 | Kuiper | A61L 9/04 239/289 |
| 7,108,731 B2 | 9/2006 | Park et al. | |
| 7,305,735 B2 | 12/2007 | Overvaag | |
| 7,507,272 B2 | 3/2009 | Emig et al. | |
| 7,528,102 B2 | 5/2009 | Barthel et al. | |
| 7,628,846 B2 | 12/2009 | Oh et al. | |
| 7,765,636 B2 | 8/2010 | Hirota et al. | |
| 7,774,897 B2* | 8/2010 | Oh | A47L 7/04 15/327.2 |
| 7,837,772 B2 | 11/2010 | Sepke | |
| 7,837,958 B2 | 11/2010 | Crapser et al. | |
| 8,211,208 B2 | 7/2012 | Chan et al. | |
| 8,857,735 B2 | 10/2014 | Rosener et al. | |
| 8,881,999 B2 | 11/2014 | Blaylock et al. | |
| 8,984,705 B2* | 3/2015 | Bosses | A47L 9/00 422/123 |
| 8,991,003 B2 | 3/2015 | Krebs | |
| 9,033,316 B2 | 5/2015 | Hansen et al. | |
| 9,433,691 B2 | 9/2016 | Eide et al. | |
| 9,585,536 B2 | 3/2017 | Pi et al. | |
| 9,649,004 B2* | 5/2017 | Houghton | A47L 11/4086 |
| 9,675,220 B2 | 6/2017 | Kah, Jr. | |
| 9,717,815 B2 | 8/2017 | Peterson et al. | |
| 9,782,049 B2 | 10/2017 | York et al. | |
| 9,801,970 B2 | 10/2017 | Chase et al. | |
| 9,820,627 B2 | 11/2017 | Caro, Jr. et al. | |
| 9,889,220 B1 | 2/2018 | Yip et al. | |
| 10,238,253 B2* | 3/2019 | Morrow | A61L 9/012 |
| 10,391,191 B2 | 8/2019 | Cutler et al. | |
| 10,398,280 B2* | 9/2019 | Krebs | A47L 11/4086 |
| 10,549,005 B2 | 2/2020 | Davis et al. | |
| 10,610,612 B2 | 4/2020 | Jakins et al. | |
| 10,806,815 B2 | 10/2020 | Hackert | |
| 10,827,892 B2 | 11/2020 | Krebs et al. | |
| 2005/0015914 A1 | 1/2005 | You et al. | |
| 2005/0022331 A1 | 2/2005 | Kim et al. | |
| 2005/0191217 A1 | 9/2005 | Selander | |
| 2005/0194460 A1 | 9/2005 | Selander | |
| 2006/0090290 A1 | 5/2006 | Lau | |
| 2006/0225242 A1 | 10/2006 | Oh et al. | |
| 2007/0022560 A1 | 2/2007 | Corwin et al. | |
| 2007/0209144 A1 | 9/2007 | Fester et al. | |
| 2008/0148512 A1 | 6/2008 | Beskow et al. | |
| 2010/0116935 A1 | 5/2010 | Rieger et al. | |
| 2010/0175559 A1 | 7/2010 | Sepke | |
| 2011/0146720 A1 | 6/2011 | Huffman | |
| 2012/0304412 A1 | 12/2012 | Lynch et al. | |
| 2013/0323193 A1 | 12/2013 | Kawano et al. | |
| 2014/0377130 A1 | 12/2014 | Edwards et al. | |
| 2016/0302631 A1 | 10/2016 | Guerra et al. | |
| 2018/0333736 A1 | 11/2018 | Krebs | |
| 2019/0117030 A1 | 4/2019 | Kette | |
| 2019/0133391 A1 | 5/2019 | Khazaieli et al. | |
| 2020/0331326 A1 | 10/2020 | Bourne | |

FOREIGN PATENT DOCUMENTS

| | | | |
|---|---|---|---|
| CN | 101703383 | | 5/2010 |
| CN | 209236011 | | 8/2019 |
| CN | 209270405 | | 8/2019 |
| CN | 209316598 | | 8/2019 |
| CN | 111971077 | | 11/2020 |
| DE | 8028824 | | 3/1981 |
| DE | 29712553 | | 9/1997 |
| DE | 102007060847 | | 9/2013 |
| DE | 102015118653 | | 5/2017 |
| DE | 202017103530 | | 9/2017 |
| DE | 202018004401 | | 1/2019 |
| DE | 202020102190 | | 6/2020 |
| EP | 1201173 | | 8/2004 |
| EP | 1482825 | | 6/2006 |
| EP | 3682910 | * | 7/2020 |
| FR | 2833531 | | 6/2003 |
| GB | 2422777 | | 8/2006 |
| GB | 2407967 | | 4/2007 |
| JP | H10151097 | | 6/1998 |
| JP | 2004113469 | | 4/2004 |
| JP | 2008036151 | | 2/2008 |
| JP | 2013000480 | | 1/2013 |
| KR | 1020140111819 | | 9/2014 |
| WO | 2006108320 | | 10/2006 |

OTHER PUBLICATIONS

PCT Search Report and Written Opinion dated Feb. 14, 2023, received in PCT Application No. PCT/US22/48954, 12 pages.
PCT Search Report and Written Opinion dated May 30, 2023, received in PCT Application No. PCT/US23/14632, 8 pages.
Operating Manual of Gtech 5254 AirRAM Platinum; Grey Technology Limited, Retrieved Jul. 3, 2022, 20 pages.
AirRam Platinum, Anti Hair Wrap Cordless Vacuum, Gtech, 2022, https://www.gtech.co.uk/cordless-vacuum-cleaners/uprights/airram-platinum.html.

* cited by examiner

SURFACE CLEANING DEVICE WITH ODOR MANAGEMENT

CROSS REFERENCE TO RELATED APPLICATIONS

The present application is a continuation application of application Ser. No. 17/843,692, filed Jun. 17, 2022, which claims the benefit of U.S. Provisional Application Ser. No. 63/228,905 filed on Aug. 3, 2021, entitled SURFACE CLEANING DEVICE WITH ODOR MANAGEMENT, all of which are fully incorporated herein by reference.

TECHNICAL FIELD

This specification generally relates to surface cleaning devices, and more particularly to odor management during operation of a surface cleaning device.

BACKGROUND INFORMATION

The following is not an admission that anything discussed below is part of the prior art or part of the common general knowledge of a person skilled in the art.

Powered surface cleaning devices, such as vacuum cleaners, have multiple components that each receive electrical power from one or more power sources (e.g., one or more batteries or electrical mains). For example, a vacuum cleaner may include a suction motor to generate a vacuum within a cleaning head. The generated vacuum collects debris from a surface to be cleaned and deposits the debris, for example, in a debris collector. The vacuum may also include a motor to rotate a brush roll within the cleaning head. The rotation of the brush roll agitates debris that has adhered to the surface to be cleaned such that the generated vacuum is capable of removing the debris from the surface. In addition to electrical components for cleaning, the vacuum cleaner may include one or more light sources to illuminate an area to be cleaned.

BRIEF DESCRIPTION OF THE DRAWINGS

These and other features advantages will be better understood by reading the following detailed description, taken together with the drawings wherein:

The drawings included herewith are for illustrating various examples of articles, methods, and apparatuses of the teaching of the present specification and are not intended to limit the scope of what is taught in any way.

FIG. 1I shows another enlarged section of the surface cleaning device shown in FIG. 1F.

FIGS. 7A, 7B, and 7C 6 show various positions of the odor dial assembly.

DETAILED DESCRIPTION

The present disclosure is generally directed to an odor control assembly for use in a surface cleaning device. The odor control assembly may include an adjustment member that can be transitioned between a plurality of user-selectable positions to vary an amount of fragrance particles output by the odor control assembly during use of the surface cleaning device.

In more detail, the fragrance particles may be provided by a fragrance member that is coupled to the adjustment member, with the fragrance member providing at least one fragrance air path. The adjustment member can adjust the width of the opening to the fragrance air path based on the plurality of user-selectable positions. The air traveling through the fragrance air path may then cause fragrance particles to become airborne. The odor control assembly may then output the airborne fragrance particles, which may also be referred to herein as simply fragrance particles. The odor control assembly may output the airborne fragrance particles to a dirty air passageway defined by the nozzle of the surface cleaning device. The air communicated through the fragrance air path of the fragrance member can be provided from a motor, for example. The temperature of the air communicated across the motor, and/or the velocity of the air communicated across the motor, may be advantageously utilized to ensure that a predetermined amount of fragrance particles get output by the odor control assembly. In one example, the predetermined amount of fragrance particles is at least 4 milligrams per hour (mg/h).

The adjustment member may be removably coupled to the odor control assembly. The adjustment member and fragrance member can decouple together as a single unit. The fragrance member may be removable from the adjustment member for replacement purposes.

Figure 1A:
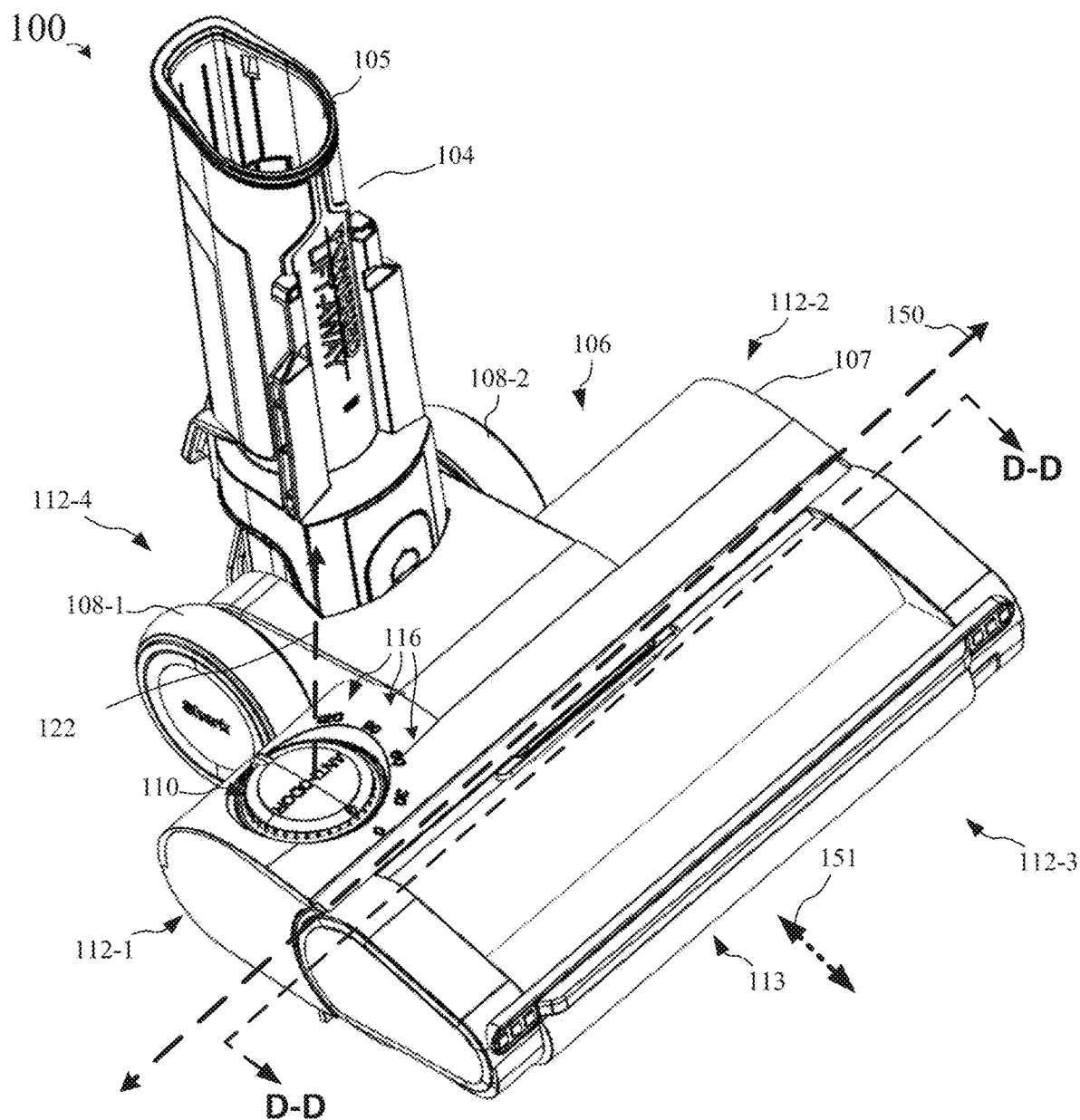
FIG. 1A shows an example surface cleaning device consistent with aspects of the present disclosure.

FIG. 1A shows a surface cleaning device 100 consistent with aspects of the present disclosure. As shown, the surface cleaning device 100 includes an upright section 104 coupled to a nozzle 106. The upright section 104 may pivotally couple to the nozzle 106. The upright section 104 may also include a receptacle 105 to receive and couple to a handle portion (not shown). The handle portion coupled to the receptacle 105 can include a suction motor (also referred to herein as first motor) and a dust cup, though this is not a limitation of the present disclosure unless specifically claimed as such. The suction motor may be configured to generate suction. The suction motor can fluidly couple to a dirty air passageway of the nozzle 106 to draw dirty air into the dust cup.

The surface cleaning device 100 may further include first and second wheels 108-1, 108-2 coupled to the nozzle 106. The first and second wheels 108-1, 108-2 may be coupled on opposite sides of the nozzle 106. For example, the first and second wheels 108-1, 108-2 may be coupled adjacent a pivot joint that rotatably couples the upright section 104 and the nozzle 106 together. The first and second wheels 108-1, 108-2 may be unpowered or driven by a motor as discussed in further detail below.

The nozzle 106 may include a nozzle housing 107. The nozzle housing 107 may extend from a first lateral end 112-1 to a second lateral end 112-2 (e.g., left and right) along a longitudinal axis 150 and/or from a front end 112-3 and rear end 112-4. The longitudinal axis 150 of the nozzle housing 107 may extend transverse relative to primary direction of travel 151 during cleaning operations.

Figure 1B:
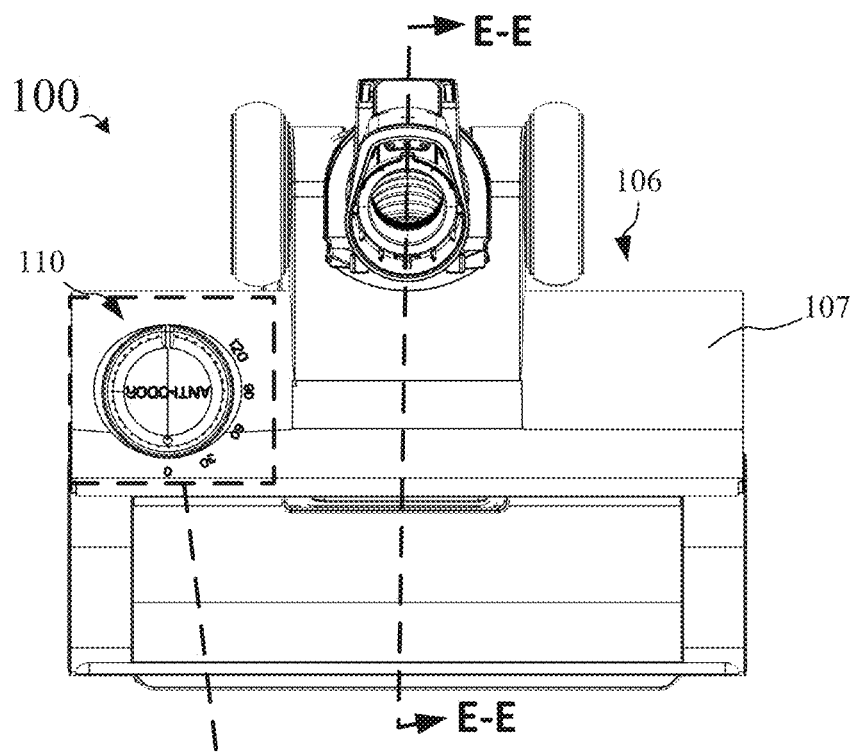
FIG. 1B shows a top view of the surface cleaning device of FIG. 1A, in accordance with aspects of the present disclosure.
Figure 1C:
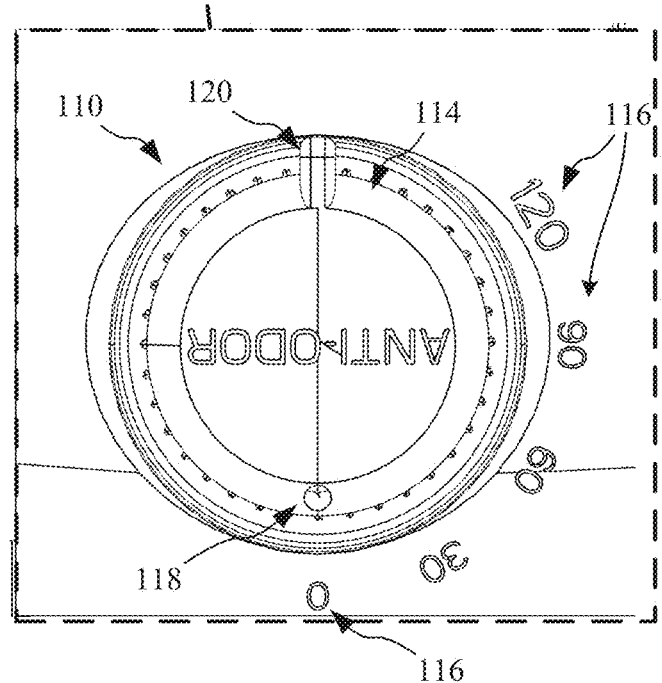
FIG. 1C shows an enlarged section of the surface cleaning device of FIG. 1B.
Figure 1D:
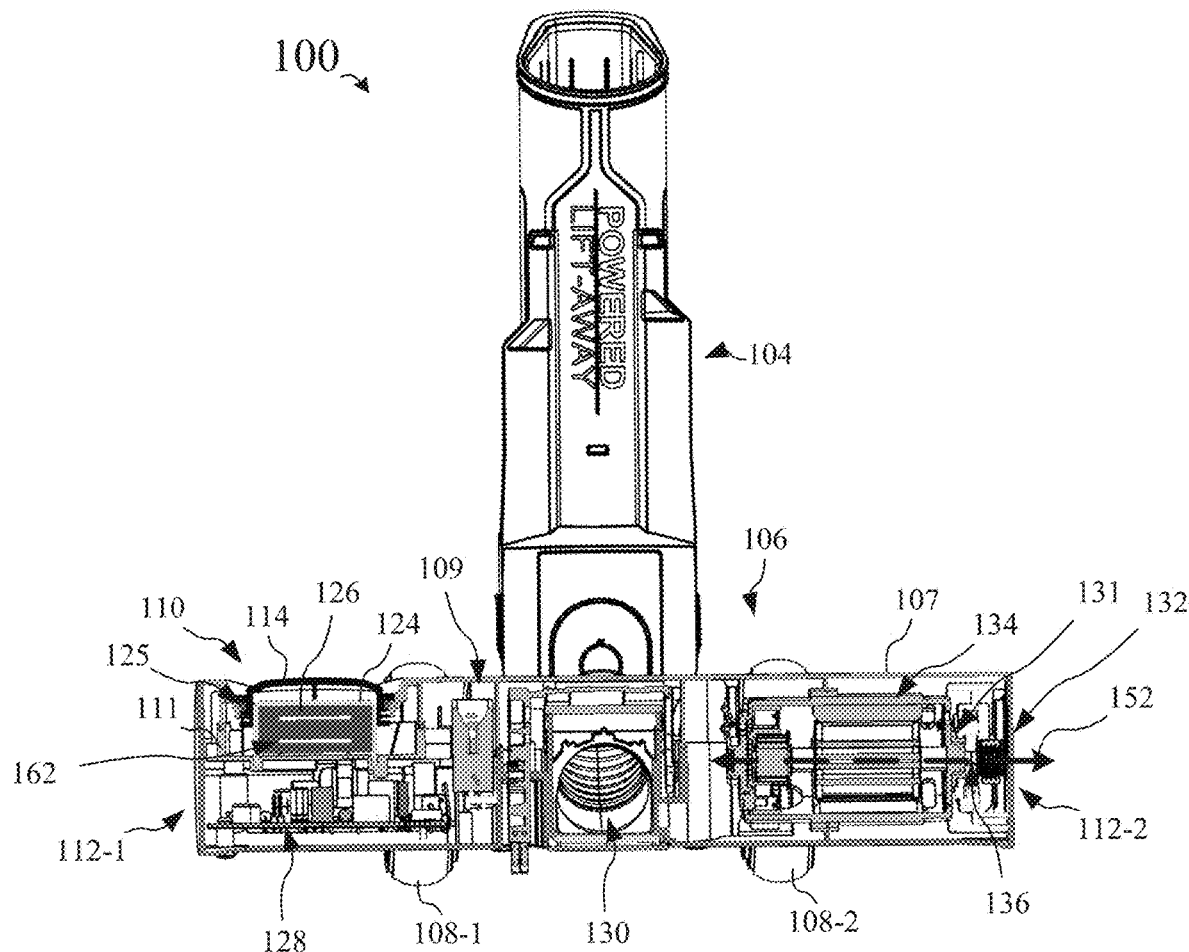
FIG. 1D shows a cross-sectional view of the surface cleaning device of FIG. 1A taken along line D-D.
Figure 1E:
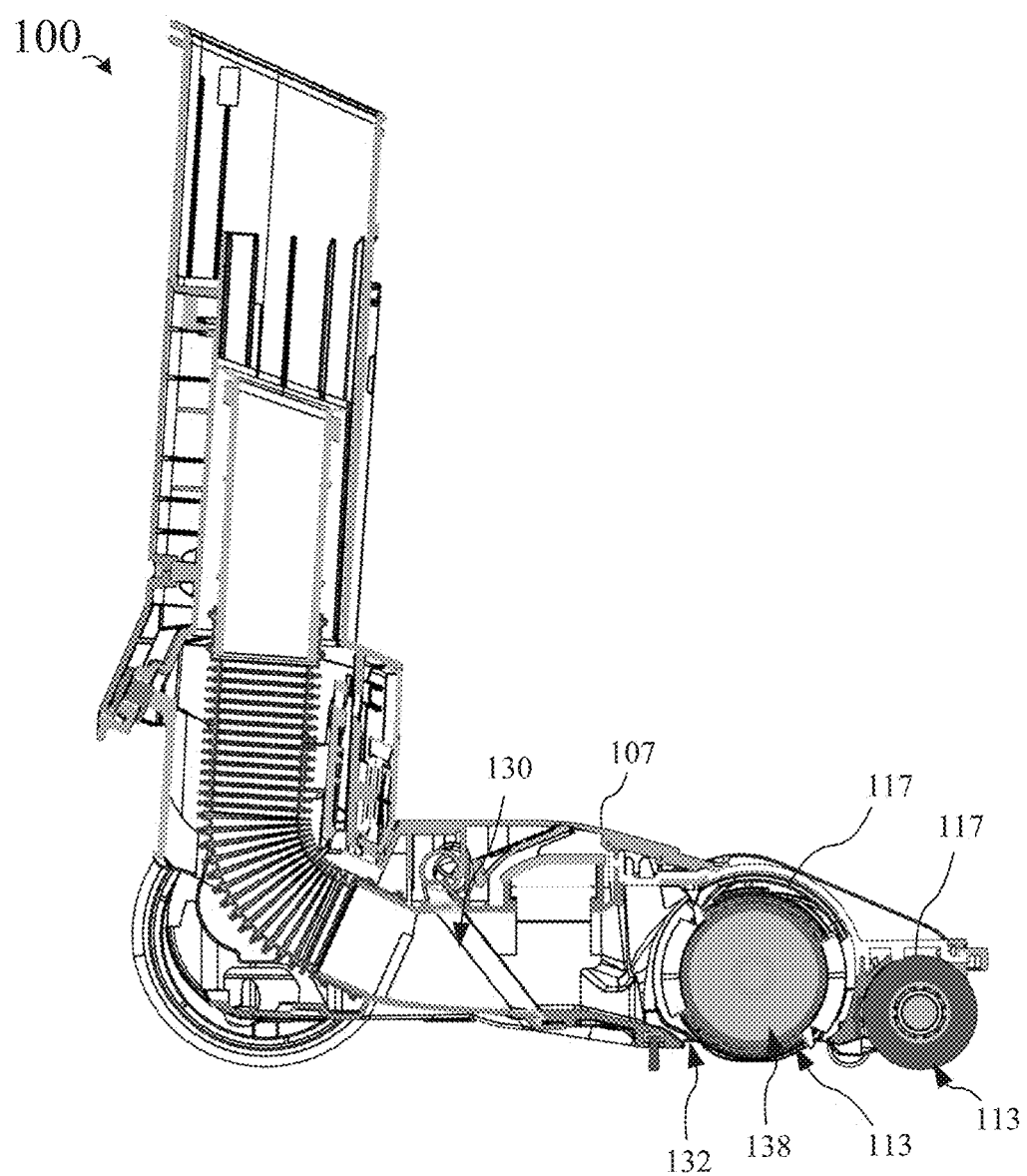
FIG. 1E shows a cross-sectional view of the surface cleaning device of FIG. 1B taken along line E-E.

The nozzle housing 107 may define a nozzle cavity 109 (See FIG. 1F) and/or one or more agitator chambers 117 (See FIG. 1E). The nozzle cavity 109 can include a plurality of components disposed therein and the agitator chambers 117 may include one or more rotating agitators/brush roll 113.

The surface cleaning device 100 may further include an odor control assembly 110. The odor control assembly 110 may be coupled to the nozzle housing 107. For example, the odor control assembly 110 may be at least partially disposed in the nozzle housing 107, and more particularly, in the nozzle cavity 109 of the nozzle housing 107.

As shown more clearly in FIGS. 1B-1C, the odor control assembly 110 includes an adjustment member 114. The adjustment member 114 may be configured to allow for a user to adjust an amount of fragrance particles introduced into a dirty air passageway of the nozzle 106, as discussed in greater detail below. Alternatively, or in addition, the adjustment member 114 may be used to adjust an amount of fragrance particles introduced into the environment surrounding the surface cleaning device 100 (e.g., without the fragrance particles necessarily passing through the dirty air passageway). The adjustment member 114 may be configured to be transitioned between a plurality of user-selectable positions to adjust an amount of fragrance particles released into the dirty air passageway and/or the surrounding environment. The adjustment member 114 may also be referred to as a fragrance dial, or simply a dial.

The adjustment member 114 may be configured to be displaced by a user-supplied force to transition the adjustment member 114 between the plurality of user-selected positions. The plurality of user-selectable positions can include at least a first open position to release a first predetermined amount of fragrance from the fragrance member into the dirty air passageway, and a closed position to substantially prevent and/or minimize the amount of fragrance being released into the dirty air passageway of the surface cleaning device 100. The plurality of user-selectable positions can further include a second open position to release a second predetermined amount of fragrance form the fragrance member into the dirty air passageway of the surface cleaning device 100, the second predetermined amount of fragrance being different than the first amount of fragrance.

The adjustment member 114 may be rotatably coupled to the nozzle housing 107. Further, the adjustment member 114 may transition between the plurality of user-selectable positions based on rotational movement of the adjustment member about a first rotational axis 122 (See FIG. 1A). The adjustment member 114 can include a projection 120 (See FIG. 1C) that can receive a user-supplied force, e.g., from a finger of a user, to transition to a desired user-selectable position of the plurality of user-selectable positions.

As shown, a plurality of visual indicators 116 may be disposed adjacent the adjustment member 114. The plurality of visual indicators 116 can be disposed on the nozzle housing 107. Each of the visual indicators of the plurality of visual indicators 116 may correspond to a user selected position of the plurality of user-selectable positions. The adjustment member 114 can include a selector indicator 118. The selector indicator 118 can be a visual indicator such as a sticker or other surface feature (such as, but not limited to, a concave surface) that can indicate to a user the current user-selected position. As shown in FIG. 1C, the selector indicator 118 is shown disposed adjacent a first user-selectable position. The first user-selectable position in this example is indicated by a corresponding visual indicator of the plurality of visual indicator 116. As shown, this corresponding visual indicator includes a "0" symbol to represent a minimum fragrance strength value (such as but not limited to, zero/off). This first user-selectable position may also be referred to as a closed position. In this closed position, the odor control assembly 110 is preferably configured to emit/output less than 1 milligrams per hour (mg/hour) of fragrance particles. In some examples, the odor control assembly 110 may be configured to emit/output a minimum amount (e.g., substantially zero and/or less than 1 Mg/hour) of fragrance particles when in the closed position.

Each of the plurality of user-selectable positions may be disposed at a predetermined distance from each other. For example, and as shown in FIG. 1C, each of the plurality of user-selectable positions are disposed a uniform distance from each other such that rotation of the adjustment member 114 a predetermined number of degrees about the about a first rotational axis 122 (see FIG. 1A) transitions the adjustment member 114 to a different user-selected position.

As shown in FIG. 1C, a user can transition the adjustment member from the first user-selected position (e.g., the closed position), to a second user-selected position (e.g., the position indicated as "30") based on rotating the adjustment member 114 about the first rotational axis 122 (e.g., counterclockwise 30 degrees). In this example, the odor control assembly 110 may be configured to output/emit/release a second amount of fragrance particles at the second user-selected position. The second amount of fragrance particles released at the second position may be different than the first amount of fragrance particles released at the first position. The second amount of fragrance particles released at the second position can be in a range of 1 to 100 percent (e.g., 1 to 33 percent) of a maximum amount of fragrance particles. By way of a non-limiting example, the maximum amount of fragrance particles may be at least 4 mg/hour, for example, at least 9 mg/hour. In this particular example, the position generally shown with the indicator "90" can be the user-selectable position that outputs the maximum amount of fragrance particles.

Note, this disclosure is not necessarily limited in this regard, and each of the user-selectable positions may be disposed/located at other positions from each other such as 30 degrees, 50 degrees, or 90 degrees. Likewise, the distance between each of the user-selected positions may not necessarily be uniform and may vary.

In at least one example, each successive user-selected position of the plurality of user-selected positions following the closed position causes the odor control assembly 110 to release a greater amount of fragrance particles.

The plurality of user-selectable positions may include a release position. The release position may be at a location that is outside of the user-selectable positions that are used for adjustment of the fragrance particle output. For example, and with reference to FIG. 1C, the release position may be when the adjustment member 114 is rotated 120 degrees counterclockwise from the closed position. The release position may be marked/indicated via a visual indicator (120 degree position) disposed at a corresponding location on the nozzle housing 107, for example.

In the release position, the adjustment member 114 may be configured to decouple from the nozzle housing 107 based on a pulling force supplied by a user along an axis that extends substantially parallel (e.g., coaxially) with the first rotational axis 122. The adjustment member 114 and a fragrance member can be decoupled from the nozzle housing 107 in the release position. The adjustment member 114 and fragrance member may be secured together such that the adjustment member 114 and the fragrance member remain coupled together when the adjustment member 114 is decoupled from the nozzle housing 107.

FIG. 1D shows a cross-sectional view of the surface cleaning device 100 taken along line D-D of FIG. 1A. As shown, the odor control assembly 110 may be disposed at least partially within the nozzle cavity 109, for example, adjacent the first end 112-1 of the nozzle housing 107. The odor control assembly 110 can further include a tray 111, a cam 124, and a fragrance member 126. The adjustment member 114 may be coupled to the tray 111 by way of the cam 124 and/or fragrance member 126. The adjustment member 114 can also be coupled to the nozzle housing 107 directly, or by way of the cam 124 and/or fragrance member 126. The adjustment member 114, cam 124 and fragrance member 126 may be coupled together in a nested/concentric relationship and share a common axis.

The tray 111 may separate the odor control assembly 110 from other components within the nozzle cavity 109, such as control circuitry 128 that can be disposed therein. As shown, the odor control assembly 110 can further include an O-ring 125 that is disposed between the adjustment member 114 and surfaces of the nozzle housing 107 to form a substantially air-tight seal/interface and minimize or otherwise reduce the potential of fragrance particles being released/leaked therethrough.

As further shown, the nozzle housing 107 may include (e.g., define) a dirty air passageway 130 that extends through at least a portion of the nozzle housing 107. The dirty air passageway 130 may be fluidly coupled to a dirty air inlet 132 (See FIG. 1E). The dirty air passageway 130 may be further fluidly coupled to a suction motor as discussed above to draw debris/dirty air into the dirty air passageway 130 for storage within a dust cup or the like. The nozzle housing 107 can further include one or more drive motors 134 (also referred to herein as a second motor) disposed in the nozzle cavity 109. The drive motor 134 may be disposed adjacent the second end 112-2 of the nozzle housing 107. The drive motor 134 may be a DC motor (e.g., a brushed DC motor) and/or an AC motor.

The drive motor 134 may extend from a first end towards a second end along a motor longitudinal axis 152. The motor longitudinal axis 152 may extend substantially parallel with the longitudinal axis 150 of the nozzle housing 107. The first end of the drive motor 134 may include a motor shaft 136, for example, which may be disposed adjacent the second end 112-2 of the nozzle housing 107. The motor shaft 136 can be coupled to the first and/or second wheels 108-1, 108-2 for driving purposes. Alternatively, or in addition, the motor shaft 136 can be coupled to one or more of the agitators/brush rolls 113 (FIG. 1E) to drive the same.

The first end of the drive motor 134 may include an air inlet 131 (FIG. 1D). The air inlet 131 of the drive motor 134 may be disposed adjacent a motor vent/port 132 provided by the nozzle housing 107. A turbine/fan may be coupled to the drive motor 134 that, as the drive motor shaft 136 rotates, a suction force is generated as air is displaced towards the second end of the drive motor 134. Alternatively, low pressure zone created by the dirty air passageway may pull air through the motor vent/port 132 into nozzle cavity 109 and across the drive motor 134. In either case, the suction force may be configured to draw at least 12.0±+−0.5 CFM.

The generated suction force may be configured to draw air from an environment surrounding the nozzle housing 107, via the motor vent 132, and receive the drawn air into the drive motor 134 by way of the air inlet 131 of the motor 134. Thus, the air drawn into the drive motor 134 is so-called "clean" air. The received air may then be drawn over one or more heat-generating components within the drive motor 134, such as a stator and/or windings for cooling purposes. The received air may then absorb heat from the one or more heat-generating components of the drive motor 134. The drive motor 134 may further include an air outlet adjacent the second end of the drive motor 134 to output the heated air. The temperature of the air output by the drive motor 134 in this fashion may be in a range of 25 to 50 Celsius.

The air output from the drive motor 134 can be communicated to the odor control assembly 110. As discussed further below, the airflow rate of the air communicated across the drive motor 134 to the odor control assembly 110, and/or temperature of the communicated air, may be advantageously used to enhance and/or control an amount of fragrance particles output by the odor control assembly 110 during use of the surface cleaning device 100.

As further shown, the dirty air passageway 130 is disposed between the odor control assembly 110 and the drive motor 134.

FIG. 1E shows a cross-sectional view of the surface cleaning device 100 taken along line E-E of FIG. 1B. While the drive motor 134 was previously described as being disposed adjacent the second end 112-2 of the nozzle housing 107 proximate the rear 112-4 (while the odor control assembly 110 is disposed adjacent the first end 112-1 of the nozzle housing 107 proximate the rear end 112-4), it should be appreciated that one or more drive motors may be located anywhere in the nozzle housing 107. For example, a drive motor 138 (also referred to herein as a third motor) can also be disposed in the nozzle housing 107 adjacent to the first and/or second end 112-1, 112-2 of the nozzle housing 107 proximate the front 112-3, and may be configured to drive one or more agitators/brush rolls 113.

Figure 1F:
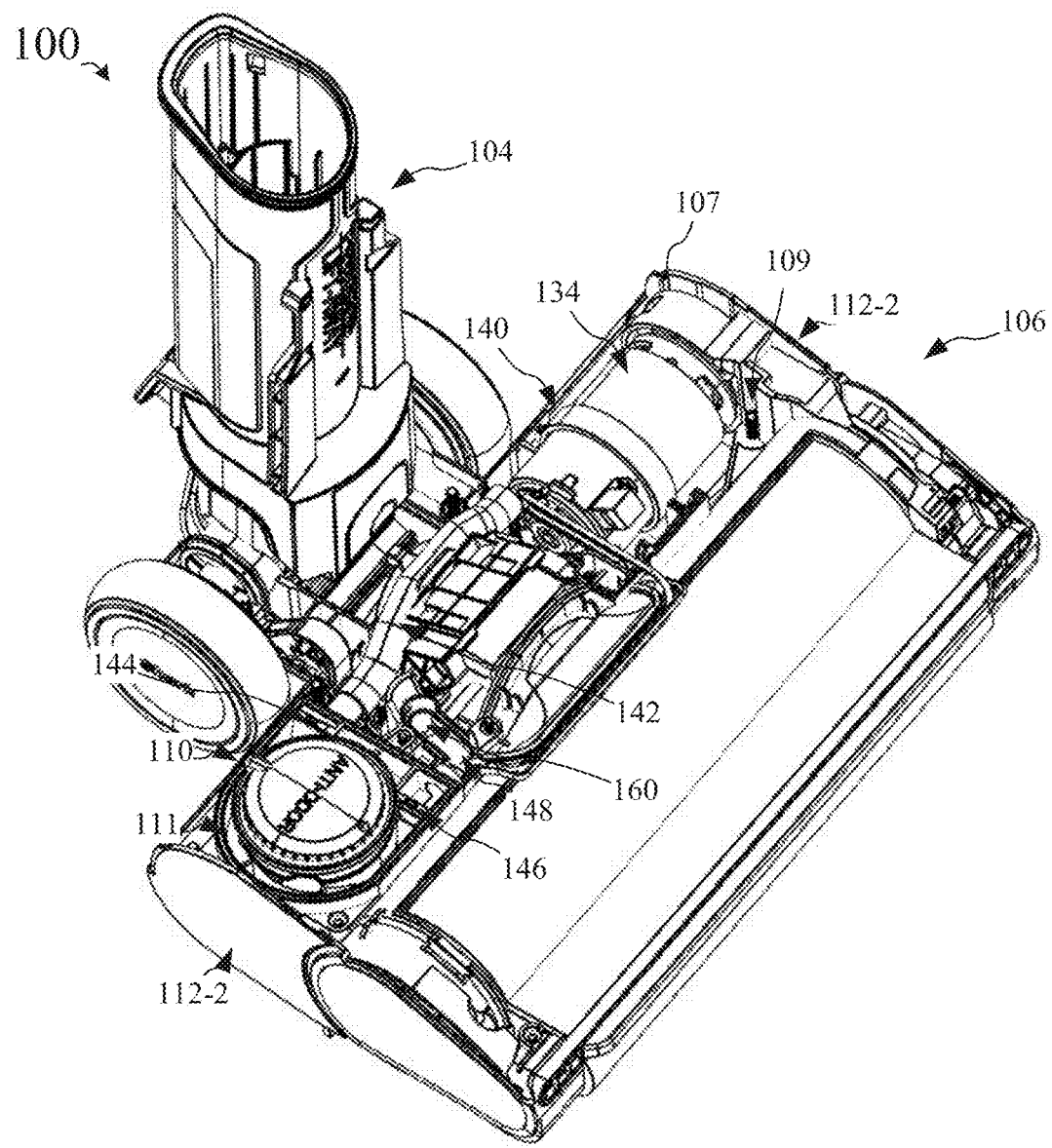
FIG. 1F shows a perspective view of the surface cleaning device of FIG. 1A in accordance with aspects of the present disclosure.

FIG. 1F shows the surface cleaning device 100 with a cover 127 (shown, e.g., in FIG. 1A) of the nozzle housing 107 omitted for purposes of clarity. As shown, the nozzle cavity 109 defines a motor cavity/receptacle 140. The motor cavity 140 may be disposed adjacent the second end 112-2 of the nozzle housing 107. The motor cavity 140 may be configured to securely mount the drive motor 134 within the nozzle housing 107. The motor cavity 140 may be further configured to form an air-tight seal, e.g., when the cover 127 is coupled to the nozzle housing 107. The motor cavity 140 may be fluidly coupled with the motor vent 132 of the nozzle housing 107 to draw air to the drive motor 134, as discussed above. The motor cavity 140 may be fluidly coupled to the odor control assembly 110.

The motor cavity 140 may be fluidly coupled to the odor control assembly 110 via one or more motor conduits/channels 142. The motor conduit 142 may be configured to provide air communicated across the drive motor 134 to the odor control assembly 110. In more detail, the motor conduit 142 may include a first end fluidly coupled to the motor cavity 140 and/or drive motor 134 and a second end fluidly coupled to an inlet 144 of the odor control assembly 110. The motor conduit 142 may extend along a direction that is substantially parallel with the longitudinal axis 150 (see FIG. 1A) of the nozzle housing 107 (see FIG. 1A). The motor conduit 142 can extend at least partially across the dirty air passageway 130 (or fully across). For example, the motor conduit 142 may extend at least partially across the dirty air passageway 130 in a transverse relationship. Alternatively, a conduit, channel, and/or tube can be used to make the coupling between the motor cavity 140 and/or drive motor 134 and the inlet 144 of the odor control assembly 110.

The odor control assembly 110, for example the tray 111 of the odor control assembly 110, may form an air-tight seal with the cover 127 of the nozzle housing 107 when the cover 127 is coupled thereto. An outlet 146 of the odor control assembly 110 may be fluidly coupled to the dirty air passageway 130. As shown, the outlet 146 of the odor control assembly 110 is fluidly coupled to the dirty air passageway 130 by way of an odor conduit/channel 148 and aperture 160. The odor conduit 148 may be formed from a straight, Z-shaped, or L-shaped section. Note, the odor conduit 148 may also be formed from a U-shaped section that forms a trough/channel to direct air output from the outlet 146 of the odor control assembly 110. A bottom surface of the cover 127 of the nozzle housing 107 may be configured to couple to the U-shaped section and form a substantially airtight seal with conduit 148. This may advantageously allow for the bottom surface of the cover 127 of the nozzle housing 107 to define at least a section of the channel/conduit that fluidly couples the outlet 146 of the odor control assembly 110 to the dirty air passageway 130. Alternatively, a tube can be used to make the coupling between the outlet 146 of the odor control assembly 110 and passageway 130.

Figure 1G:
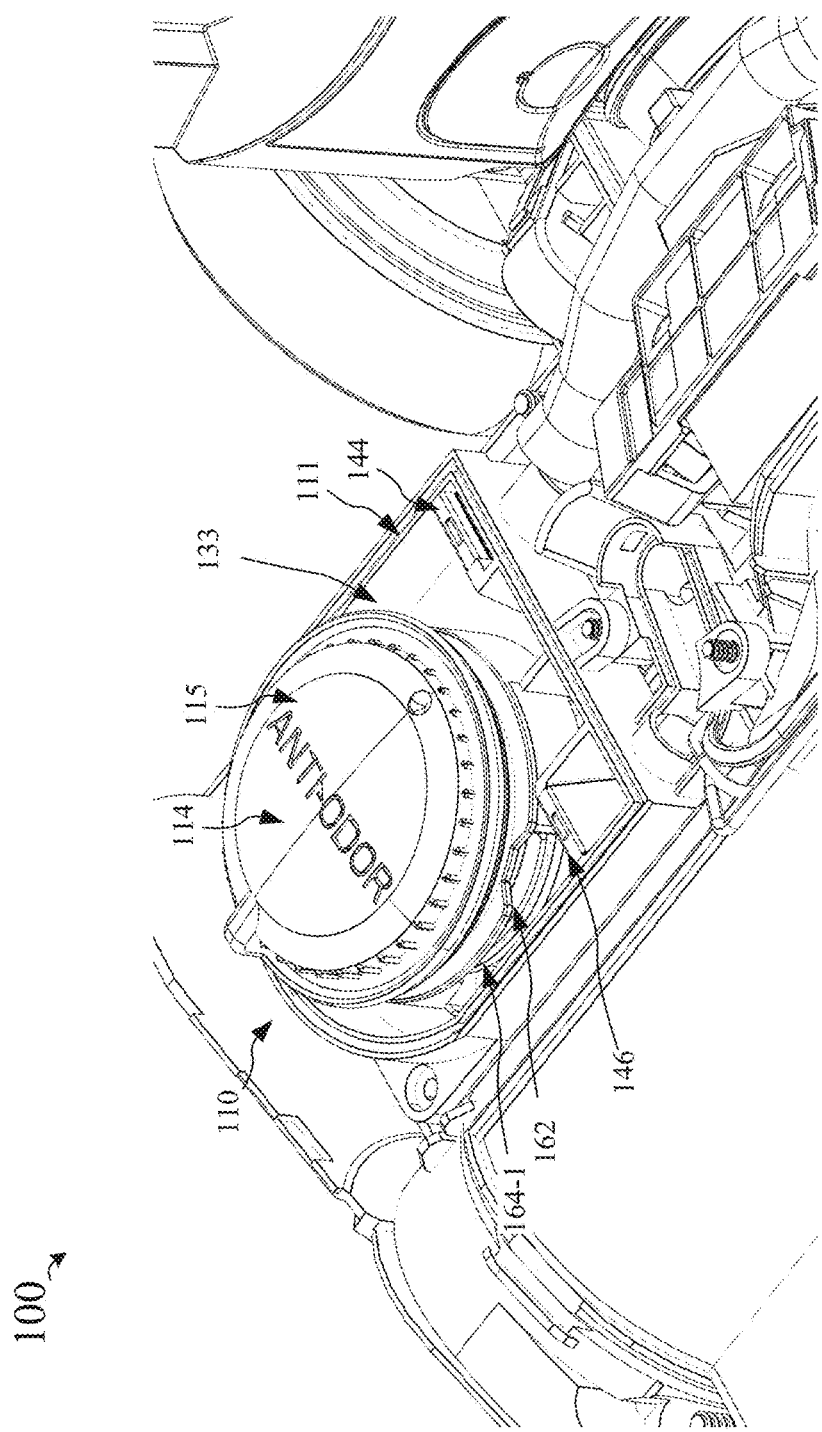
FIG. 1G shows an enlarged section of the surface cleaning device shown in FIG. 1F.
Figure 1H:
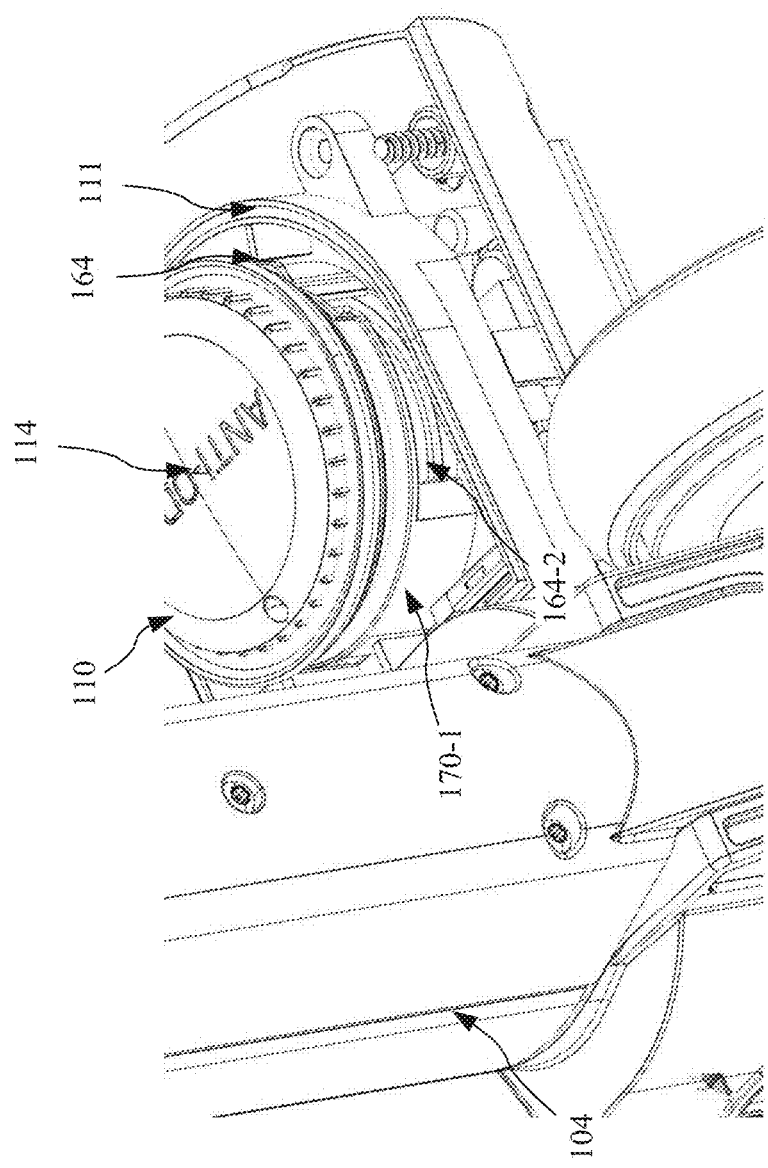
FIG. 1H shows another enlarged section of the surface cleaning device shown in FIG. 1F.

FIGS. 1G and 1H each show an enlarged section of the nozzle housing 107 of the surface cleaning device 100 shown in FIG. 1F. In some examples, the inlet 144 of the odor control assembly 110 may include a one-way valve. The one-way valve can include a valve member formed from a material such as Ethylene Propylene Diene Monomer (EPDM) rubber or Acrylonitrile Butadiene rubber (also known as Nitrile rubber or Buna) for example. The valve member may be configured to be displaced into a cavity 133 (which may be at least partially defined by the tray 111), for example, based on the air flowing from the drive motor 134. The displaced valve member then permits the air communicated from the drive motor 134 to enter the cavity 133. On the other hand, the valve member may be further configured to return (e.g., based on the elasticity of the material forming the valve member) to a seated position against the inlet 144, when the flow rate and/or pressure of the air from the drive motor 134 falls below a threshold (e.g., drive motor 134 is turned off) to minimize or otherwise substantially prevent air from escaping from the cavity 133 of the tray 111. The outlet 146 can include a similar configuration to that of the inlet 144 and can also include a one-way valve configuration. Thus, generally in the absence of air communicated across the drive motor 134, the inlet 144 and/or the outlet 146 may be configured to close/seal based on a respective valve member returning to a seated position. In the closed/sealed position, each of the inlet 144 and outlet 146 may prevent at least 80% of air flow therethrough, for example, prevent at least 90% of air flow through.

As further shown, the adjustment member 114 may be disposed at a user-selected position that at least partially fluidly couples one or more through holes or fragrance passageways 162 of the fragrance member 126 (See FIG. 1D) with the inlet 144, and thus by extension the drive motor 134 to receive the air communicated by the same. The adjustment member 114 may include a base 115 (See FIG. 1G). The base 115 may also be referred to herein as cap or grip portion. The base 115 of the adjustment member 114 may further include first and second arms 170-1, 170-2 extending therefrom (See FIGS. 1H and 1I). The first and second arms 170-1, 170-2 may extend from the base 115, e.g., substantially parallel with each other. The first and second arms 170-1, 170-2 may be disposed on opposite sides of the base 115. These features of the adjustment member 114 may also be more clearly seen in FIGS. 2D-2G.

The cam 124 (see FIG. 1D) may define first and second apertures 164-1, 164-2 (see FIGS. 1G-1H), for example, which may be disposed opposite each other. The first and second apertures 164-1, 164-2 may align with each other, such as is shown in the example of FIGS. 2H and 2I. The first and second apertures 164-1, 164-2 may be configured to generally align with the one or more fragrance passageways 162 of the fragrance member 126 when the fragrance member 126 is disposed between the first and second apertures 164-1, 164-2 of the cam 124. The adjustment member 114 may be configured to rotate relative to the cam 124 about the first rotational axis 122 (FIG. 1A), with the cam 124 (and the fragrance member 126) remaining in a fixed position. The rotation of the adjustment member 114 may then bring the first and second arms 170-1, 170-2 of the adjustment member 114 to a position that at least partially blocks/obstructs the first and second apertures 164-1, 164-2 of the cam 124 to minimize or otherwise reduce air flow through the fragrance member 126.

Alternatively, the first and second arms 170-1, 170-2 can be integrated into the nozzle housing 107 as a continuous, cylindrical extrusion. This extrusion can contain one or more through holes that act as air passageways through the fragrance member 126. The adjustment member 114, cam 124, and fragrance member 126 may rotate together as one unit while the extrusion in the nozzle housing 107 remains stationary.

The first and second arms 170-1, 170-2 may be configured to selectively block a portion or the entirety of the first and second apertures 164-1, 164-2 such that at least a portion of the air flow through the fragrance member 126 is prevented, and in the case of the aforementioned closed position for the adjustment member 114, substantially all air flow is prevented through the fragrance member 126, e.g., at least 90% of air flow is prevented/restricted.

Thus, the amount of air passing through the at least one through hole 162 of the fragrance member 126 may be selectively increased or decreased based on the alignment of the first and second arms 170-1, 170-2 of the adjustment member 114 relative to the first and second apertures 164-1, 164-2 of the cam 124.

The example of FIG. 1G shows the adjustment member 114 in an open position. In this open position, the first aperture 164-1 of the cam 124 and the at least one through hole 162 of the fragrance member are fluidly coupled to the inlet 144. FIG. 1H shows the example of FIG. 1G from the opposite side. As shown, the first arm 170-1 of the adjustment member 114 partially blocks the second aperture 164-2 of the cam 124. Thus, in this example the amount of air flow through the fragrance member 126 is less a maximum airflow but greater than zero.

FIG. 1I shows an enlarged section of the nozzle housing 107 of the surface cleaning device 100 shown in FIG. 1F. As shown, the adjustment member 114 may be transitioned to a user-selectable position that fluidly decouples the at least one fragrance passageway 162 (See FIG. 1H) of the fragrance member 126 from the air communicated across the drive motor 134 based on the first and second arms 170-1, 170-2 of the adjustment member 114 blocking the first and second apertures 164-1, 164-2 of the cam 124. This user-selectable position may also be referred to as a closed position. Note, the adjustment member 114 is not necessarily limited to a single user-selectable position that fluidly decouples the at least one fragrance passageway 162 of the fragrance member 126 from the air communicated across the drive motor 134.

Figure 1J:
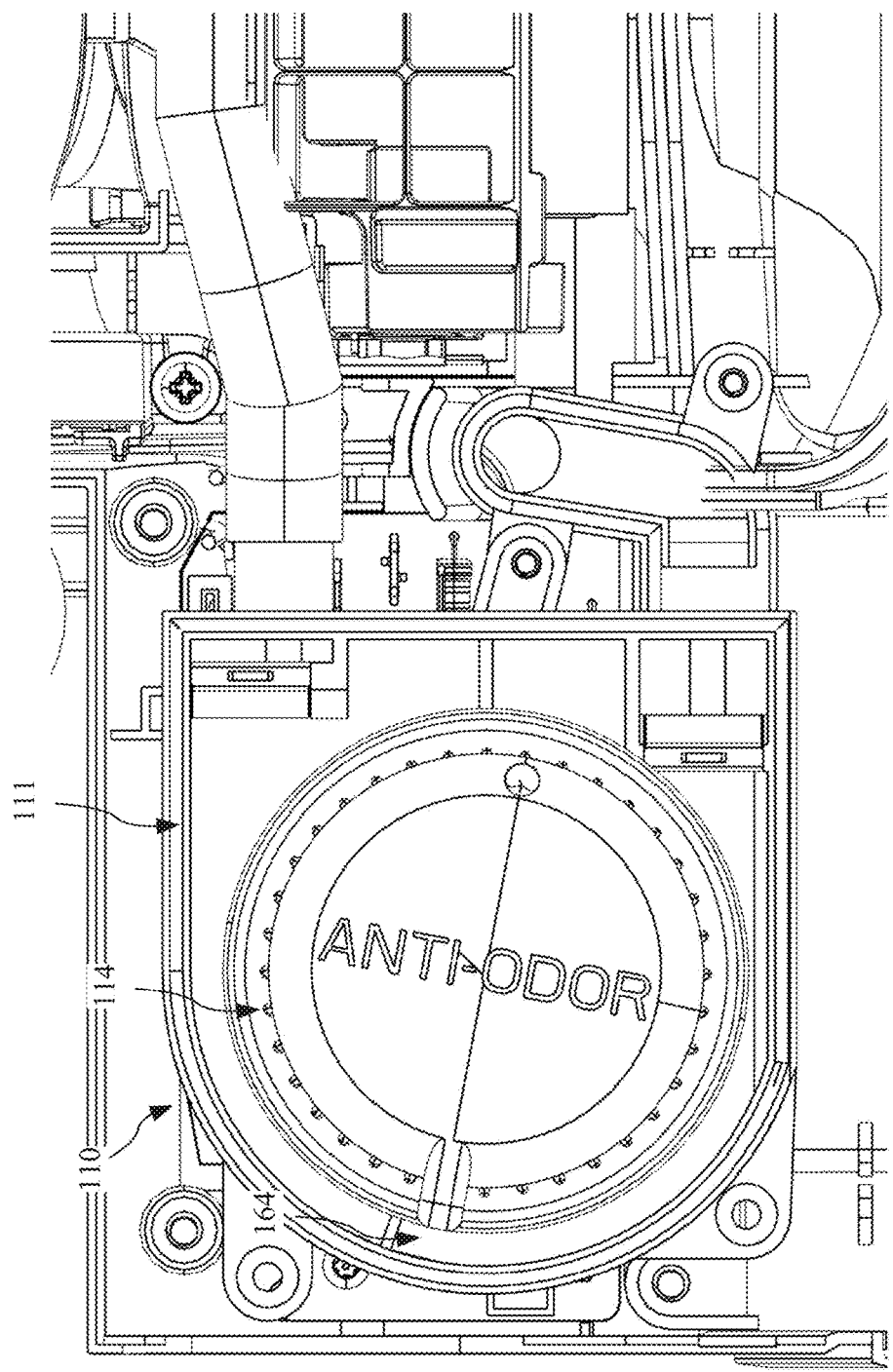
FIG. 1J shows another enlarged section of the surface cleaning device shown in FIG. 1F.

As further shown in FIG. 1I, this closed position may also fluidly couple a bypass path 174 to the air communicated across the drive motor 134. As shown more clearly in FIG. 1J, the bypass path 174 is defined at least in part by the tray 111 and the outer surfaces of the adjustment member 114 and/or cam 124. The bypass path 174 may be configured to receive at least 80% of air communicated across the drive motor 134, and more preferably at least 99% of air communicated across the drive motor 134, when the adjustment member is in the closed position. Conversely, when the adjustment member 114 is in an open position (such as shown in FIG. 1H), air flow through the bypass path 174 may be at least partially reduced.

Returning briefly to FIG. 1I, a yoke/projection feature 166 can be provided by the adjustment member 114 or the tray 111. As shown, yoke feature 166 may be defined by the tray 111 and may extend towards the adjustment member 114. In this example, the adjustment member 114 (and/or cam 124) can include an outer diameter that varies in width, with the varying width being used to vary the opening to the bypass path 174. This feature is analogous to a concentric nut.

Accordingly, when the adjustment member 114 is in the closed position, such as shown in FIG. 1H, the opening of the bypass path 174 may be at a maximum width to permit a maximum predetermined amount of air flow. Conversely, when the adjustment member 114 is in an open position, such as shown in FIG. 1I, the opening to the bypass path 174 may be closed or otherwise reduced.

The odor control assembly 110 may be configured to utilize the bypass path 174 to ensure that a substantially equal or constant amount of air flow flows across the drive motor 134 regardless of the particular user-selected position for the adjustment member 114. This may advantageously avoid overheating the drive motor 134. Consider an example where a user transitions the adjustment member 114 to a position that causes 50% of a maximum amount of fragrance particles to be output by the odor control assembly 110. In this example, the bypass path 174 may be configured to receive about half of the air communicated across the drive motor 134 while the remaining portion is passed through the at least one through hole of the fragrance member 126.

The bypass path 174 is preferably configured to receive air communicated across the motor 134 along a first direction and redirect the received air along a second direction, with the first and second directions being different. More preferably, the first direction may extend away from the motor 134 and towards the odor control assembly 110, and the second direction may extend towards dirty air passageway 130. The bypass path 174 may be curved.

Note, the odor control assembly 110 is not necessarily limited to being fluidly coupled to the drive motor 134 as discussed above. The odor control assembly 110 can include the inlet 144 fluidly coupled to other air sources, such as the suction motor. The odor control assembly 110 is also not necessarily limited to providing/outputting fragrance particles to the dirty air passageway 130 of the surface cleaning device 100 as discussed above. Alternatively, or in addition, the odor control assembly 110 may output fragrance particles to the environment, e.g., without communicating fragrance particles through the dirty air path 130, or may output fragrance particles at a clean air output of the suction motor, for example. As a further note, the odor control assembly 110 may not necessarily be disposed/mounted on the nozzle housing 107 as shown FIG. 1A. The odor control assembly 110 can be disposed/mounted on the nozzle housing 107 at a different location, such as at a center of the nozzle housing 107, or mounted on other features/structures of the surface cleaning device 100 such as the upright section 104, on a wand assembly that can couple to the upright section 104, on a handle that couples to the upright section 104, within a dust cup (not shown), or in a hose to dust cup connection, for example.

Figure 2A:
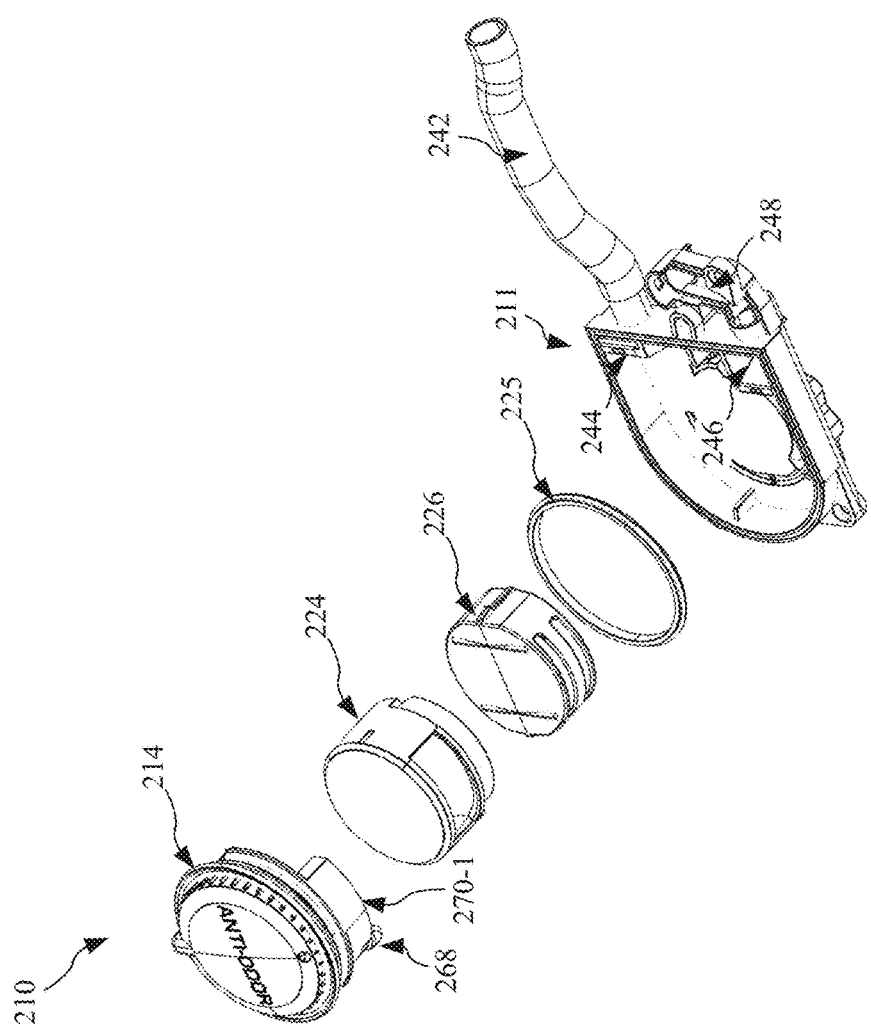
FIG. 2A shows a partially exploded view of an odor control assembly consistent with aspects of the present disclosure.

FIG. 2A shows an exploded view of an example odor control assembly 210 consistent with aspects of the present disclosure. The odor control assembly 210 may be used to implement the odor control assembly 110 of FIGS. 1A-1J, the various features and examples of which are equally applicable to the odor control assembly 210 and will not be repeated for brevity.

The odor control assembly 210 includes an adjustment member 214, a cam 224, a fragrance member 226, an O-ring 225, and a tray 211. As shown, the odor control assembly 210 can further include a conduit/pipe 242 to fluidly couple to an inlet 244 defined by the tray 211. The conduit 242 is preferably utilized to fluidly couple air communicated across a drive motor to the odor control assembly 210. The odor control assembly 210 can further include a conduit/pipe 248 to fluidly couple an outlet 246 defined by the tray 211 to a dirty air passageway, such as the dirty air passageway 130 as discussed above.

Figure 2B:
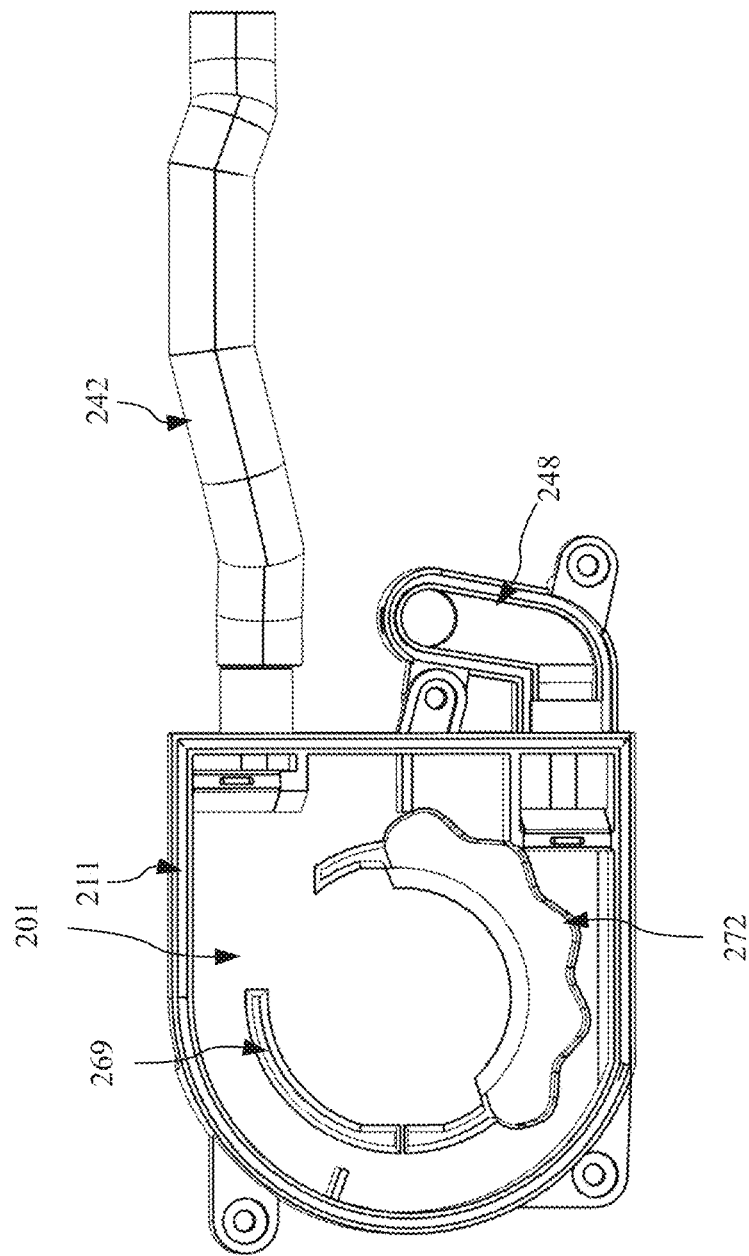
FIG. 2B shows a top view of a tray of the odor control assembly of FIG. 2A in isolation.
Figure 2C:
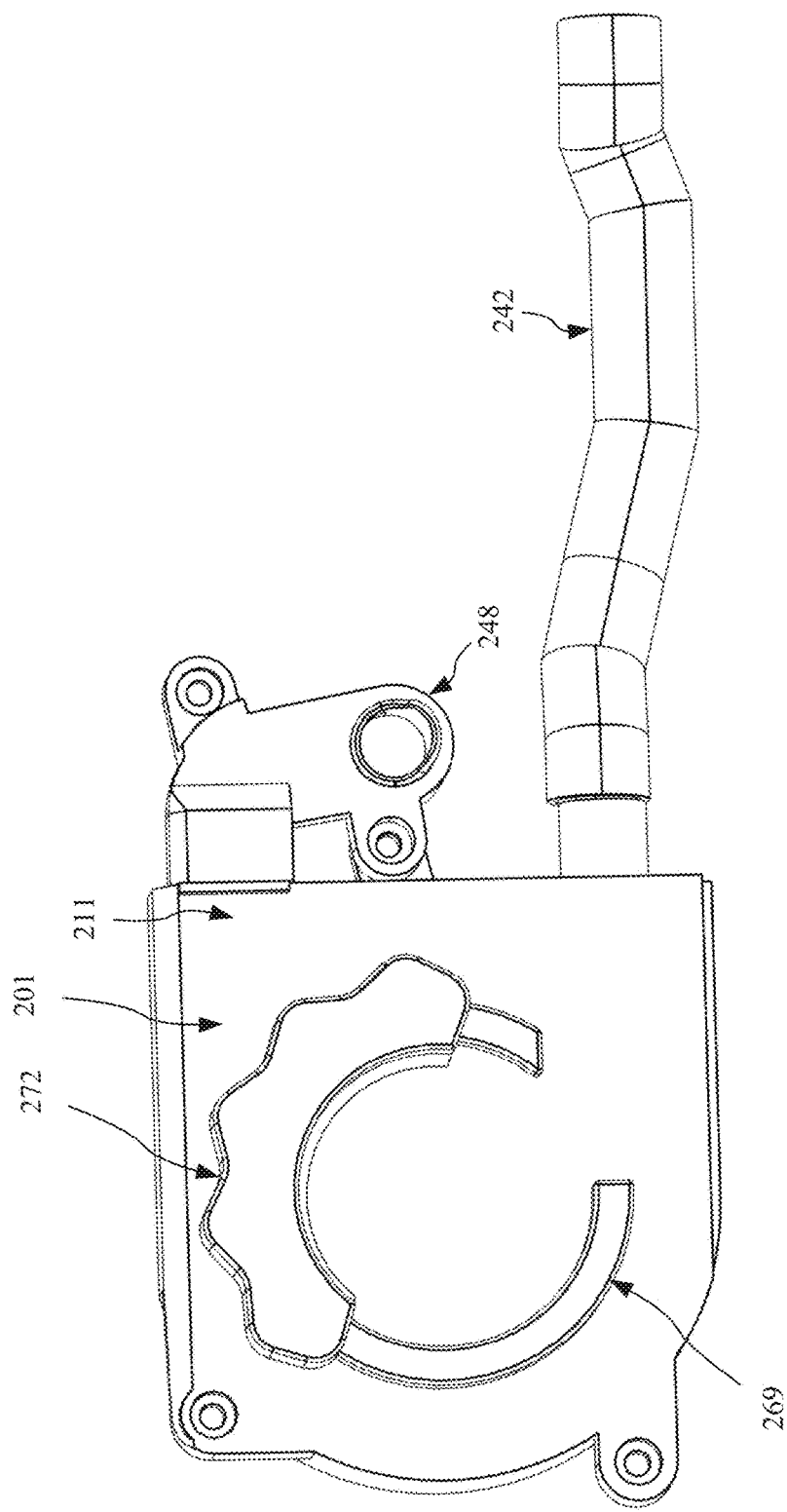
FIG. 2C shows a bottom view of the tray of FIG. 2B.
Figure 2D:
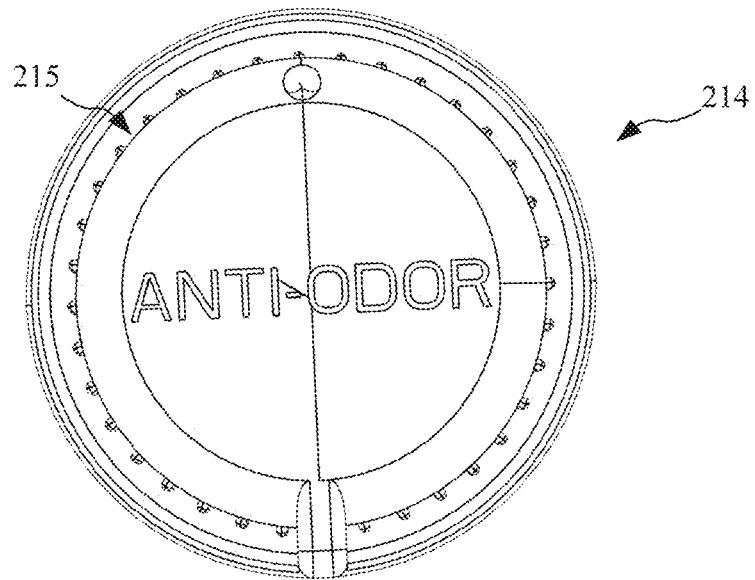
FIG. 2D shows a top view of an adjustment member of the odor control assembly of FIG. 2A in isolation.
Figure 2E:
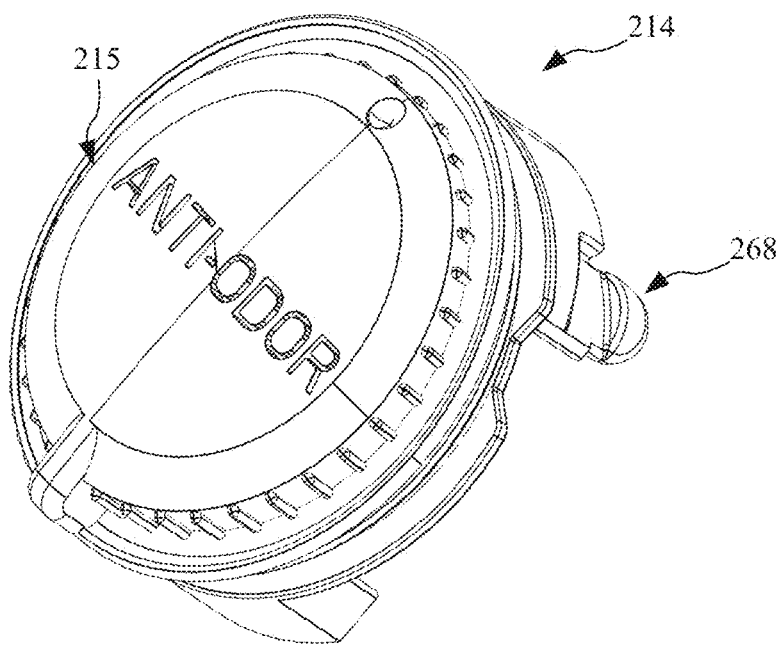
FIG. 2E shows a perspective view of the adjustment member of FIG. 2D.
Figure 2F:
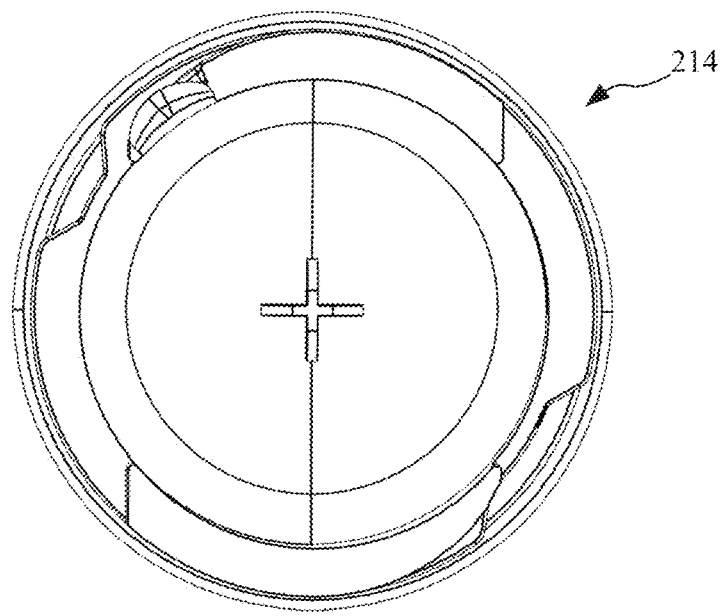
FIG. 2F shows a bottom view of the adjustment member of FIG. 2D.

FIGS. 2B and 2C shows the tray 211 of FIG. 2A. The tray 211 may include a material such as Acrylonitrile Butadiene Styrene (ABS), Polypropylene, Polyphenylene Ether, Polyoxymethylene or Polypropylene. As shown, a bottom surface 201 of the tray 211 may define at least one channel/recess 269. The at least one channel 269 may be configured to receive a portion of the cam 224 and/or the adjustment member 214 for coupling purposes. The at least one channel 269 may be preferably configured to provide a track/guide to allow for rotational movement of the adjustment member 214, cam 224, and/or fragrance member 226, and thus by extension, allows for the adjustment member 214 to be transitioned between the plurality of user-selectable positions as discussed above. The at least one channel 269 may be configured to allow for the adjustment member 214 to be rotated 360 degrees, or limit the movement to less than 360 degrees. For example, and as shown, the at least one channel 269 is configured to allow for the adjustment member 214 to rotate a maximum of 120 degrees.

As further shown, the at least one channel 269 preferably further defines one or more position grooves 272. More preferably, the at least one channel 269 may define a plurality of such position grooves 272. Each groove of the one or more position grooves 272 may correspond to a different user-selectable position for the adjustment member 214. The adjustment member 214 may further include a position projection/tab 268 (See FIG. 2A) that can be received by each of the one or more position grooves 272. The position projection 268 may extend from the first arm 270-1 of the adjustment member 214. Alternatively, the position projection/tab 268 may be included in the cam 224, but may extend from another portion of the adjustment member 214.

The position projection 268 of the adjustment member 214 and the one or more position grooves 272 can collectively provide a tongue and groove arrangement. The position projection 268 is further preferably configured to provide tactile feedback to a user when a user transitions the adjustment member 214 between the user-selectable positions. The position projection 268 is further configured to "lock" in place when the adjustment member is transitioned between the plurality of user-selectable positions. When a user desires to change the current user-selected position, the user then supplies a rotational force to the adjustment member 214 that is sufficient to cause the position projection 268 to be displaced and/or resiliently deformed, e.g., by the curved sidewalls defining the one or more grooves 272. This displacement/resilient deformation of the position projection 268 generates a counter force/spring force. As rotation of the adjustment member 214 occurs, the position projection 268 is then aligned with a next position groove 272 and the position projection 268 then "snaps" into the same based on the spring force of the position projection 268 being released. This advantageously provides tactile feedback to the user to indicate that a next user-selected position has been reached. Also, this tongue and groove arrangement can maintain/hold the adjustment member 214 at the user-selected position to withstand the movements and/or vibrations that occur during use of the surface cleaning device 100.

FIGS. 2D-2G show the adjustment member 214 of FIG. 2A in isolation. The adjustment member 214 may include a material such as Acrylonitrile Butadiene Styrene (ABS), Polypropylene, Polyphenylene Ether, Polyoxymethylene or Polypropylene. In some examples, the adjustment member 214 may have a cylindrical profile such as shown, although other shapes/profiles are within the scope of this disclosure.

FIGS. 2H-2I show the cam 224 of FIG. 2A in isolation. The cam 224 may include a material such as Polyphenylene Ether, Polyoxymethylene, or polypropylene. In some examples, the cam 224 may have a cylindrical profile such as shown, although other shapes/profiles are within the scope of this disclosure.

The cam 224 may include first and second apertures 264-1, 264-2, for example, disposed on generally opposite sides. As discussed above, the first and second apertures 264-1, 264-2 can be aligned with the one or more through holes or fragrance passageways 262 (See, e.g., FIGS. 2J-2L) of the fragrance member 226. The cam 224 may be fixedly coupled to the fragrance member 226 and/or to the tray 211. Thus, the cam 224 and the fragrance member 226 may remain in a fixed position as the adjustment member 214 is rotated to a given user-selectable position. Alternatively, the adjustment member 214, cam 224, and fragrance member 226 can be fixed together while rotating to a given user-selectable position. An additional, stationary component may be provided to partially and/or completely bock the first and second apertures 264-1, 264-2 on the cam 224.

Figure 2G:
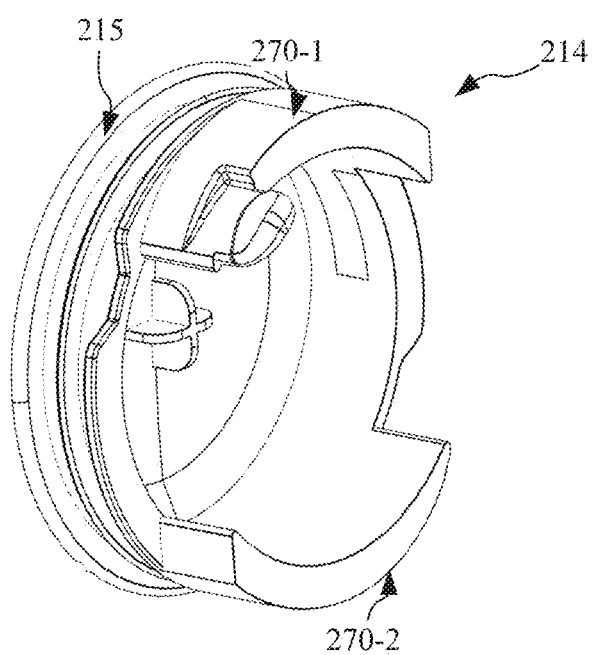
FIG. 2G shows another perspective view of the adjustment member of FIG. 2D.
Figure 2H:
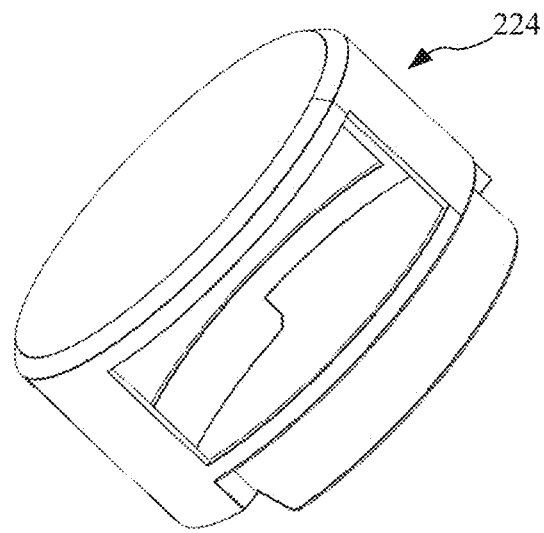
FIG. 2H shows a perspective view of a cam of the odor control assembly of FIG. 2A in isolation.
Figure 2I:
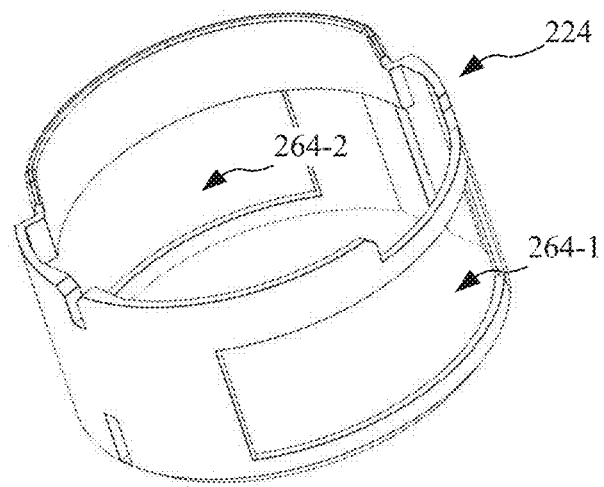
FIG. 2I shows another perspective view of the cam of FIG. 2H.

The adjustment member 214 may then vary the amount of air passing to the fragrance member 226, for example, based on the position of the first and second arms 270-1, 270-2 (see FIG. 2G). The first and second arms 270-1, 270-2 may be configured to at least substantially completely/entirely block the first and second apertures 264-1, 264-2 when the adjustment member 214 is in the closed position. On the other hand, the first and second arms 270-1, 270-2 may be configured to only partially block/obstruct the first and second apertures 264-1, 264-2 to vary an amount of fragrance particles output by the odor control assembly 210, e.g., based on a desired user selection, or not block the first and second apertures 264-1, 264-2 such that a maximum amount of fragrance particles is output by the odor control assembly 210. In any such cases, the adjustment member 214 may adjust the cross-section of the airpath opening to fragrance member 226 to vary an overall amount of fragrance particles output by the odor control assembly 210.

Figure 2J:
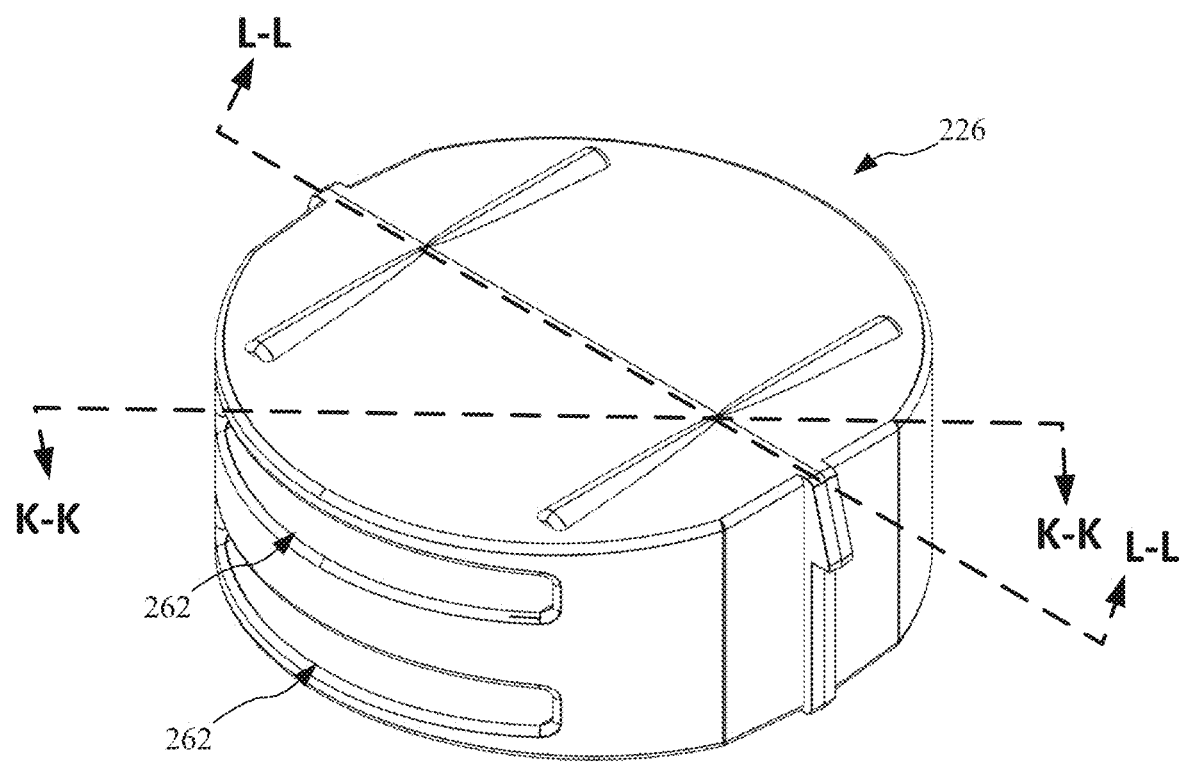
FIG. 2J shows a perspective view of a fragrance member of the odor control assembly of FIG. 2A in isolation.

FIG. 2J shows the fragrance member 226 of FIG. 2A in isolation. The fragrance member 226 may include a material including at least one of Ethylene-vinyl Acetate, Thermoplastic Polyurethane, and/or Polyolefin. The fragrance member 226 may be infused with one or more fragrance oils, and/or one or more fragrance oils are disposed on the fragrance member 226. The fragrance member 226 may include the one or more fragrance oils infused and/or disposed on the surfaces defining the one or more through holes or fragrance passageways 262. In any such cases, the fragrance member 226 may be formed as a solid. In some embodiments, the fragrance member 226 may include a liquid fragrance. The liquid fragrance may be dispensed, for example, using a wick, evaporation, or the like.

Figure 2K:
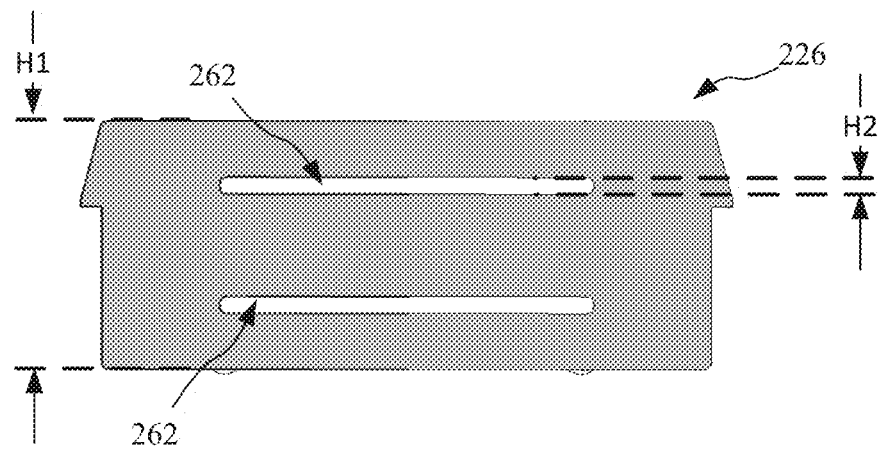
FIG. 2K shows a cross-sectional view of the fragrance member of FIG. 2J taken along line K-K.

FIG. 2K shows a cross-sectional view of the fragrance member 226 taken along line K-K of FIG. 2J. The fragrance member 226 may include at least one through hole/fragrance passageway 262, and optionally may include a plurality of through holes/fragrance passageways 262, such as shown. The fragrance member 226 may have a cylindrical shape. Each through hole/fragrance passageway 262 may extend through the fragrance member 226, for example, in transverse relationship relative to the longitudinal axis. When a plurality of through holes/fragrance passageways 262 are utilized, such as shown, each of the plurality of through holes/fragrance passageways 262 may extend substantially in parallel with each other. The through holes/fragrance passageways 262 may also be collectively referred to as a fragrance air path. The fragrance air path may be formed from one or more through holes/fragrance passageways 262, or may alternatively be provided by other features such as a top and/or bottom surface of the fragrance member 226. Thus, the fragrance air path provided by the fragrance member 226 is not necessarily limited to through holes/fragrance passageway 262.

Figure 2L:
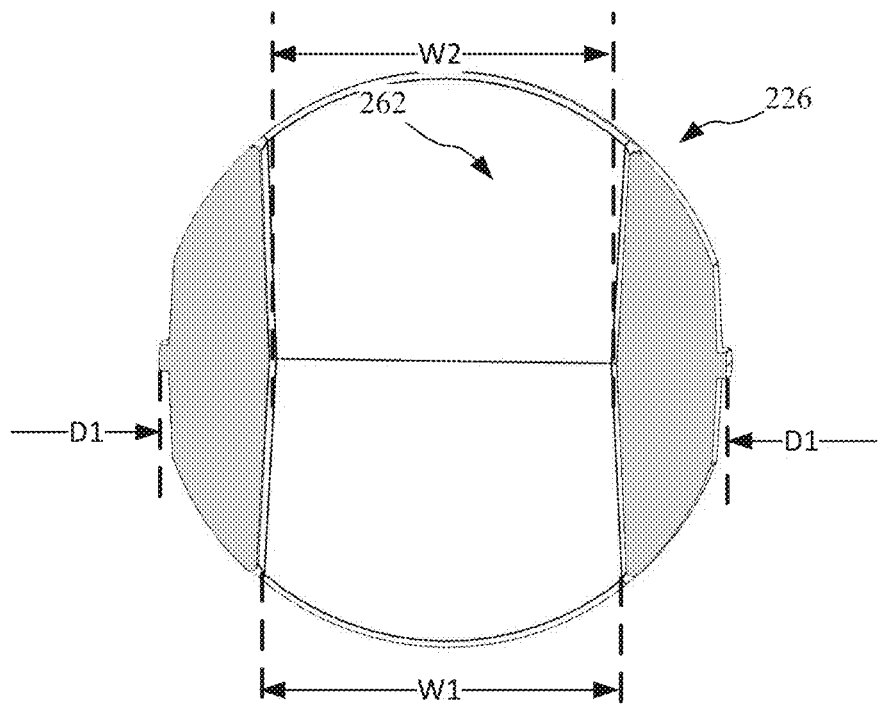
FIG. 2L shows a cross-sectional view of the fragrance member of FIG. 2J taken along line L-L.

FIG. 2L shows a cross-sectional view of the fragrance member 226 taken along line L-L of FIG. 2J. As shown, the fragrance member 226 preferably has an overall diameter of D1. The overall diameter D1 measures preferably in a range of 30 to 50 mm. The overall height H1 of the fragrance member 226 is preferably in a range of 5 to 50 mm.

One or more (e.g., each) of the through holes/fragrance passageways 262 may have an overall height H2 that is in a range of 1 to 10 mm. One or more (e.g., each) of the through holes/fragrance passageways 262 may have a first overall width W1. The first overall width W1 may be in a range of 15 to 40 mm, for example, 25 to 35 mm. The opening of the through holes/fragrance passageways 262 may have a first overall width W1 that transitions to a second overall width W2 at about a center of the fragrance member 226. The second overall width W2 may be less than the first overall width W1 to provide a tapered section (which may also be referred to herein as an internal taper). The tapered section may be advantageously utilized to increase velocity of air passing through the through holes/fragrance passageways 262. The second overall width W2 may be in a range of 10 to 35 mm, for example, 20 to 30 mm.

The fragrance member 226 may be configured to emit at least 4 mg/h of fragrance particles, and more preferably, at least 9 mg/h. The fragrance member 226 may be further preferably configured with an operational/functional life of at least six months, based on a target usage of up to one hour per week, wherein the fragrance member 226 is configured to emit at least 4 mg/h for at least the six months.

Figure 3A:
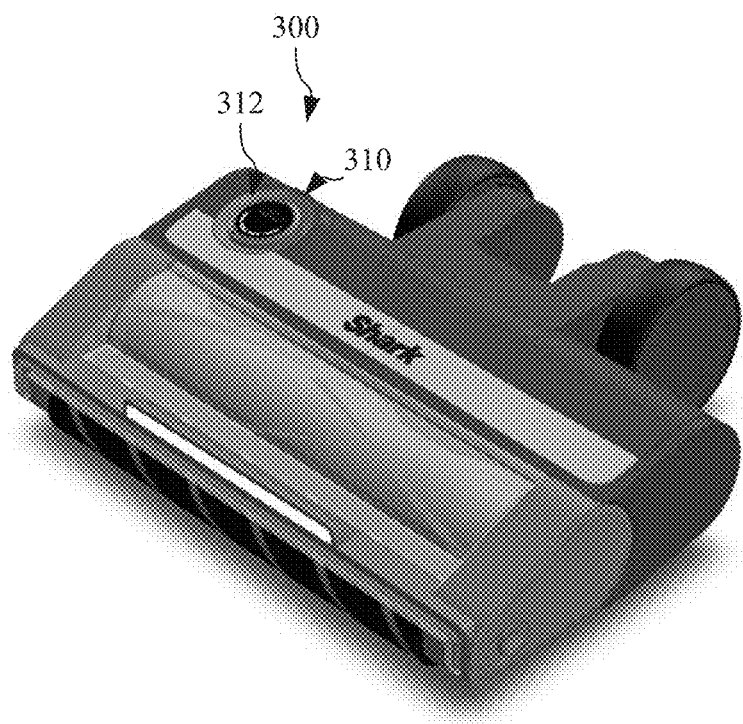
FIG. 3A shows another example surface cleaning device consistent with aspects of the present disclosure.
Figure 3B:
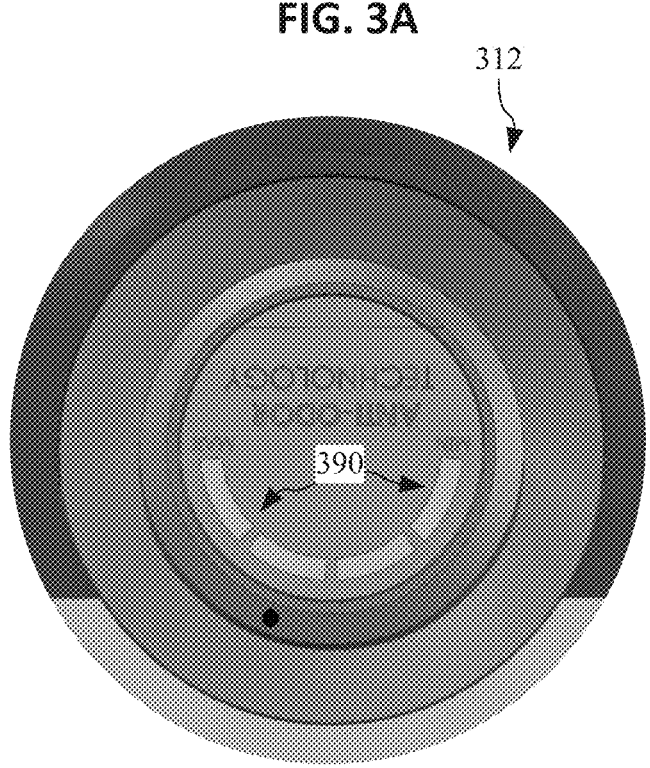
FIG. 3B shows an adjustment member suitable for use in the surface cleaning device of FIG. 3A.

FIG. 3A shows another example surface cleaning device 300 consistent with aspects of the present disclosure. As shown, the surface cleaning device 300 can include an odor control assembly 310 that is configured substantially similar to that of the odor control assembly 110/210 as discussed above. The odor control assembly 310 may further include an adjustment member 312 that includes at least one visual indicator. As shown in FIG. 3B, the visual indicator can include an array of status lights 390 that can collectively provide a dial/gauge. The status lights 390 can be illuminated by one or more LEDs, for example. The dial/gauge may be used to show the currently user-selectable position for the adjustment member 312. In the example of FIG. 3A, this can include four open positions. The first position therefore can correspond with a minimum amount of fragrance particles being output by the odor control assembly 310 and the last position can correspond with a maximum amount of fragrance particles being output by the odor control assembly 310.

Stated more simply, the three positions may then correspond to 33% output, 66% output and 100% output of fragrance particles by the odor control assembly 310, respectively (though it should be understood that the present disclosure is not limited to these outputs and/or number of positions unless specifically claimed as such). Selecting the first position may energize the right most of the status lights 390, selecting the second position may energize the two right-most status lights 390, and so on. The "closed" position may be indicated by none of the status lights 390 being energized. The adjustment member 312 may be configured to be rotated by a user as to transition between these user-selectable positions. Alternatively, or in addition, the adjustment member 312 can include a touch-sensitive region/surface to allow for a user input a gesture, such as a finger swipe, in order to transition the adjustment member 312 between user-selectable positions. This embodiment may include linkages/actuators/gears or other mechanical components that can be electrically actuated to adjust the amount of air flow through the associated fragrance member.

Still further, adjustment between the user-selectable positions may not necessarily include rotational movement of an adjustment member. For example, the adjustment member may also be implemented as a shutter/sliding door with minor modification. In this example, the adjustment member may then be displaced along a linear path to transition between user-selectable positions. In any such cases, the adjustment member preferably slidably moves between the user-selectable positions to allow for a user to conveniently set an amount of fragrance particles to output during operation of a surface cleaning device.

Figure 4A:
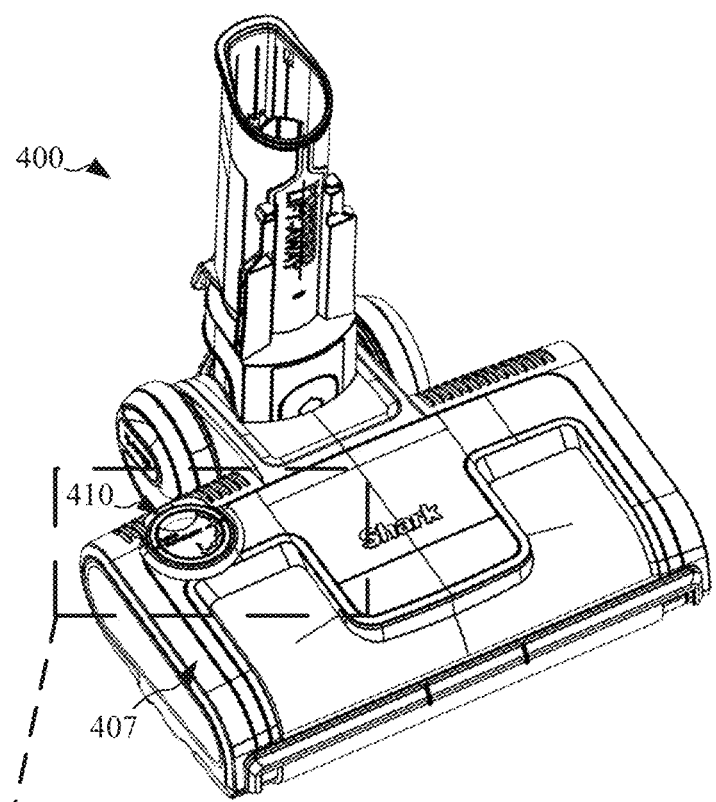
FIG. 4A shows another example surface cleaning device consistent with aspects of the present disclosure.

FIG. 4A shows another example surface cleaning device 400 consistent with aspects of the present disclosure. As shown, the surface cleaning device 400 can include an odor control assembly 410 that is configured substantially similar to that of the odor control assembly 110/210/310 as discussed above. However, the odor control assembly 410 may further include an adjustment member 414 that includes a rotatable section 415, which is shown more clearly in FIG. 4B.

Figure 4B:
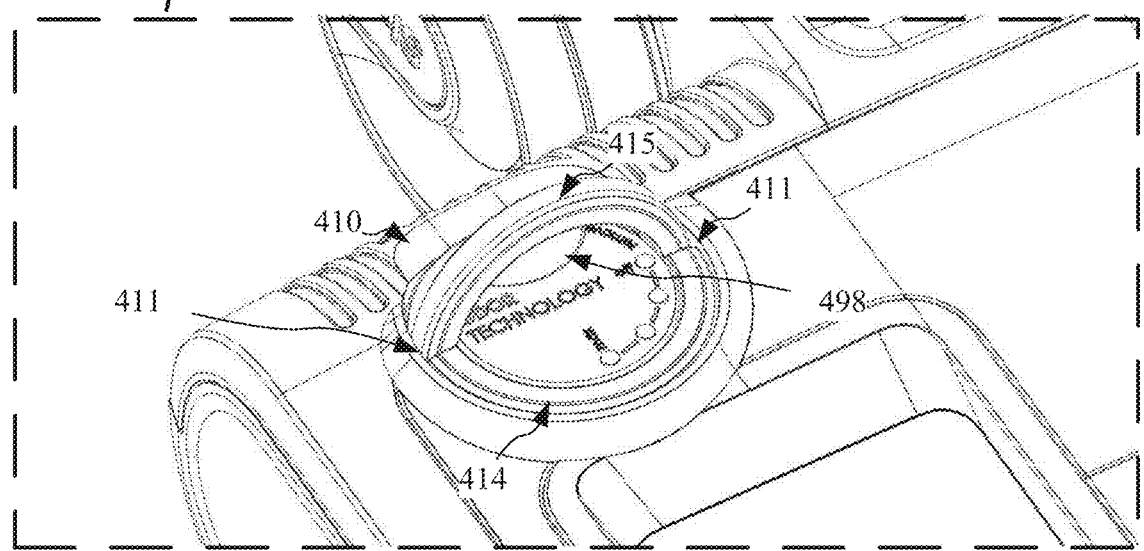
FIG. 4B shows an enlarged section of the surface cleaning device of FIG. 4A.

As shown, the rotatable section 415 can transition from a first orientation, such as shown in FIG. 4A, to a second orientation, such as shown in FIG. 4B. The first orientation for the rotatable section 415 may include the rotatable section 415 being flush with surfaces defining the adjustment member 414 (see FIG. 4B). The second orientation for the rotatable section 415 may include the rotatable section 415 extending from the nozzle housing 407 at a predetermined angle, such as a predetermined angle of 90 degrees. The second orientation of the rotatable section 415 may therefore be referred to as an extended position.

The rotatable section 415 may include an arcuate profile that defines a through hole 498 when transitioned to the second orientation such that the rotatable section 415 may function as a handle. A user may then cause the rotatable section 415 to rotate from the first orientation to the second orientation, e.g., using a force supplied by one or more fingers. Then, a user can then grip the rotatable section 415 by inserting one or more fingers into the through hole 498. The user may then supply a force to the rotatable section 415 to cause rotation of the adjustment member 414 as discussed above to transition the same between a plurality of user-selectable positions for purposes of selecting a desired amount of fragrance particles to be output by the odor control assembly 410. The rotatable section 415 may be rotatably coupled to the adjustment member 414 via one or more hinges 411 to transition between the first and second orientations and may also fixedly coupled to the adjustment member 414 to allow for a user-supplied force to cause rotation (e.g., via torque) of the adjustment member 414.

Figure 5A:
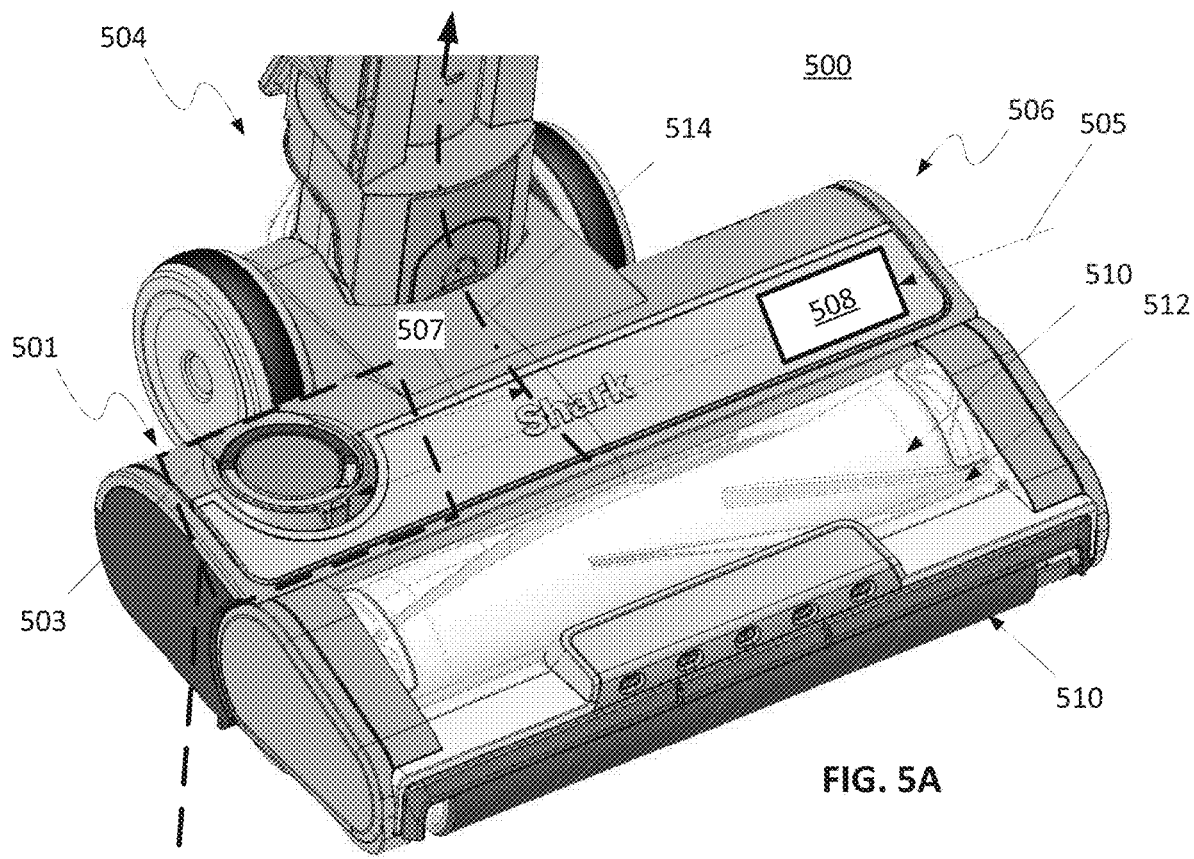
FIG. 5A shows another example of a surface cleaning device including an odor control assembly consistent with the present disclosure.
Figure 5B:
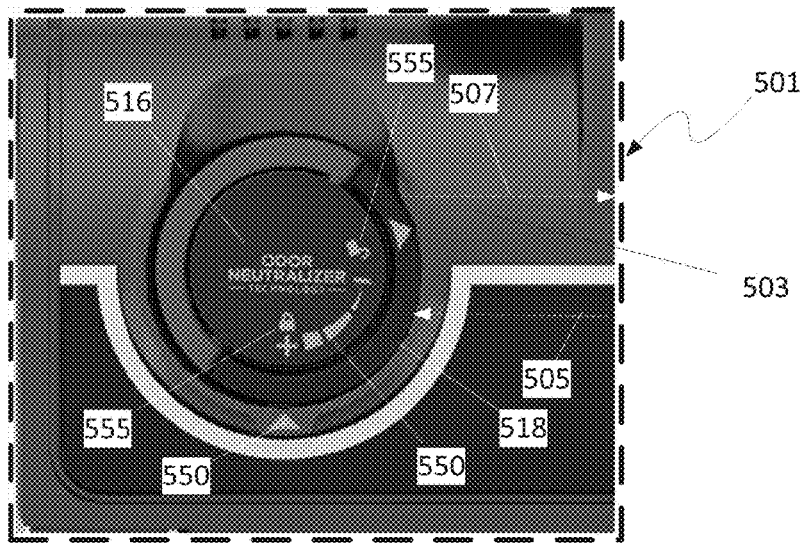
FIG. 5B shows an enlarged section of the odor control assembly of FIG. 5A.
Figure 6:
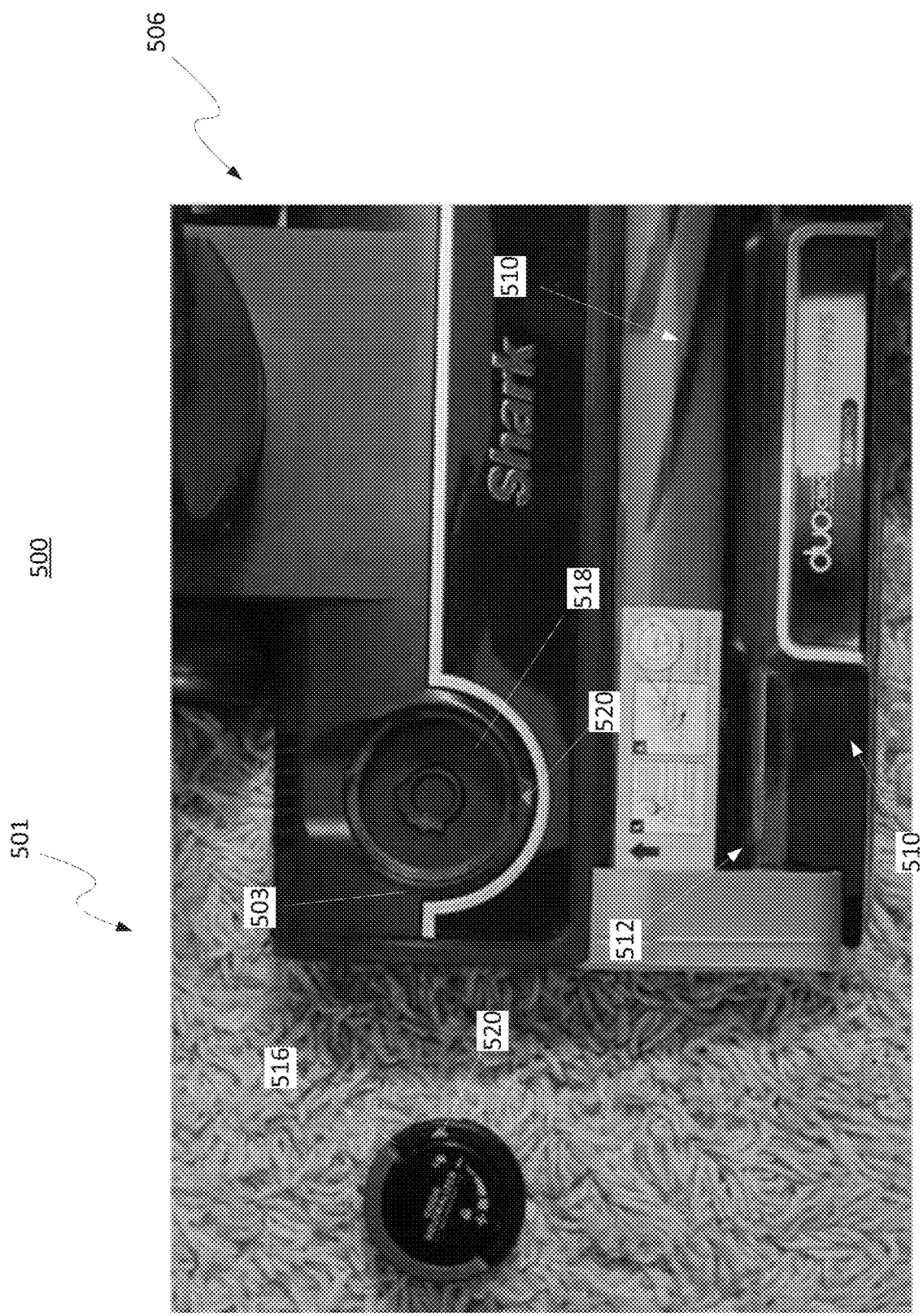
FIG. 6 shows an unassembled view of the nozzle and odor control assembly of FIG. 5A.

Turning now to FIGS. 5A-6, another example of a surface cleaning device 500 having an odor control assembly 501 consistent with the present disclosure is generally illustrated. In particular, the surface cleaning device 500 may include an upright section 504 coupled to a nozzle 506. The surface cleaning device 500 may include any of the features described herein which, for the sake of brevity, will generally not be repeated. The nozzle 506 may include one or more drive motors 508 which may be configured to rotate one or more agitators 510 (which may be at least partially disposed within one or more agitator chambers 512) as generally described herein. The nozzle 506 (e.g., the agitator chamber 512) may be fluidly coupled to the upright section 504 by way of a dirty air passageway 514.

The odor control assembly 501 may be configured to receive air (e.g., atmospheric air 505 communicated across the drive motor 508), to adjust the amount of fragrance and/or neutralizer dispensed by the odor dial assembly 516 into the fragranced air 507. The fragranced air 507 may flow into the dirty air passageway 514 and/or may be dispensed substantially directly to the atmosphere (e.g., may not flow through the filters associated with the surface cleaning device 500). The odor control assembly 501 may include at least one odor dial assembly 516 configured to be removable coupled to a tray 518 in the surface cleaning device 500. In particular, FIGS. 5A-5B generally illustrates the odor dial assembly 516 coupled to the tray 518 and FIG. 6 generally illustrates the odor dial assembly 516 removed from the tray 518. The tray 518 may be formed by the nozzle 506, for example, by the housing 503 of the nozzle 506.

The odor dial assembly 516 and/or the nozzle 506 (e.g., but not limited to, the housing 503 and/or the tray 518) may include one or more visual indicators 550 configured to represent the amount of fragrance being dispensed. For example, the visual indicators 550 may represent a minimum and/or off fragrance strength position, a maximum fragrance strength position, and/or any number of intermediate fragrance strength positions. In the illustrated example, the visual indicators 550 may include indicia which progressively increases in size corresponding to increasing fragrance strength positions.

Alternatively (or in addition), the visual indicator 550 may include a display (e.g., but not limited to, a Liquid crystal display (LCD), a Light-emitting diode (LED) backlit LCD, a Thin-film transistor (TFT) LCD, a Quantum dot (QLED) display, a Light-emitting diode (LED) display, an OLED display, an AMOLED display, and/or a Super AMOLED display) and/or one or more individual LEDs configured to represent the fragrance strength position of the odor dial assembly 516. Optionally, one or more sensors may be provided. In at least one example, an odor detection sensor may be included downstream of the odor dial assembly 516 to detect the amount of fragrance being dispensed. One or more sensors may also be provided to detect the remaining amount or level of the fragrance within the odor dial assembly 516. This information may be shown on any of the displays.

Alternatively (or in addition), the odor dial assembly 516 may include locking and/or unlocking indicia 555. The locking and/or unlocking indicia 555 may indicate to the user when the odor dial assembly 516 is in the insert/removal position and/or when the odor dial assembly 516 is in a locked or fixed position and cannot be removed from the tray 518.

Figure 7A:
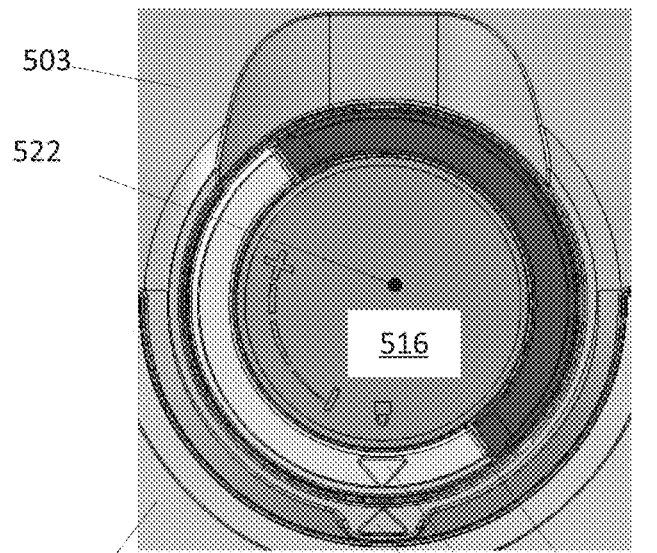
Figure 7B:
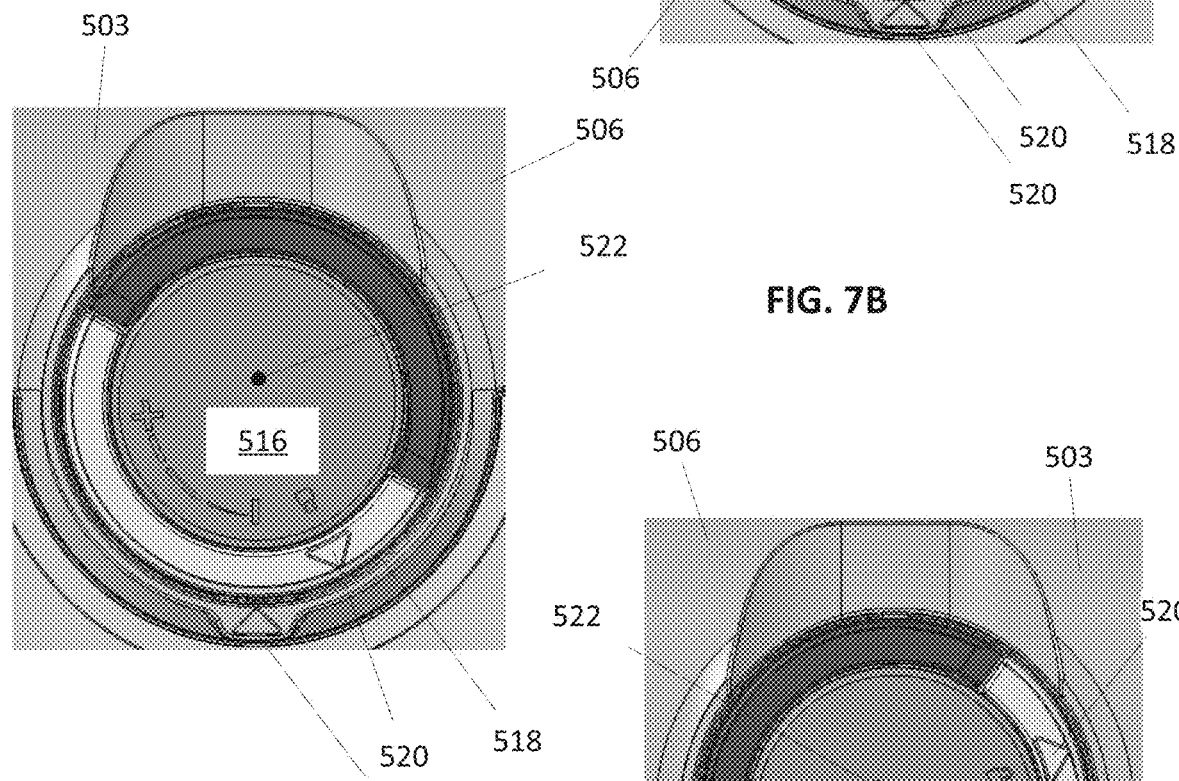
Figure 7C:
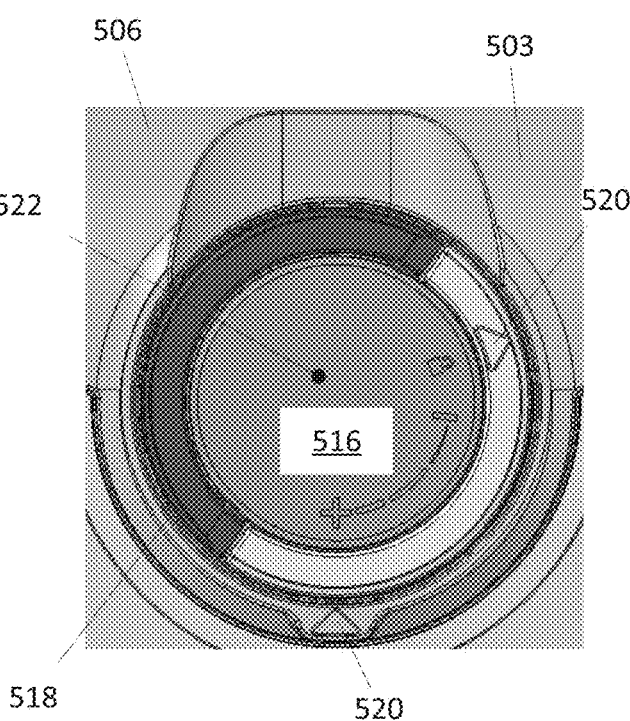
Figure 8:
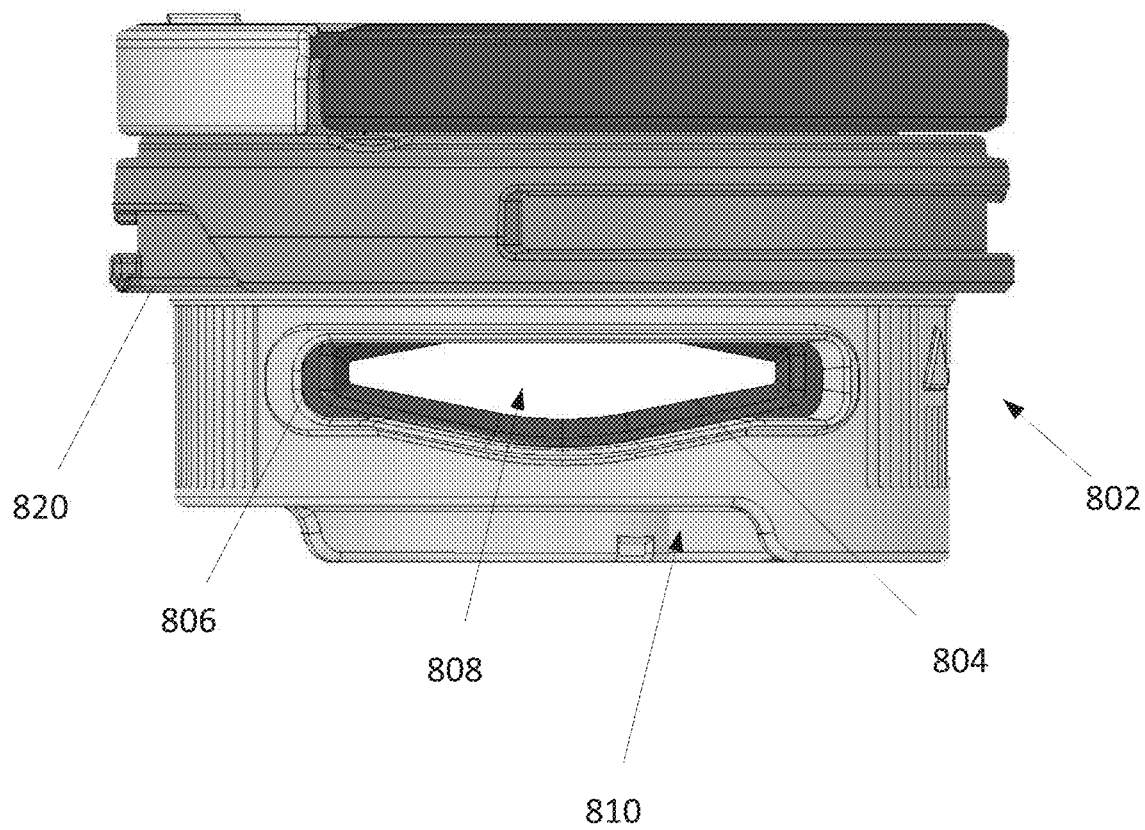
FIG. 8 shows one example of an odor dial assembly consistent with the present disclosure.

Turning to FIG. 7A, the user may insert and remove the odor dial assembly 516 into/out of the tray 518 by positioning the odor dial assembly 516 in a predetermined alignment with respect to the tray 518. The alignment may be facilitated by one or more alignment indicia 520 on the odor dial assembly 516 and/or the tray 518. The user may manipulate the odor control assembly 501 to adjust the amount of fragrance and/or neutralizer dispensed by the odor dial assembly 516, for example, by rotating the odor dial assembly 516 about a dial rotational axis 522. The odor dial assembly 516 may be rotated to a plurality of positions. For example, the odor dial assembly 516 may be rotated between the insertion/removal position (as generally illustrated in FIG. 7A) to a minimum strength position (as generally illustrated in FIG. 7B), a maximum strength position (as generally illustrated in FIG. 7C), and/or any number of intermediate positions. In the minimum strength position (as generally illustrated in FIG. 7B), the odor dial assembly 516 may be rotated counterclockwise around 27.5 degrees and will set the fragrance strength into the minimum setting. Optionally, the odor control assembly 501 may include one or more intermediate or medium strength settings (e.g., between the minimum and maximum settings), each of which may be correspond to about 27.5 degrees rotation past the previous position. In the maximum strength position, the odor dial assembly 516 may be rotated around 110 degrees and the user will set the fragrance strength to the maximum setting. In at least one example, the various positions may correspond to predefined positions. Alternatively, the odor dial assembly 516 may be infinitely variable. Of course, the present disclosure is not limited to the specific degrees of rotation unless specifically claimed as such. It should be appreciated that the order of the different positions relative to each are not limited to those shown. With reference to FIG. 8, one example of an odor dial assembly 516 consistent with the present disclosure is generally illustrated. The odor dial assembly 516 may include a dial body 802 configured to be removably secured to the tray 518 and configured to receive one or more fragrance members 804 (also referred to as a fragrance puck). The dial body 802 may have a generally circular cross-section and may be configured to generally form one or more seals with the nozzle 506 (e.g., the tray 518) and may optionally define a fragrance cavity 806 configured to receive and generally enclose the fragrance member 804. The dial body 802 and/or the fragrance members 804 may define one or more fragrance passageways 808 configured to allow air (e.g., atmospheric air 505 communicated across the drive motor 508) to flow over/past the fragrance members 804 to transfer fragrance particles into the air to form the fragranced air 507. The dial body 802 may also optionally include one or more air by-pass flow paths 810. As explained herein, the air by-pass flow paths 810 may be configured to ensure that a sufficient amount of air is able to flow across the drive motor 508 even when the odor control assembly 501 is in a minimum and/or off position, e.g., by providing an alternative airpath that substantially does not transfer any fragrance particles.

Figure 9:
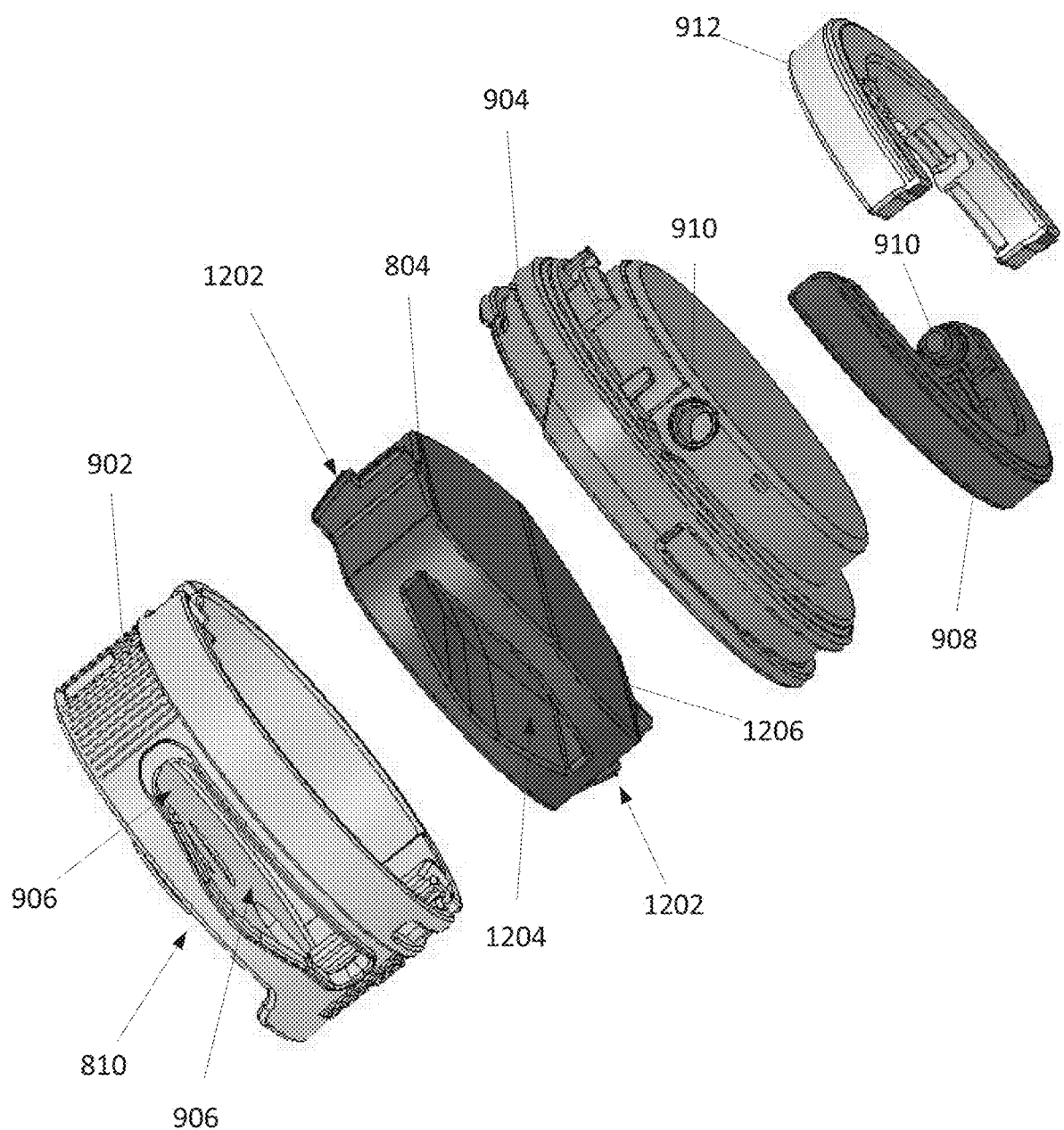
FIG. 9 shows an exploded view of one example of the odor dial assembly consistent with the present disclosure.

Turning now to FIG. 9, an exploded view of one example of the odor dial assembly 516 is generally illustrated. The dial body 802 may include a cartridge or base 902 and a cap or dial 904. The cartridge 902 and cap 904 may be configured to be removable coupled to each other to at least partially form the fragrance cavity 806 and the fragrance passageway 808. In the illustrated example, the cartridge 902 includes an entrance 906 and an exit (not visible in FIG. 9) to the fragrance passageway 808. Atmospheric air may flow through the entrance 906, across the fragrance member 804, and out of the exit. The cap 904 may optionally include one or more rotatable sections 908 that functions as a handle or D-ring to aid in insertion and removal of the odor dial assembly 516. The rotatable section 908 may be coupled to cap 904, for example, by way of one or more hinges 910 or the like. The cap 904 may also optionally include a fixed ring 912 secured to the cap 904.

Figure 10:
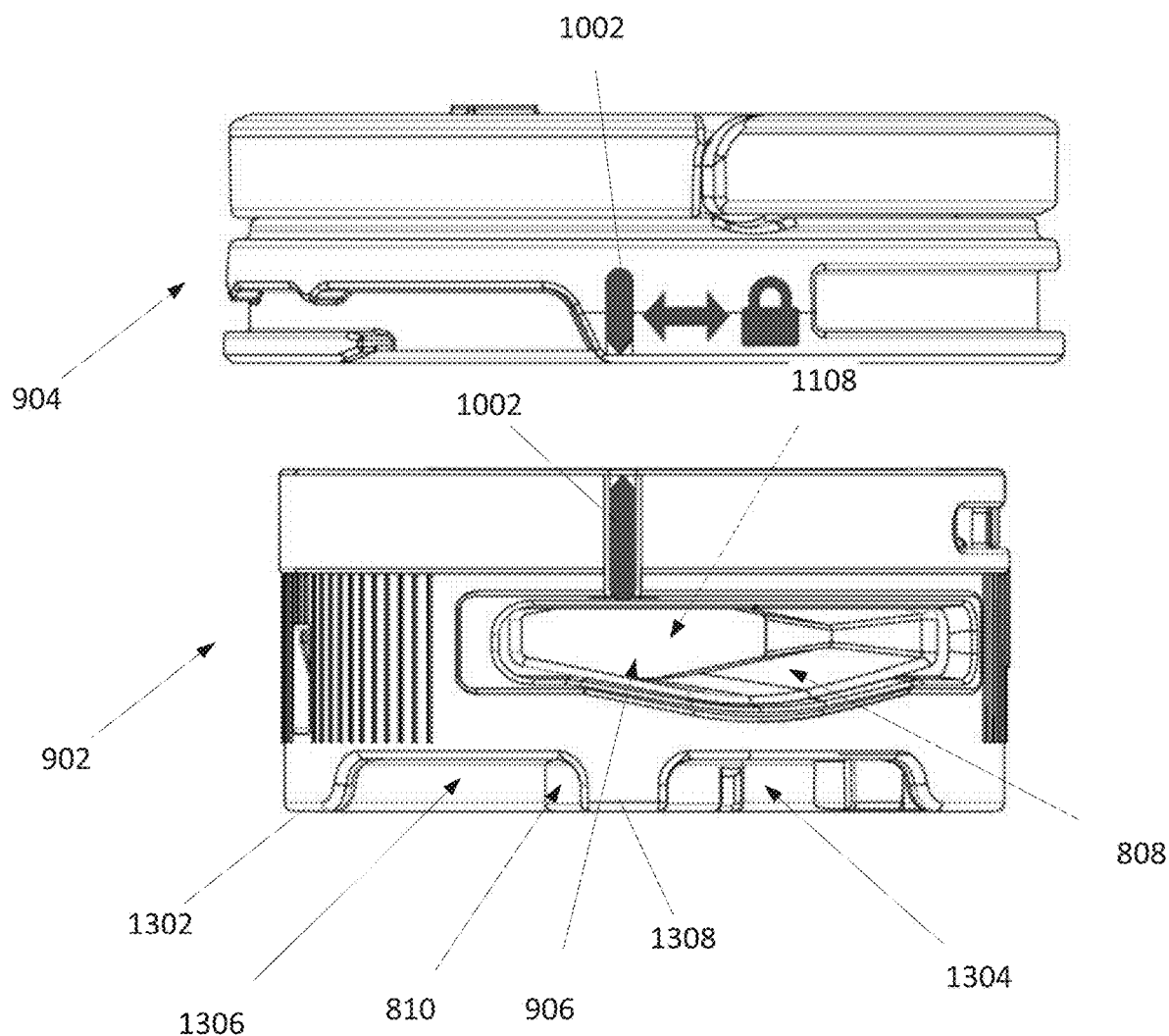
FIG. 10 shows another exploded view of the odor dial assembly consistent with the present disclosure.
Figure 11:
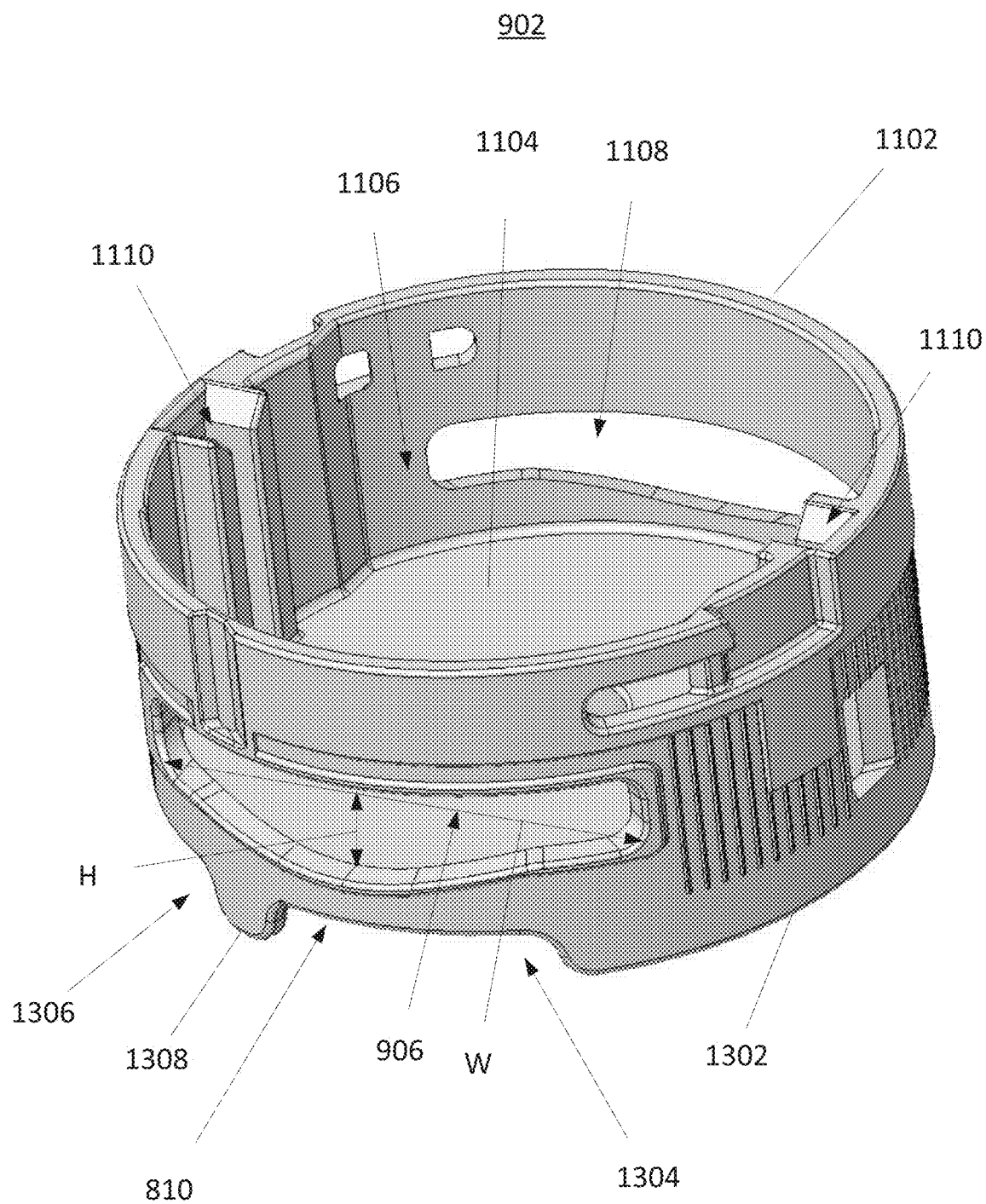

As noted above, the cartridge 902 and cap 904 may be configured to be removable coupled to each other to at least partially form the fragrance cavity 806 and the fragrance passageway 808. The cartridge 902 and cap 904 may be removably secured to each other in any manner known to those skilled in the art such as, but not limited to, threaded connections, tabs, detents, clips, or the like. The coupling of the cartridge 902 and cap 904 may be facilitated by one or more cap alignment indicia 1002, one example of which is generally illustrated in FIG. 10.

One benefit of the removable connection between the cartridge 902 and cap 904 is that is allows for the replacement of the cartridge 902 and the fragrance member 804 to be accomplished without the user having to touch the fragrance member 804 and without having to replace the entire odor dial assembly 516. In particular, when the user desires to replace the fragrance member 804, the user may purchase the cartridge 902 which is preloaded with the fragrance member 804. The user may then disconnect the cartridge 902 (which includes the fragrance member 804) from the cap 902 and then connect a new cartridge 902 (in which the fragrance member 804 is preloaded therein) to the existing cap 902.

Figure 11:
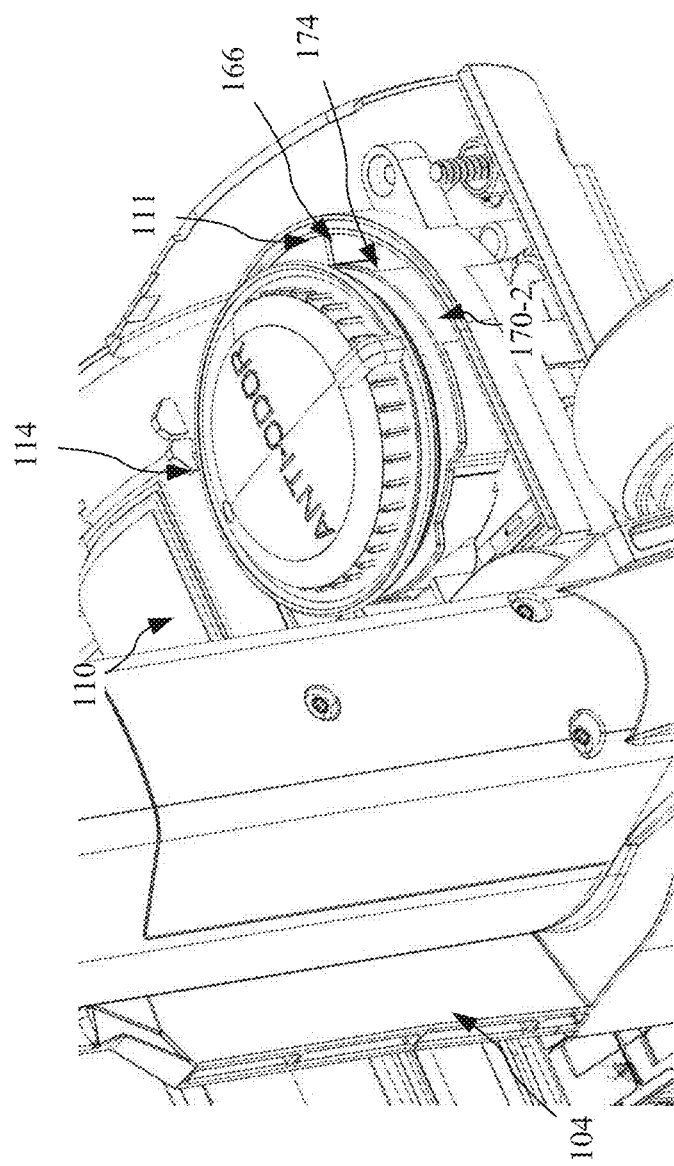
FIG. 11 shows one example of a cartridge consistent with the present disclosure.

Turning now to FIG. 11, one example of the cartridge 902 is generally illustrated. The cartridge 902 may include one or more sidewall 1102, for example, extending upwardly from a base 1104. The sidewall 1102 (and optionally the base 1104) may define a puck chamber 1106 configured to receive the fragrance member 804. The puck chamber 1106 may be the same as the fragrance cavity 806 or may define a portion of the fragrance cavity 806. The sidewall 1102 may also at least partially define the entrance 906 and exit 1108 to the fragrance passageway 808. In the illustrated example, the entrance 906 and exit 1108 to the fragrance passageway 808 are generally aligned 180 degrees opposite each other; however, it should be appreciated that the entrance 906 and exit 1108 may be aligned at any other angle.

Figure 12:
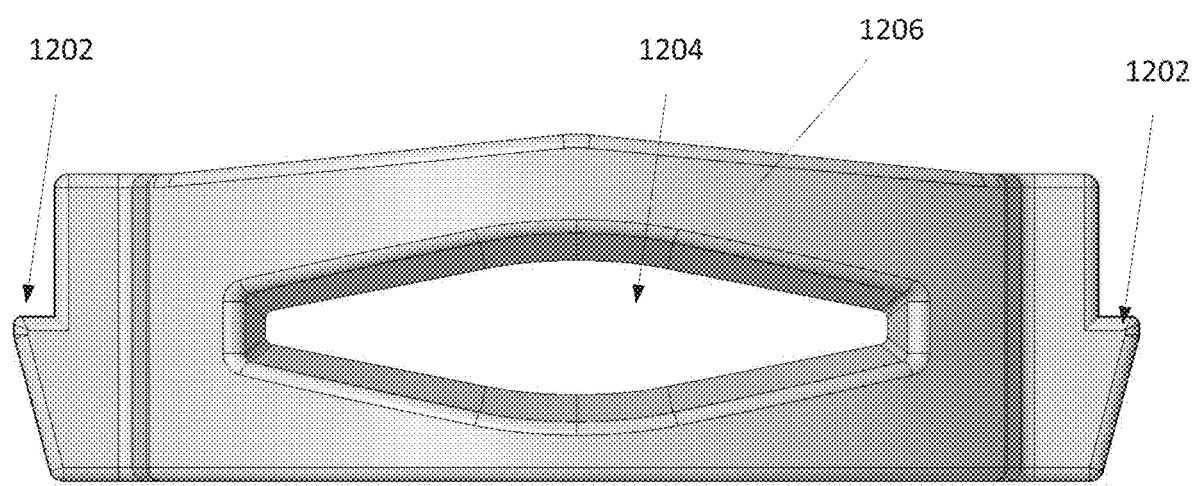
FIG. 12 shows one example of a fragrance member with the present disclosure.
Figure 13A:
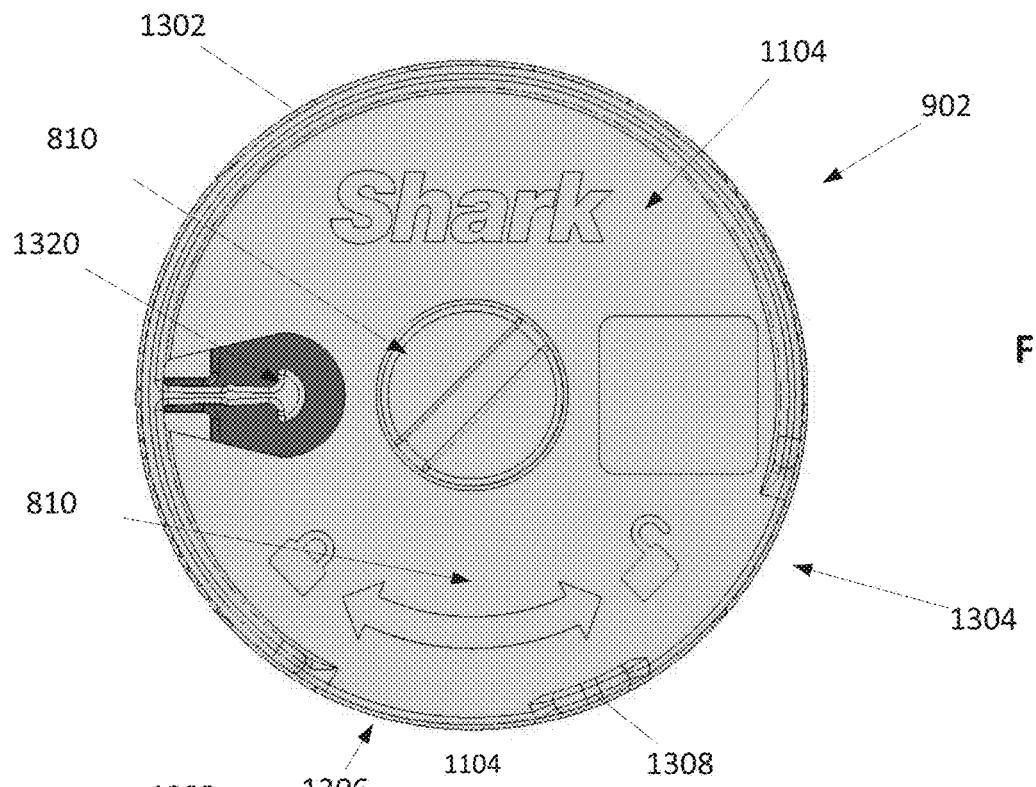
FIG. 13A shows a bottom view of a cartridge consistent with the present disclosure.
Figure 13B:
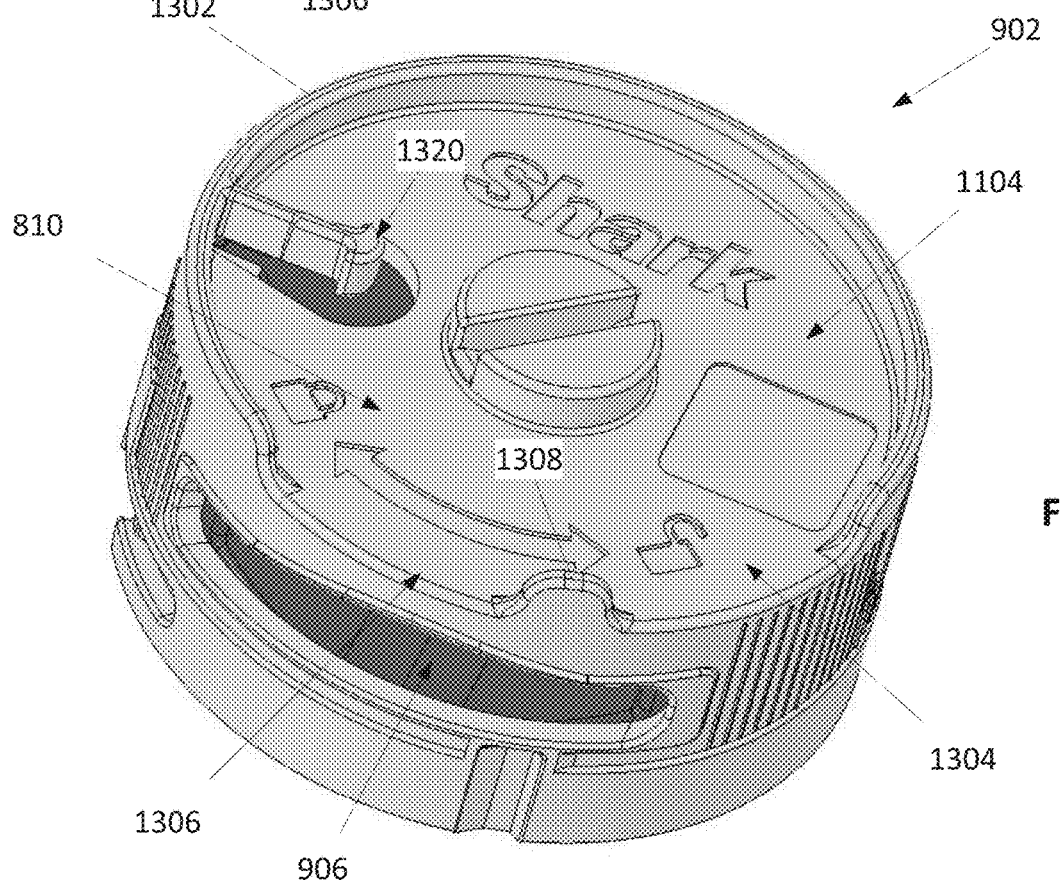
FIG. 13B shows a perspective view of a cartridge consistent with the present disclosure.

The sidewall 1102 may optionally include one or more puck alignment features 1110. The puck alignment features 1110 are configured to align the fragrance member 804 relative to the entrance 906 and exit 1108. In the illustrated example, the puck alignment features 1110 include grooves configured to receive corresponding tabs 1202 (FIG. 12) of the fragrance member 804 and to align the passageway 1204 extending through the body 1206 of the fragrance member 804 with the entrance 906 and exit 1108. The entrance 906, exit 1108, and the passageway 1204 may collectively define (at least in part) the fragrance passageway 808. The height H of the entrance 906 and/or exit 1108 may vary across the width W. In particular, the height H may be less proximate one or more of the ends of the width and larger in-between (e.g., the middle). The varying height H may facilitate the adjustment of the airflow through the fragrance passageway 808 as the odor dial assembly 516 is rotated. The passageway 1204 extending through the body 1206 of the fragrance member 804 may include a through hole aligned with the entrance and the exit of the fragrance air path. The through hole may define a passage through the fragrance member 804 which is surrounded by the fragrance member 804 and having an entrance and an outlet. The through hole may also have a cross-section that corresponds to the cross-section of the entrance 906, exit 1108. A benefit of the through hole in the fragrance member 804 is that it increases the surface area available to transfer fragrance particles into the air flowing through the fragrance member 804.

With reference to FIGS. 10, 11, and 13A-13B, one example of the air by-pass flow path 810 is generally illustrated. In the illustrated example, the cartridge 902 may include a one or more by-pass sidewalls or skirts 1302, e.g., extending downwardly from the base 1104. The by-pass sidewall 1302 may extend generally around at least a portion of the periphery or perimeter of the base 1104 of the cartridge 902, though this is not a limitation of the present disclosure unless specifically claimed as such. For example, the by-pass sidewall 1302 may extend generally around only a portion of the bottom of the cartridge 902. The cartridge 902 may include one or more by-pass entrances 1304 and by-pass exits 1306 to the air by-pass flow path 810. The by-pass entrances 1304 and by-pass exits 1306 may be separated by one or more divider walls 1308. The by-pass sidewall 1302 and the divider walls 1308 may be configured to generally rotate against and generally seal with the tray 518, for example, the bottom surface or base of the tray 518. The by-pass sidewall 1302, the divider walls 1308, the base 1104 (and optionally the tray 518) may at least partially collectively define the air by-pass flow path 810 through the odor dial assembly 516. It should be appreciated that the cartridge 902 may optionally include a wall extending from the distal ends of the by-pass sidewall 1302 and the divider walls 1308 that defines the opposite side of the air by-pass flow path 810. As explained herein, rotation of the odor dial assembly 516 (e.g., the cartridge 902) may selectively fluidly couple the by-pass entrance 1304 and/or by-pass exit 1306 to the air by-pass flow path 810, thereby adjusting the airflow rate through the air by-pass flow path 810.

The bottom surface of the cartridge 902 may optionally include a slot or the like that allows for easy disconnection of the cartridge 902 from the cap 904. This may allow a user to remove the cartridge 902 without having to touch the cartridge 902.

Figure 14A:
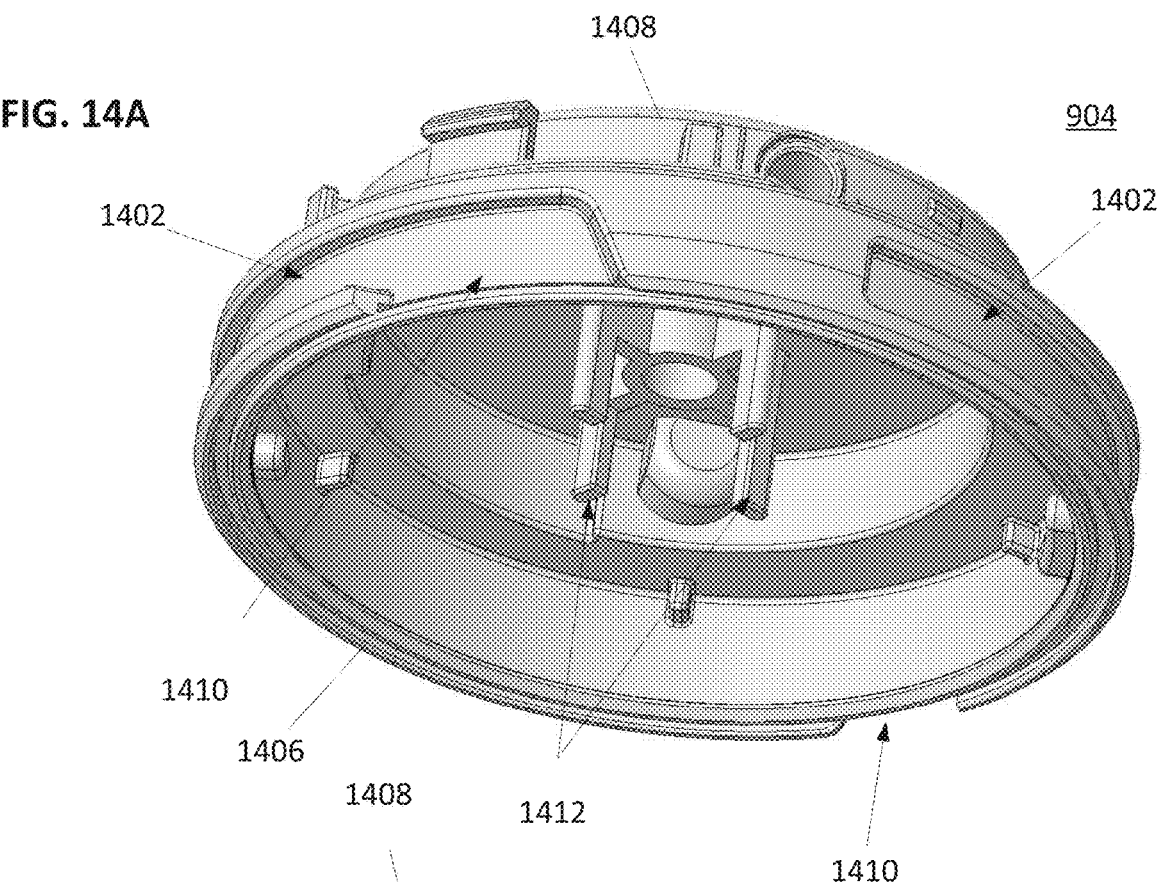
FIG. 14A shows a perspective view of a cap consistent with the present disclosure.
Figure 14B:
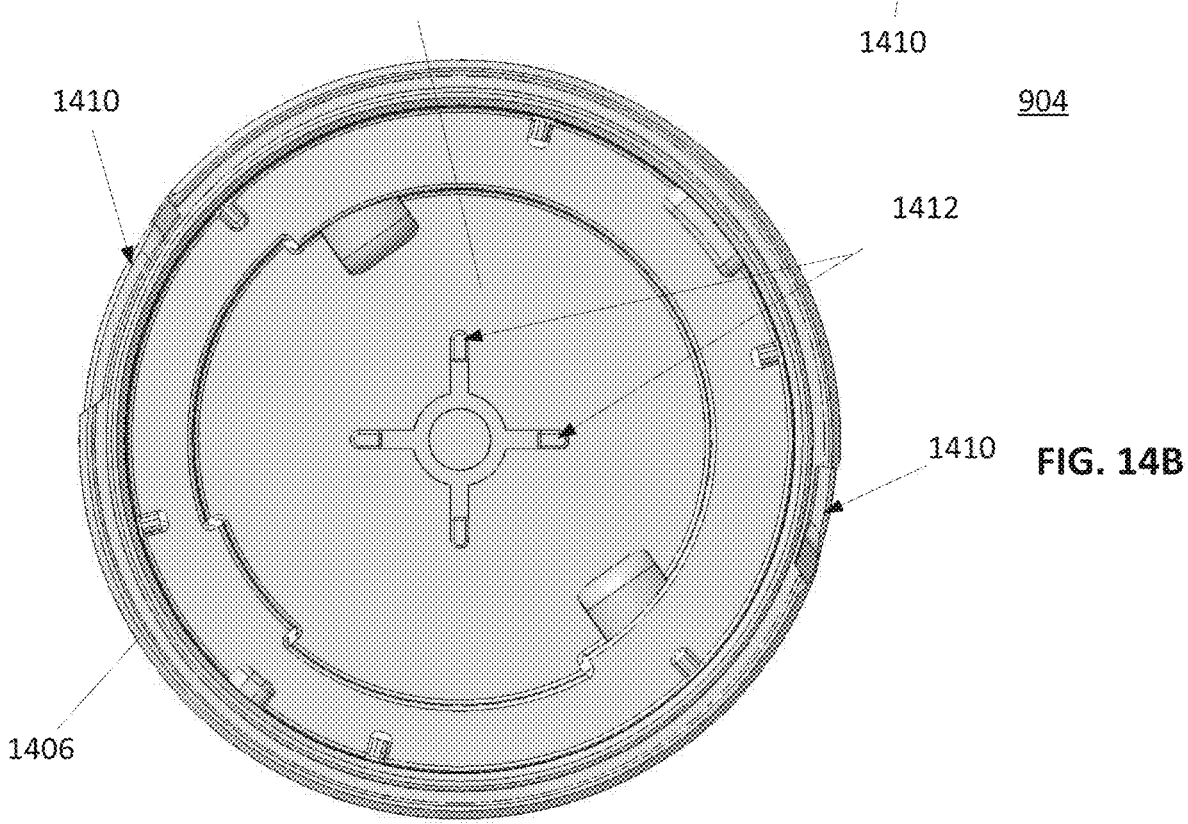
FIG. 14B shows a bottom view of a cap consistent with the present disclosure.

Turning now to FIGS. 14A-14B, one example of the cap 904 is generally illustrated. As noted herein, the cap 904 may be configured to be removably coupled to the cartridge 902 in any manner known to those skilled in the art. The cap 904 may include one or more locking grooves 1402 configured to engage with one or more locking protrusions or tabs 1502 (see, e.g., FIG. 15) associated with the tray 518. The locking grooves 1402 and locking protrusions 1502 may be configured to urge the odor dial assembly 516 into engagement with the nozzle 506 (e.g., the tray 518) to generally seal the odor dial assembly 516 as explained herein, while also allowing the odor dial assembly 516 to rotate. In at least one example, at least a portion of the locking grooves 1402 and locking protrusions 1502 may have a ramped profile.

The locking grooves 1402 may be formed in a sidewall 1406, for example, that generally extends around at least a portion of the perimeter or periphery of the top surface 1408 of the cap 904. Each locking grooves 1402 may include an entrance 1410. The entrances 1410 may be arranged asymmetrically about the cap 904 such that the entrances 1410 only align with the locking protrusions 1502 in a single orientation, thereby preventing the odor dial assembly 516 from being inadvertently inserted into the tray 518 incorrectly. The entrances 1410 may also have different sizes and/or shapes.

The cap 904 may optionally include one or more raised ribs 1412. The ribs 1410 may extend downwardly from the top surface 1408 generally into the fragrance cavity 806 and/or the puck chamber 1106 and are configured to generally limit movement of the fragrance member 804, prevent the fragrance member 804 from being inserted upside down, and/or prevent the cartridge 902 from being inserted upside down into the cap 904.

Figure 15:
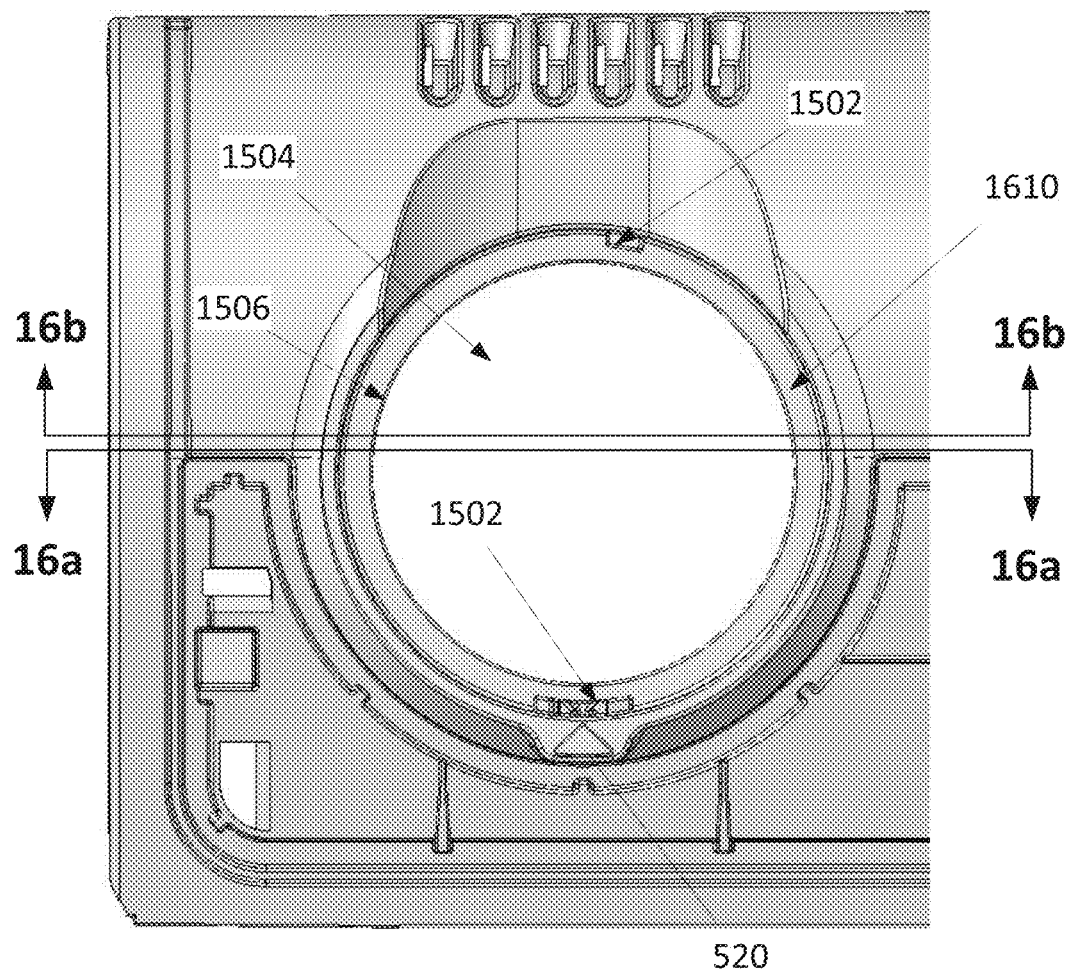
FIG. 15 shows a top view of a tray consistent with the present disclosure.
Figure 16A:
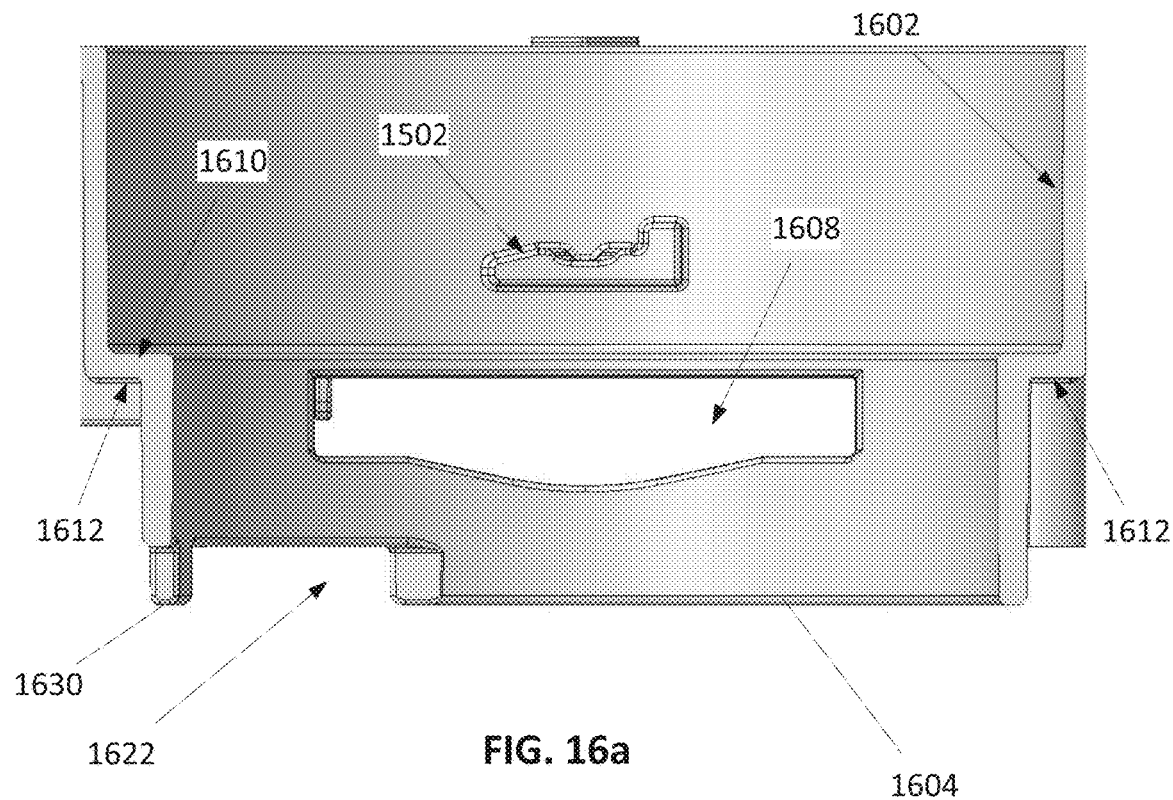
FIGS. 16A and 16B show cross-sectional views of the tray of FIG. 15 consistent with the present disclosure.
Figure 16B:
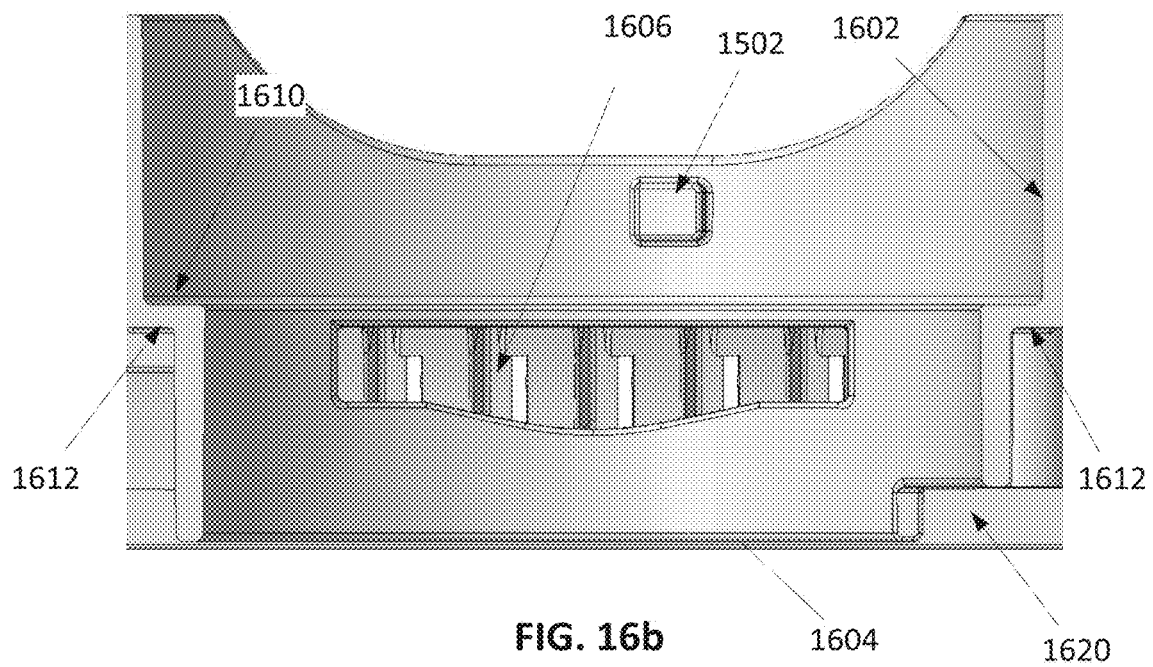
Figure 18:
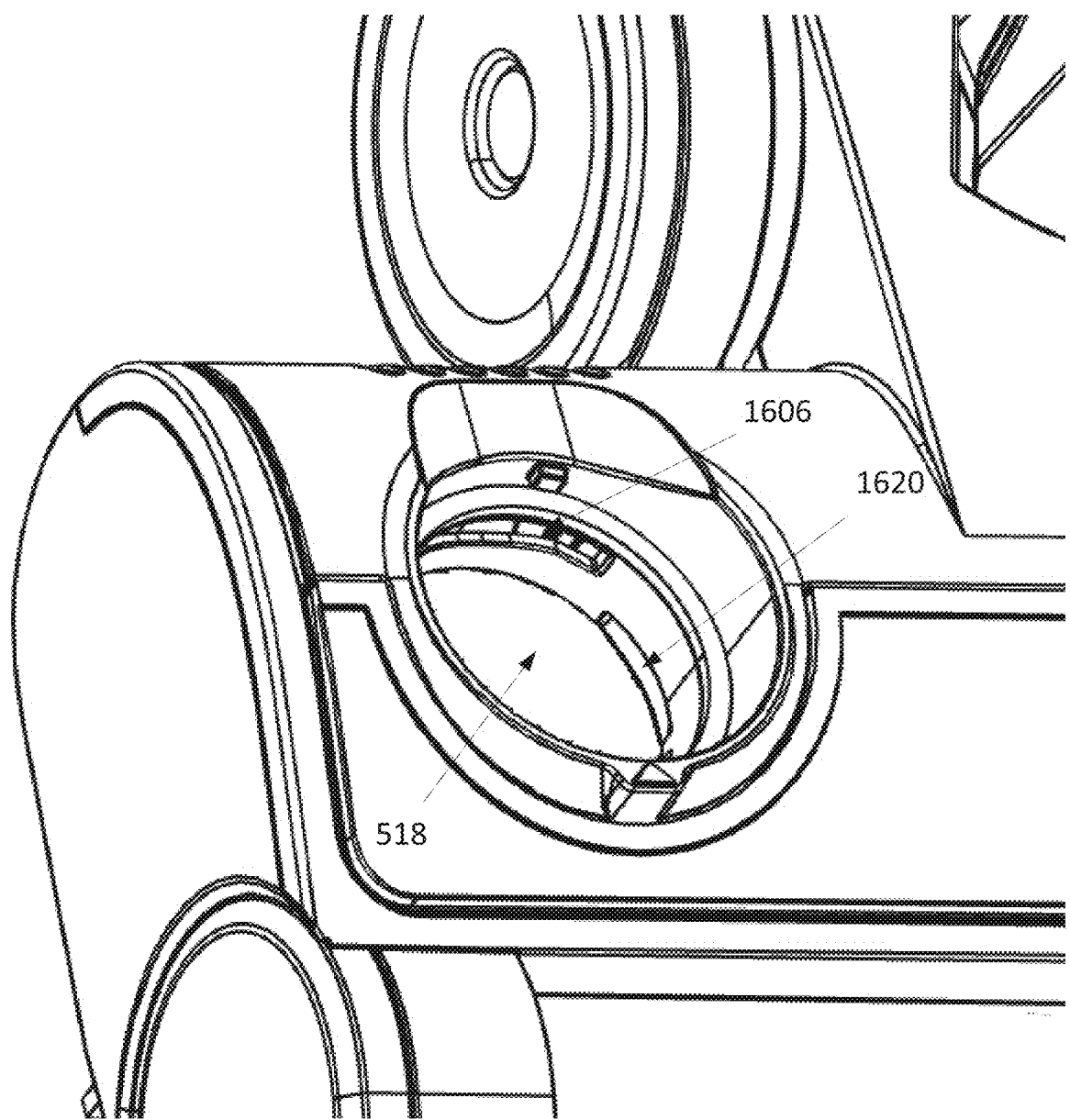
FIGS. 18, 19, and 20 show various perspective view of a tray consistent with the present disclosure.
Figure 19:
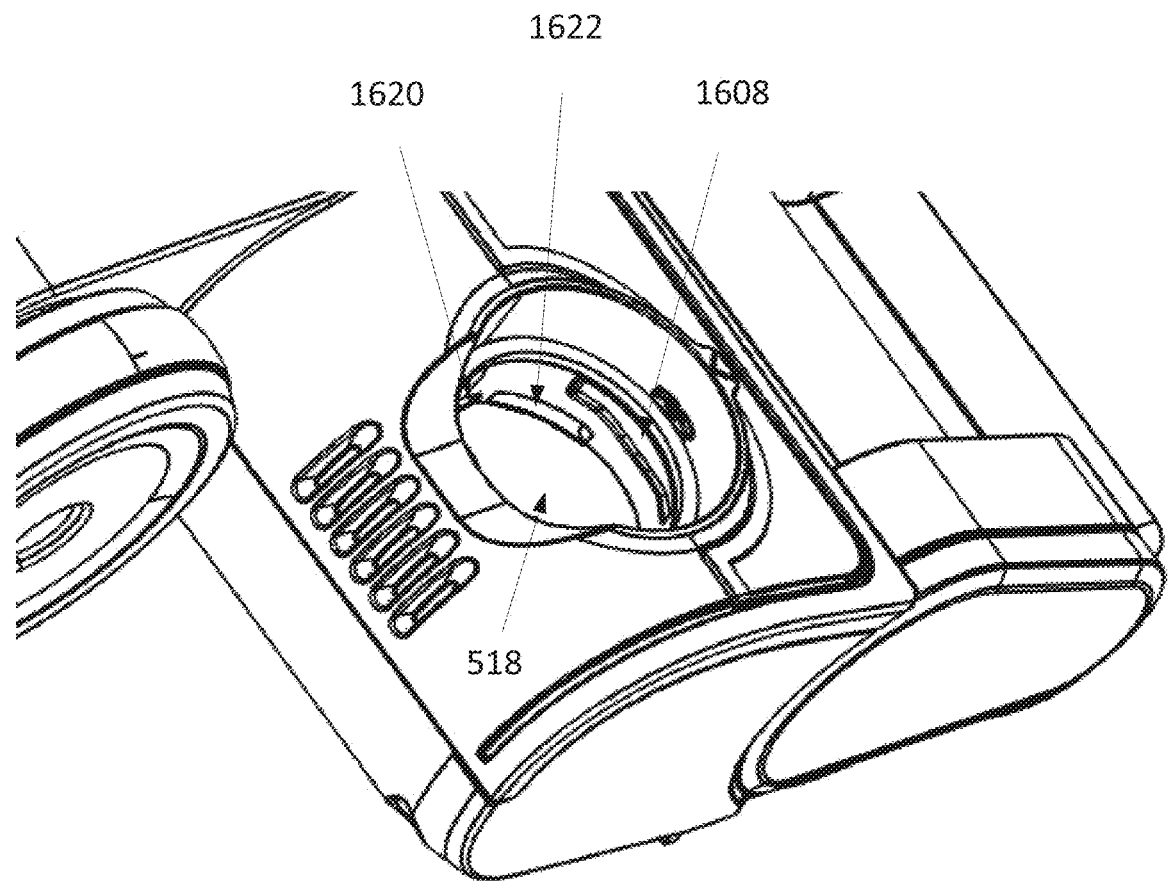
Figure 20:
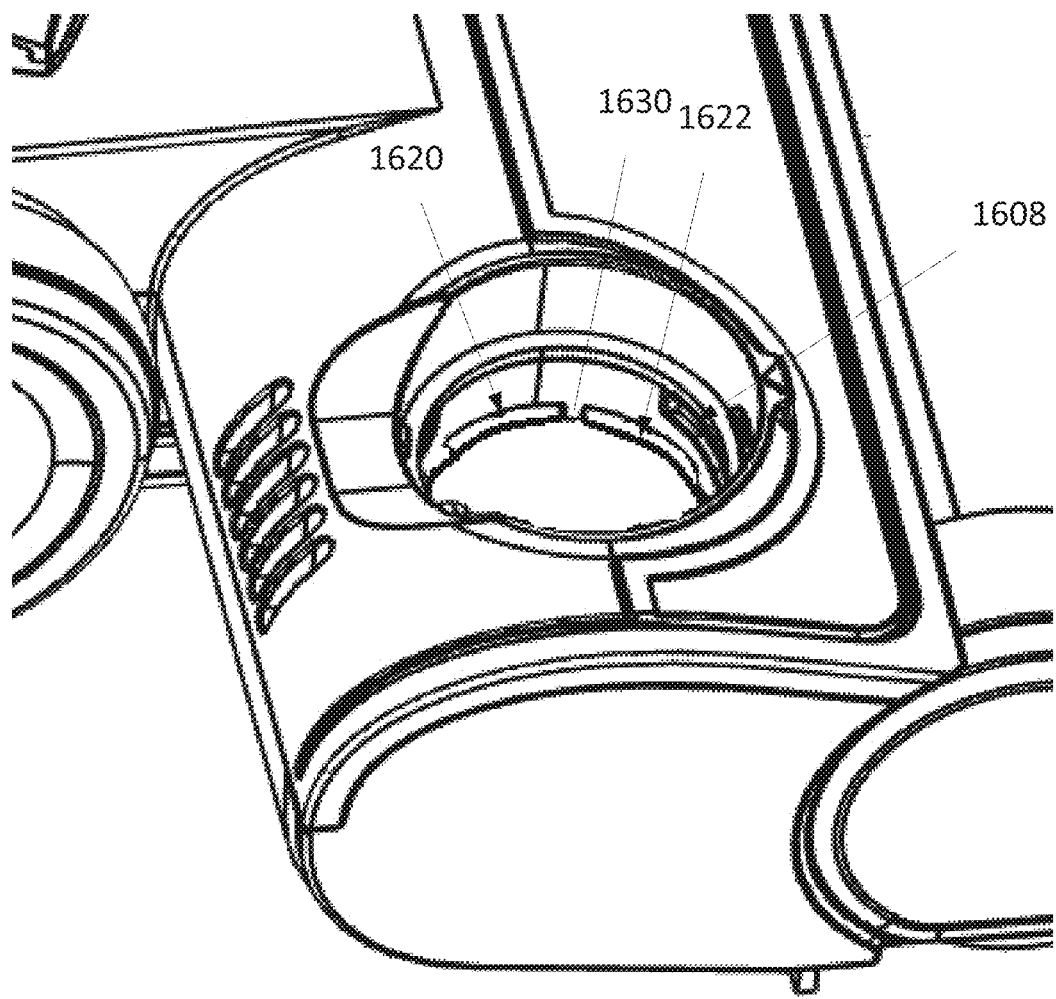

Turning to FIG. 15, one example of the tray 518 (which also may be referred to as an odor base) is generally illustrated. The tray 518 may be formed, at least in part, by the nozzle 506, for example, by the housing 503 of the nozzle 506. The tray 518 may include a recess or the like 1504 having an opening 1506 configured to at least partially receive the odor dial assembly 516. With reference to FIGS. 16A-16B, the tray 518 may include one or more sidewalls 1602 and optionally a base 1604. The tray 518 may include an odor inlet 1606 and an odor outlet 1608. The odor inlet 1606 may be configured to fluidly couple the tray 518 to the motor conduit 142 (see, e.g., FIG. 17), which itself may include an end fluidly coupled to the motor cavity 140 and/or drive motor 134 as generally described herein. The odor inlet 1606 and/or odor outlet 1608 (see also FIGS. 18-20) may have a shape substantially corresponding to the shape of the entrance 906 and exit 1108 of the odor dial assembly 516 (e.g., in the cartridge 902).

As explained herein, the odor dial assembly 516 is configured to be rotated to adjust the alignment of the entrance 906 and exit 1108 of the odor dial assembly 516 relative to the odor inlet 1606 and/or odor outlet 1608 of the tray 518 to thereby adjust the flowrate through the odor dial assembly 516 (and therefore the amount of fragrance introduced into the air). As the alignment of the odor inlet 1606 and/or odor outlet 1608 of the odor dial assembly 516 relative to the entrance 906 and exit 1108 of the tray 518 increases (i.e., they become more aligned), the flowrate through the odor dial assembly 516 increases. Conversely, if the odor dial assembly 516 is rotated such that the entrance 906 and exit 1108 of the odor dial assembly 516 do not align with the odor inlet 1606 and/or odor outlet 1608 of the tray 518, then the flowrate through the odor dial assembly 516 may be minimized and/or generally prevented. For example, the sidewall 1102 of the cartridge 902 may block all or a portion of the odor inlet 1606 and/or odor outlet 1608 of the tray 518.

The tray 518 may also optionally include one or more by-pass inlets 1620 and by-pass outlets 1622 (see also FIGS. 16A-16B and 18-20) which fluidly couple the tray 518 to the bypass path 174 as generally described herein. The by-pass inlet 1620 may be configured to fluidly couple the tray 518 to the bypass path 174, and the by-pass outlet 1622 may be configured to fluidly couple the tray 518 dirty air passageway 514. The by-pass inlet 1620 and/or by-pass outlet 1622 may have a shape substantially corresponding to the shape of the entrance 1304 and exit 1306 of the odor dial assembly 516 (e.g., in the cartridge 902). The by-pass inlet 1620 and/or by-pass outlet 1622 may be separated by a by-pass divider wall 1630.

As explained herein, the odor dial assembly 516 is configured to be rotated to adjust the alignment of the by-pass entrance 1304 and by-pass exit 1306 of the odor dial assembly 516 relative to the by-pass inlet 1620 and/or by-pass outlet 1622 of the tray 518 to thereby adjust the flowrate of the air by-pass 810 through and/or under the odor dial assembly 516. As the alignment of the by-pass entrance 1304 and by-pass exit 1306 of the odor dial assembly 516 relative to the by-pass inlet 1620 and/or by-pass outlet 1622 of the tray 518 increases (i.e., they become more aligned), the flowrate through/under the odor dial assembly 516 increases. Conversely, if the odor dial assembly 516 is rotated such that the by-pass entrance 1304 and by-pass exit 1306 of the odor dial assembly 516 do not align with the by-pass inlet 1620 and/or by-pass outlet 1622 of the tray 518, then the by-pass flowrate 810 through the odor dial assembly 516 may be minimized and/or generally prevented. For example, the by-pass sidewall 1302 of the cartridge 902 may block all or a portion of the by-pass inlet 1620 and/or by-pass outlet 1622 of the tray 518.

The tray 518 may also optionally include one or more seals or sealing surfaces 1610 (e.g., best seen in FIGS. 16A-16B) configured to sealingly engage with the odor dial assembly 516. The seal 1610 may include a resiliently deformable material such as, but not limited to, an O-ring or the like. In the illustrated example, the seal 1610 may disposed on a ledge 1612 formed in/on the sidewall 1602 and may be configured to sealingly engage with a corresponding ledge 820 (FIG. 8) formed by the cap 904 when the odor dial assembly 516 is received in the tray 518. Of course, this arrangement may be reversed, and other seals are within the scope of the present disclosure.

Figure 17:
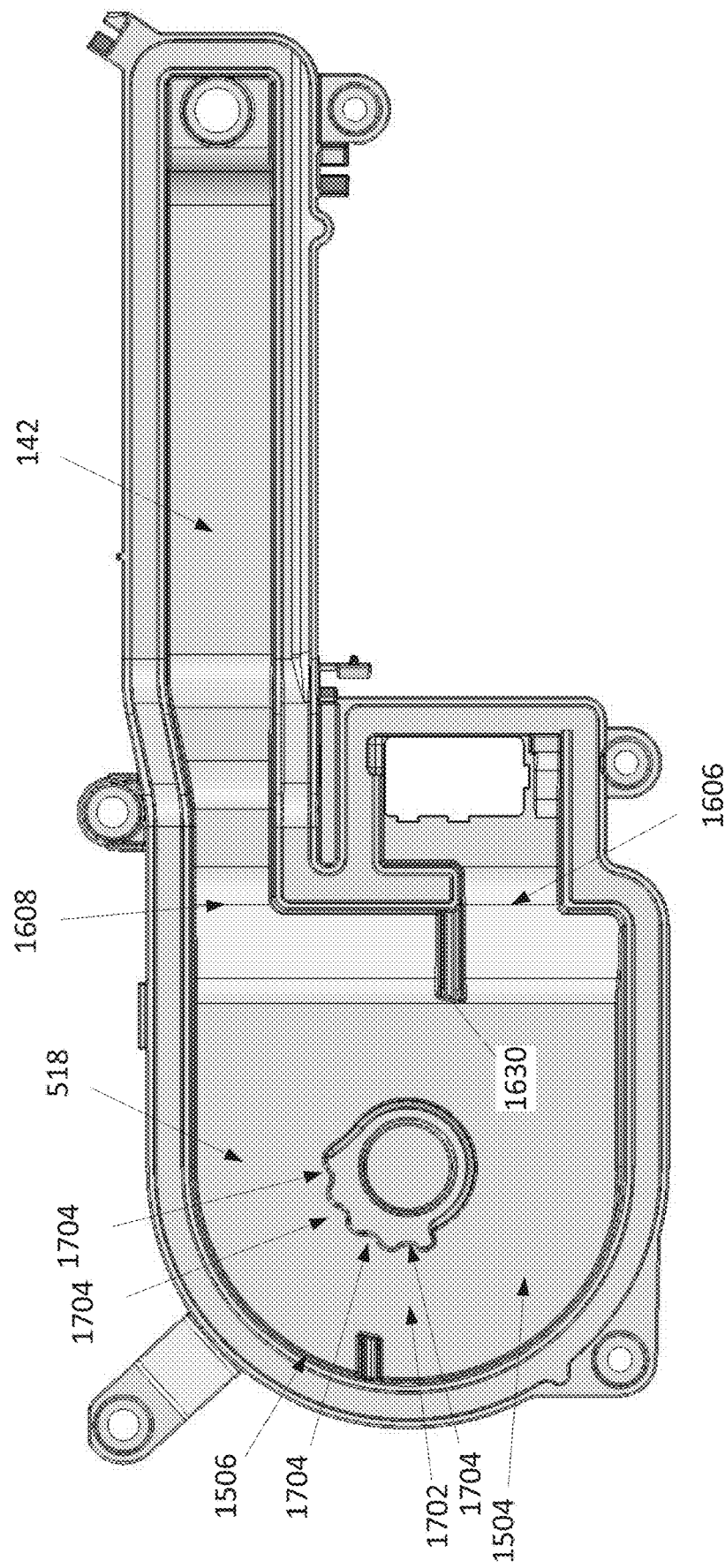
FIG. 17 shows a top view of a tray and a motor conduit consistent with the present disclosure.

With reference to FIG. 17, the tray 518 may also optionally include a cam 1702. The cam 1702 may include a plurality of detent grooves 1704 which correspond to the plurality of predefined positions of the odor dial assembly 516 (e.g., but not limited to, the insertion/removal position, the minimum strength position, one or more intermediate strength positions, and/or a maximum strength position). In particular, the odor dial assembly 516 may include a one or more resilient detent levers 1320 (best seen in FIGS. 13A-13B) configured to engage the detent grooves 1704. The interaction between the detent grooves 1704 and the detent levers 1320 allows the user to easily identify the different strength positions of the odor dial assembly 516 relative to the tray 518. In the illustrated example, the cam 1702 may be located on the base 1604 of the tray 518 and the resilient detent levers 1320 may be located on the base 1104 of the odor dial assembly 516, though this is not a limitation of the present disclosure unless specifically claimed as such and the cam 1702 and resilient detent levers 1320 may be located anywhere on the tray 518 and odor dial assembly 516.

Figure 21:
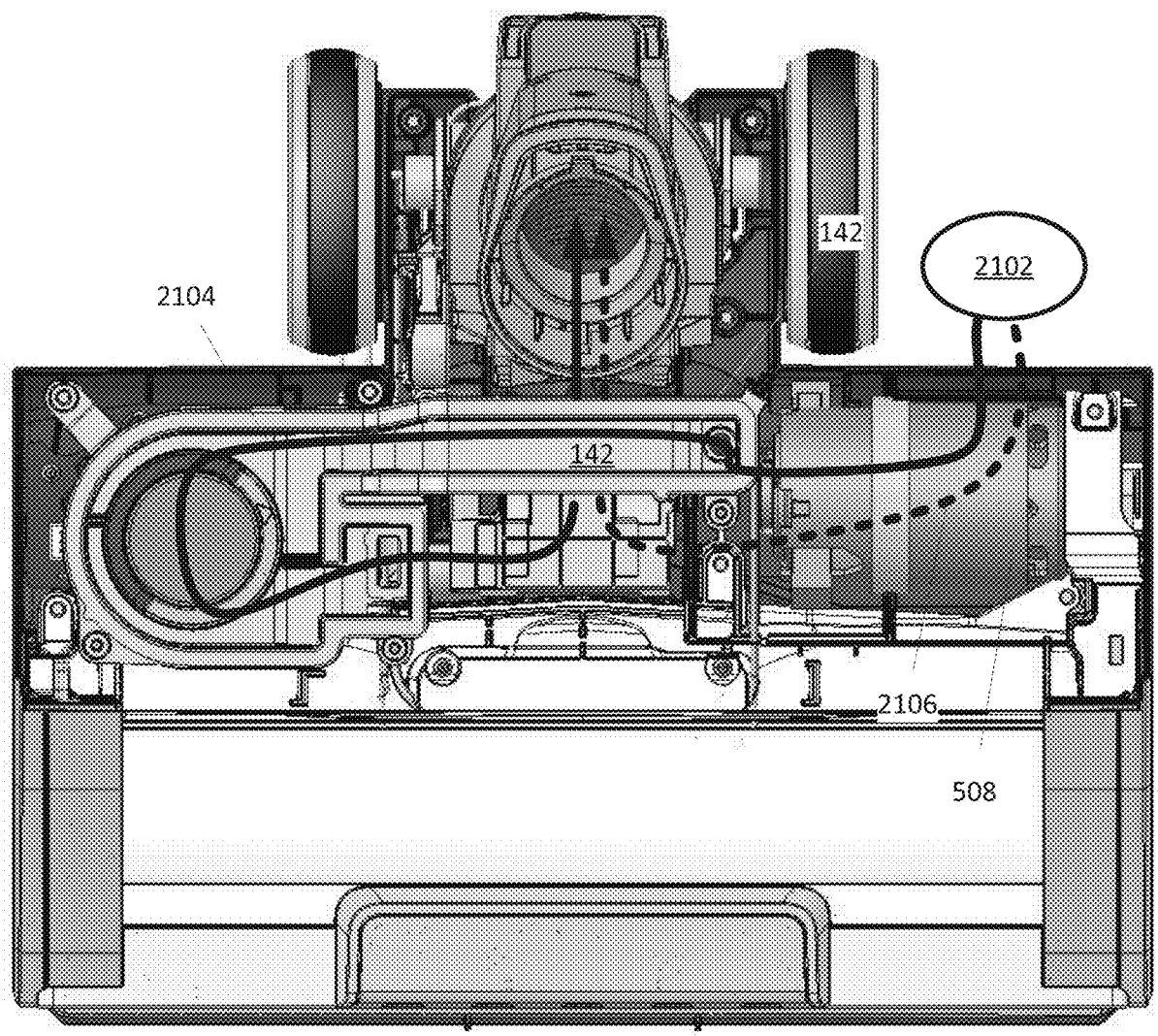
FIG. 21 shows one example generally illustrating the airflows paths through odor dial assembly and the tray with the present disclosure.

Turning to FIG. 21, one example generally illustrating the airflows paths through odor dial assembly 516 and the tray 518 is generally illustrated. The ambient (atmospheric) air 2102 may flow across the drive motor 508 where heat from the drive motor 508 may be transferred into the air. The heated air 2104 may selectively flow through the motor conduit 142 to the odor inlet 1606 and/or odor outlet 1608 of the tray 518 and the entrance 906 and exit 1108 of the odor dial assembly 516 as generally described herein. Optionally, a portion of the heated air 2104 may selectively flow through the air by-pass flow path 810 to the by-pass inlet 1620 and/or by-pass outlet 1622 of the tray 518 and the by-pass entrance 1304 and by-pass exit 1306 of the odor dial assembly 516 as generally described herein. The nozzle 506 may optionally include a dedicated motor cooling airpath 2106 which may bypass the odor control assembly 501.

Figure 22:
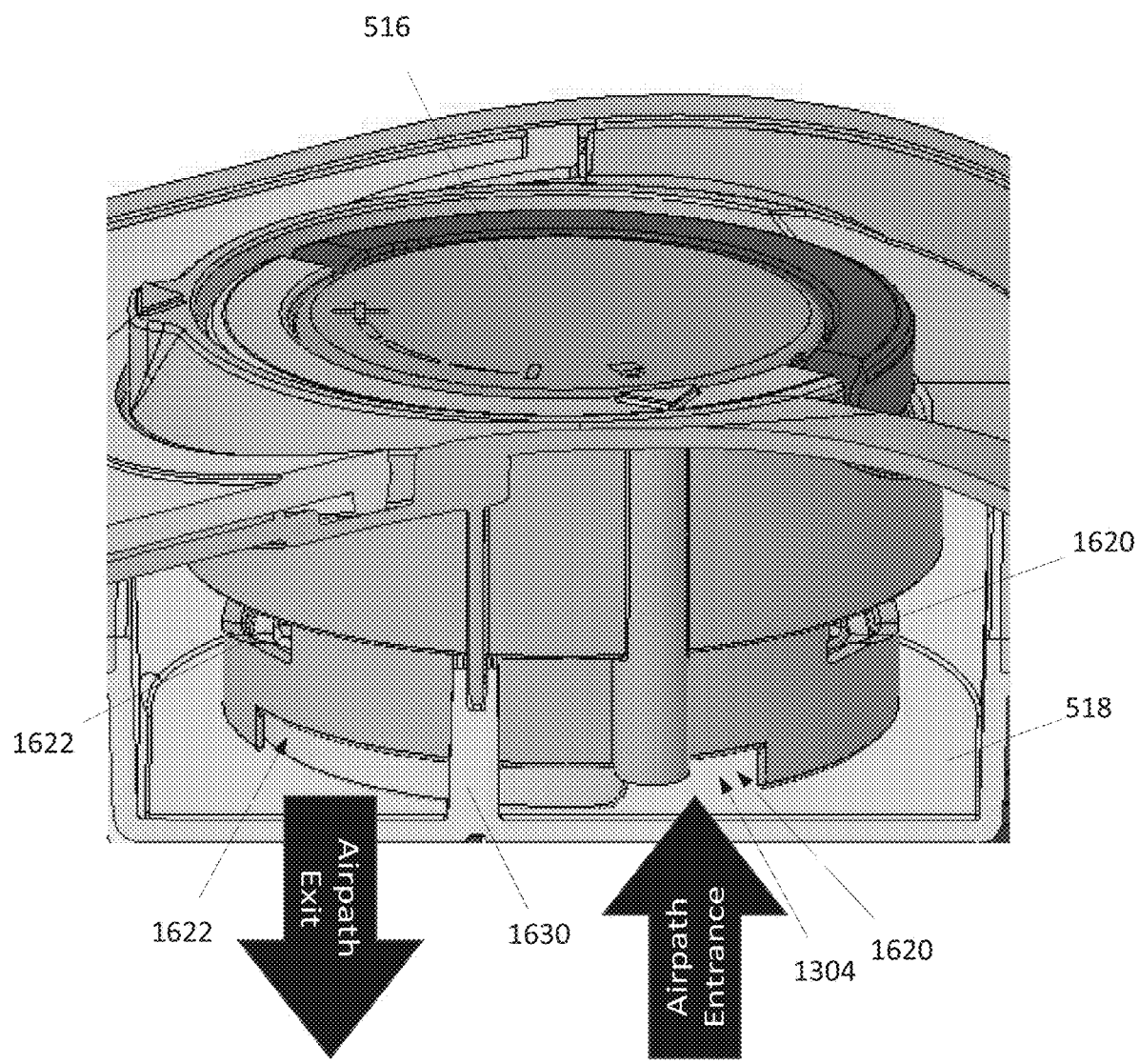
FIGS. 22, 23, and 24 show the odor dial assembly in a maximum strength position consistent with the present disclosure.
Figure 23:
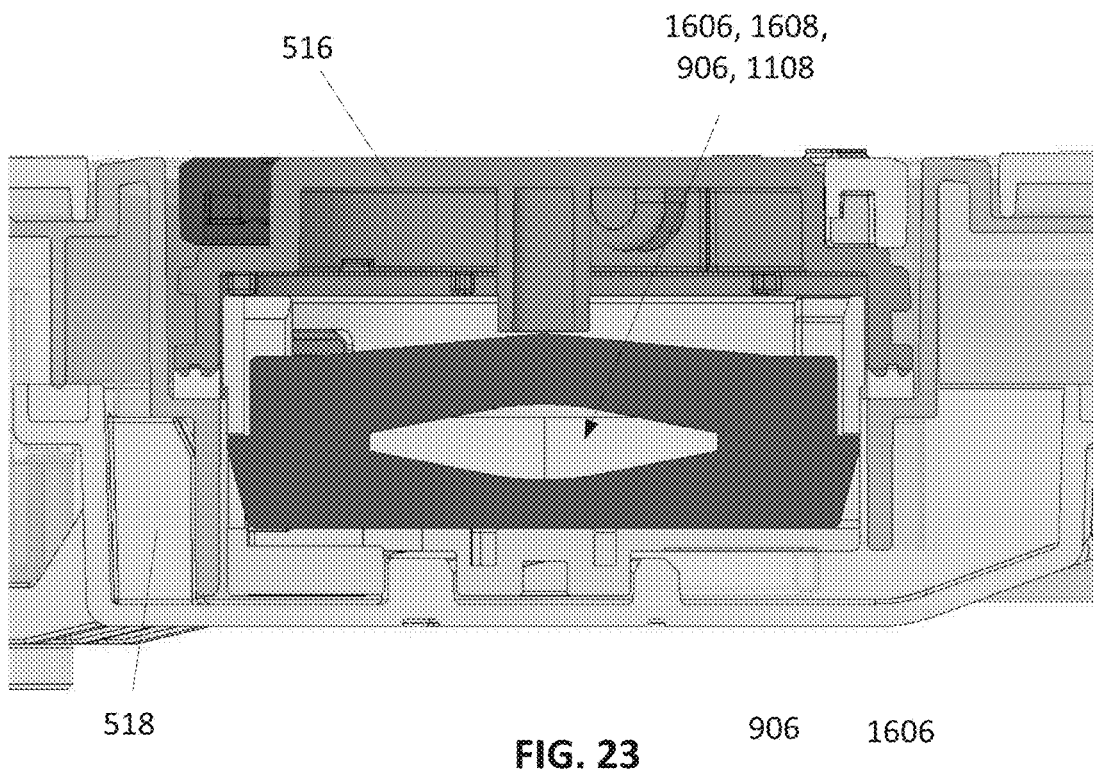
Figure 24:
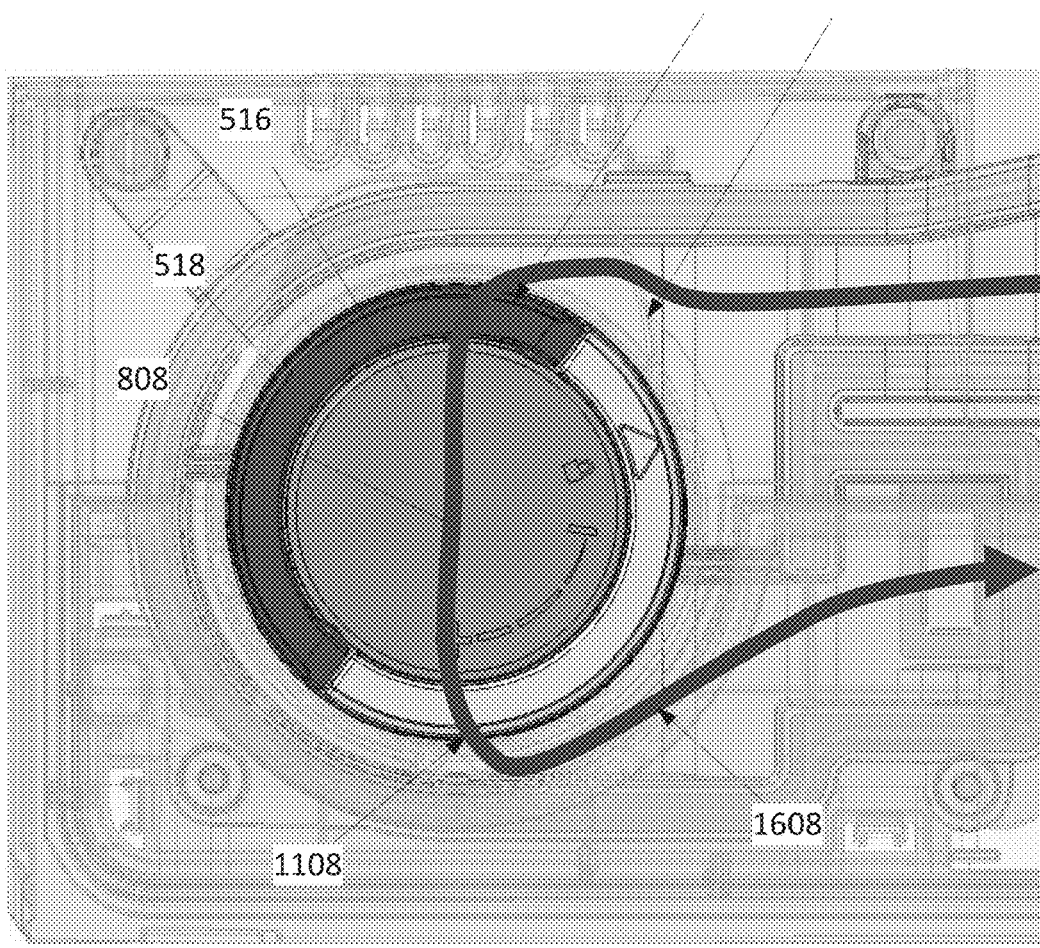

FIGS. 22-33 generally exemplary orientations of the odor dial assembly 516 in various positions, the resulting alignments of the odor inlet 1606 and odor outlet 1608 of the tray 518 relative to the entrance 906 and exit 1108 of the odor dial assembly 516, the resulting alignments of the by-pass inlet 1620 and/or by-pass outlet 1622 of the tray 518 relative to the by-pass entrance 1304 and by-pass exit 1306 of the odor dial assembly 516, as well as the resulting airflow paths. In particular, FIGS. 22-24 generally illustrate the odor dial assembly 516 in the maximum strength position. In the maximum strength position, the by-pass inlet 1620 and/or the by-pass outlet 1622 of the tray 518 are not aligned with the by-pass entrance 1304 and/or by-pass exit 1306 of the odor dial assembly 516 (e.g., the by-pass outlet 1622 is generally sealed by the by-pass sidewall 1302) as generally illustrated in FIG. 22. As such, air by-pass flow path 810 may not flow through the tray 518 and the odor dial assembly 516. In addition, the odor inlet 1606 and odor outlet 1608 of the tray 518 are aligned with the entrance 906 and exit 1108 of the odor dial assembly 516 as generally illustrated in FIG. 23 such that substantially all of the air will flow through the fragrance passageways 808 of the odor dial assembly 516 as generally illustrated in FIG. 24.

Figure 25:
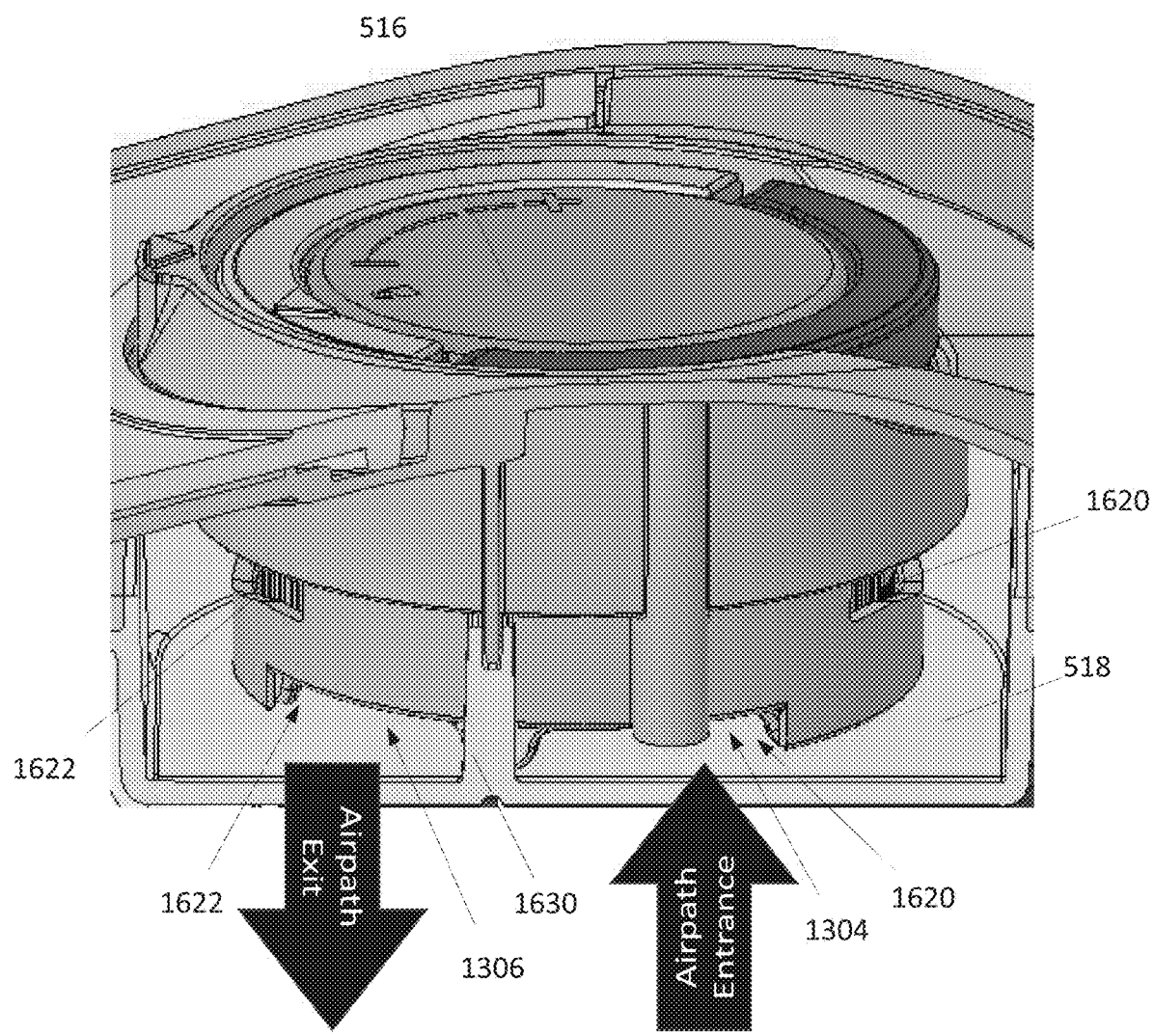
FIGS. 25, 26, and 27 show the odor dial assembly in a minimum strength position consistent with the present disclosure.
Figure 26:
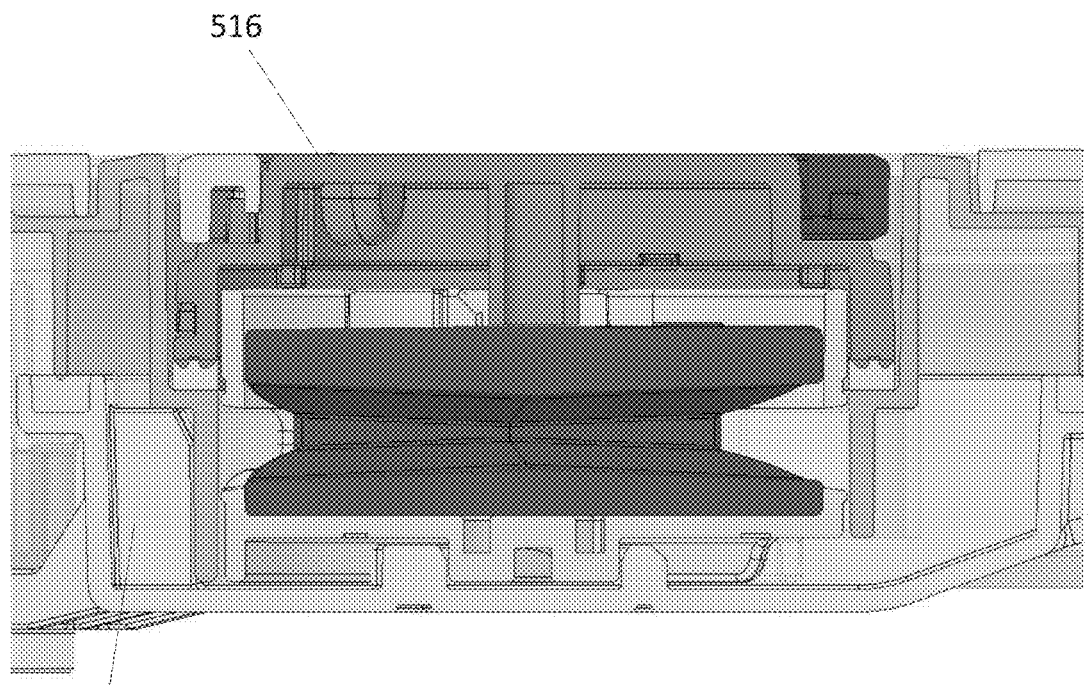
Figure 27:
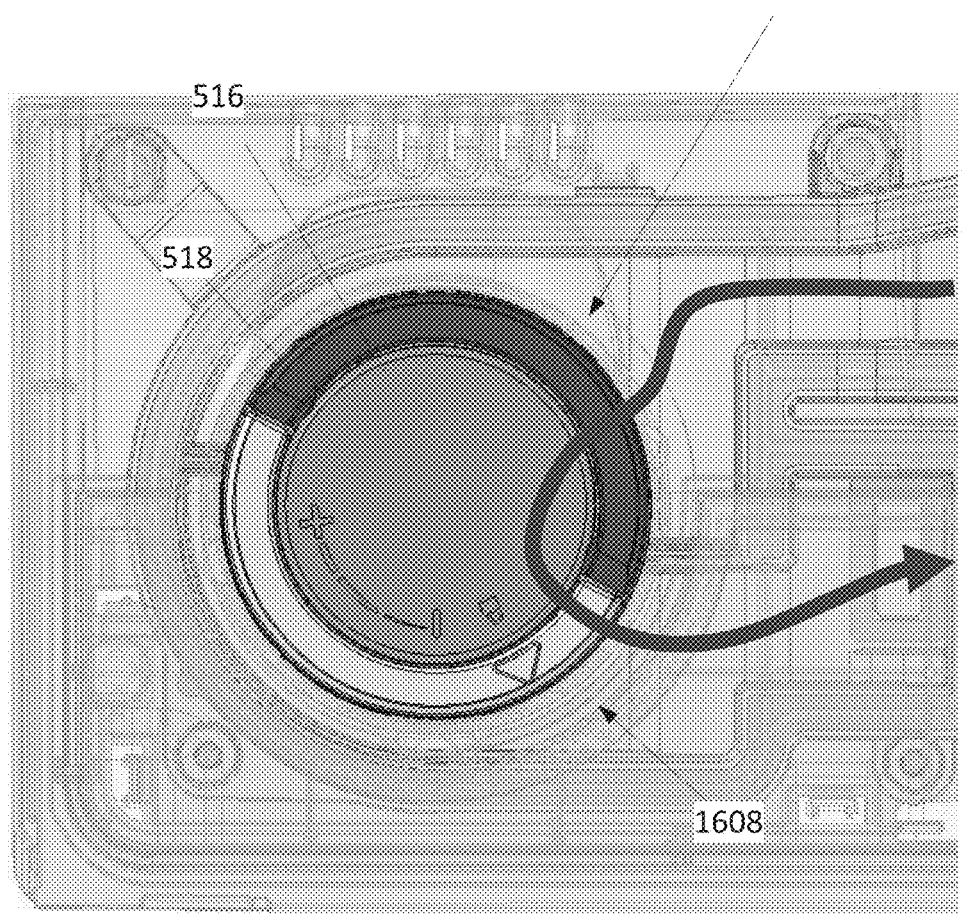

FIGS. 25-27 generally illustrate the odor dial assembly 516 in the minimum strength position. In the minimum strength position, the by-pass inlet 1620 of the tray 518 is aligned with the by-pass entrance 1304 of the odor dial assembly 516 and the by-pass outlet 1622 of the tray 518 is aligned with the by-pass exit 1306 of the odor dial assembly 516 as generally illustrated in FIG. 25. As such, air by-pass flow path 810 may through the tray 518 and the odor dial assembly 516. In addition, the odor inlet 1606 and odor outlet 1608 of the tray 518 may be not aligned with the entrance 906 and exit 1108 of the odor dial assembly 516 as generally illustrated in FIG. 26 such that a minimum or no air will flow through the fragrance passageways 808 of the odor dial assembly 516 as generally illustrated in FIG. 27.

Figure 28:
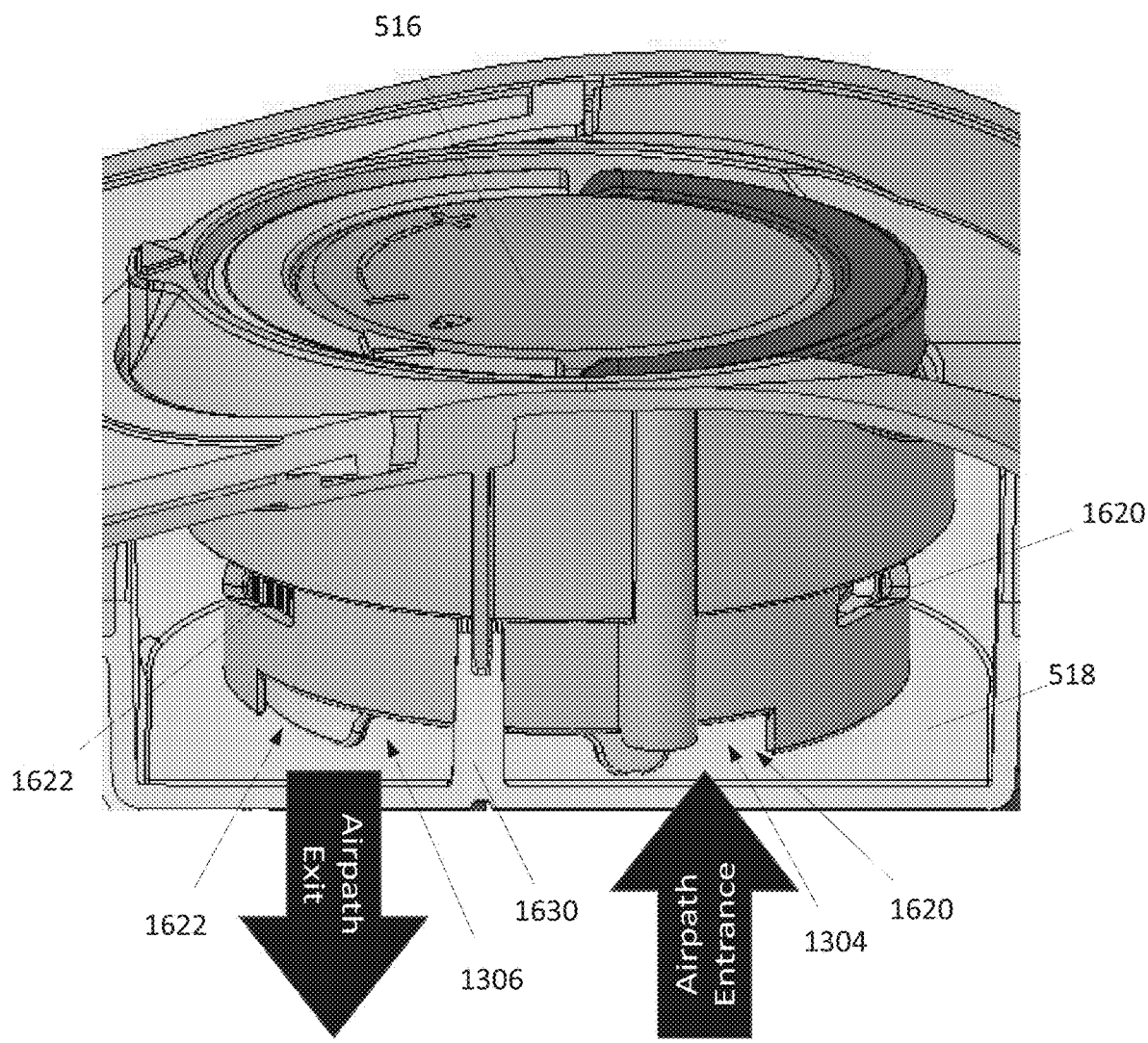
FIGS. 28, 29, and 30 show the odor dial assembly in a first intermediate strength position consistent with the present disclosure.
Figure 29:
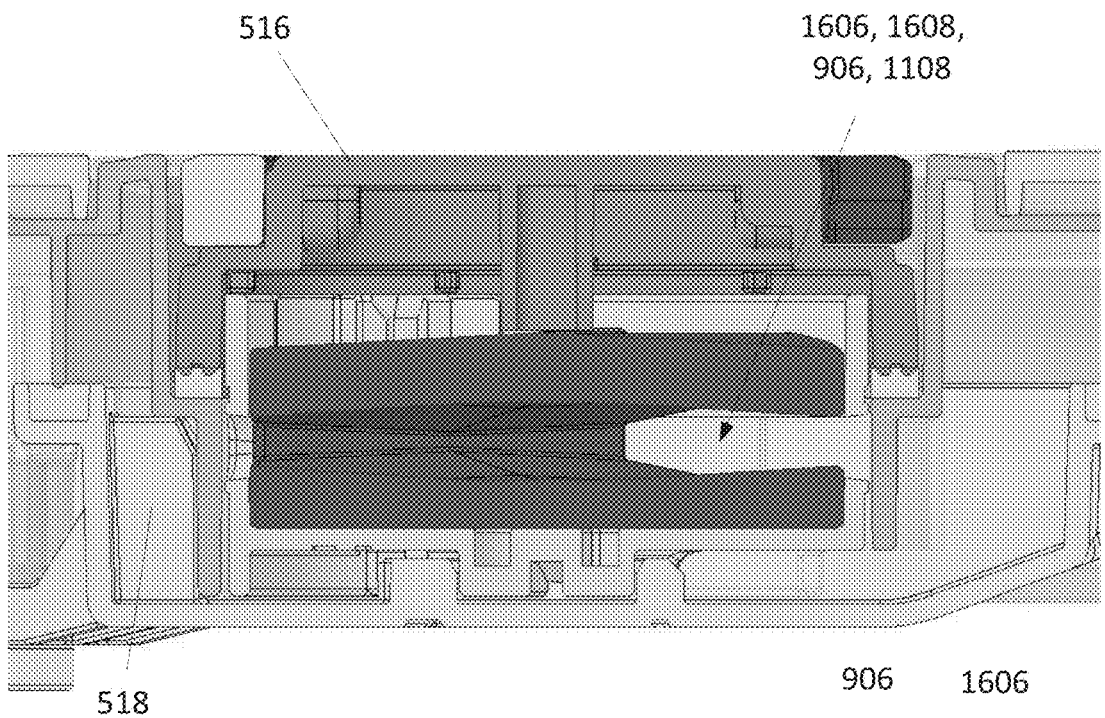
Figure 30:
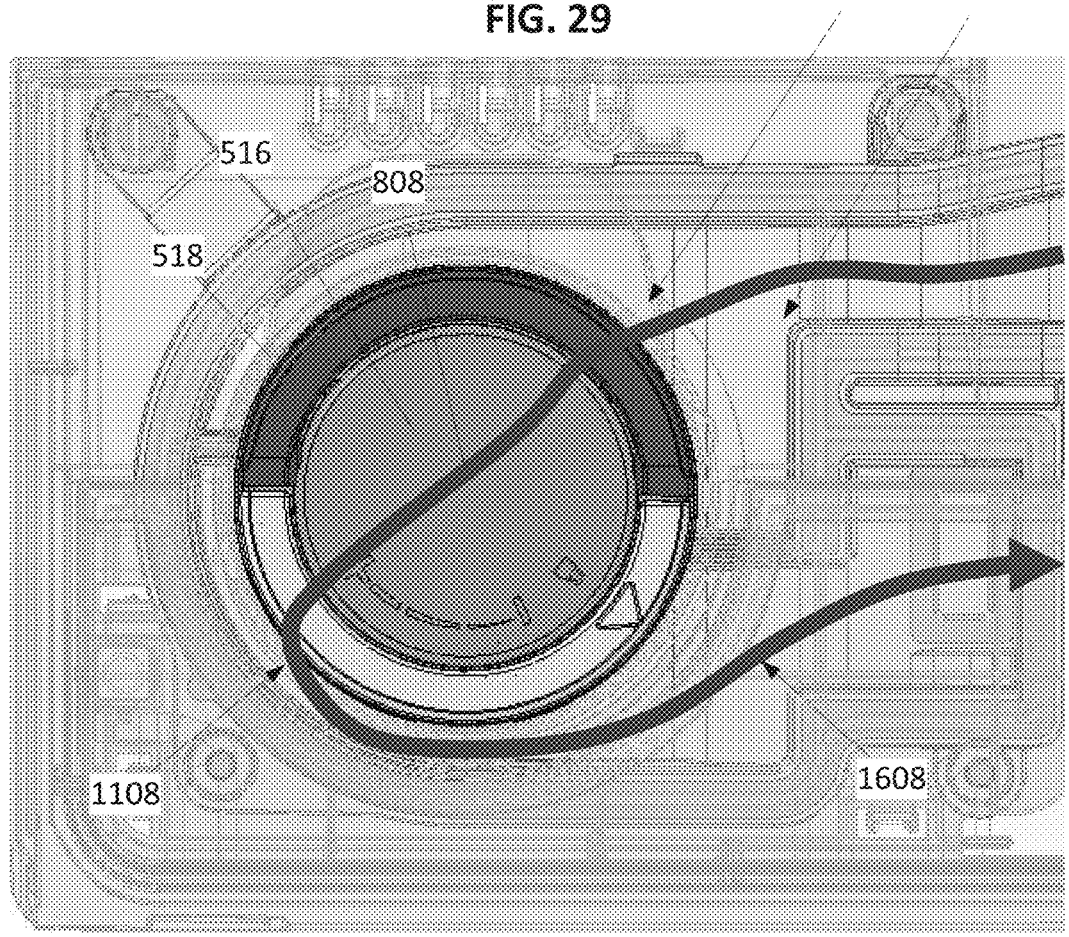

FIGS. 28-30 generally illustrate the odor dial assembly 516 in a first intermediate strength position. In the first intermediate strength position, the by-pass inlet 1620 and the by-pass outlet 1622 of the tray 518 are partially aligned with the by-pass entrance 1304 and by-pass exit 1306 of the odor dial assembly 516 as generally illustrated in FIG. 28. As such, air by-pass flow path 810 may flow through the tray 518 and the odor dial assembly 516. In addition, the odor inlet 1606 and odor outlet 1608 of the tray 518 are partially aligned with the entrance 906 and exit 1108 of the odor dial assembly 516 as generally illustrated in FIG. 29 such that some air will flow through the fragrance passageways 808 of the odor dial assembly 516 as generally illustrated in FIG. 30.

Figure 31:
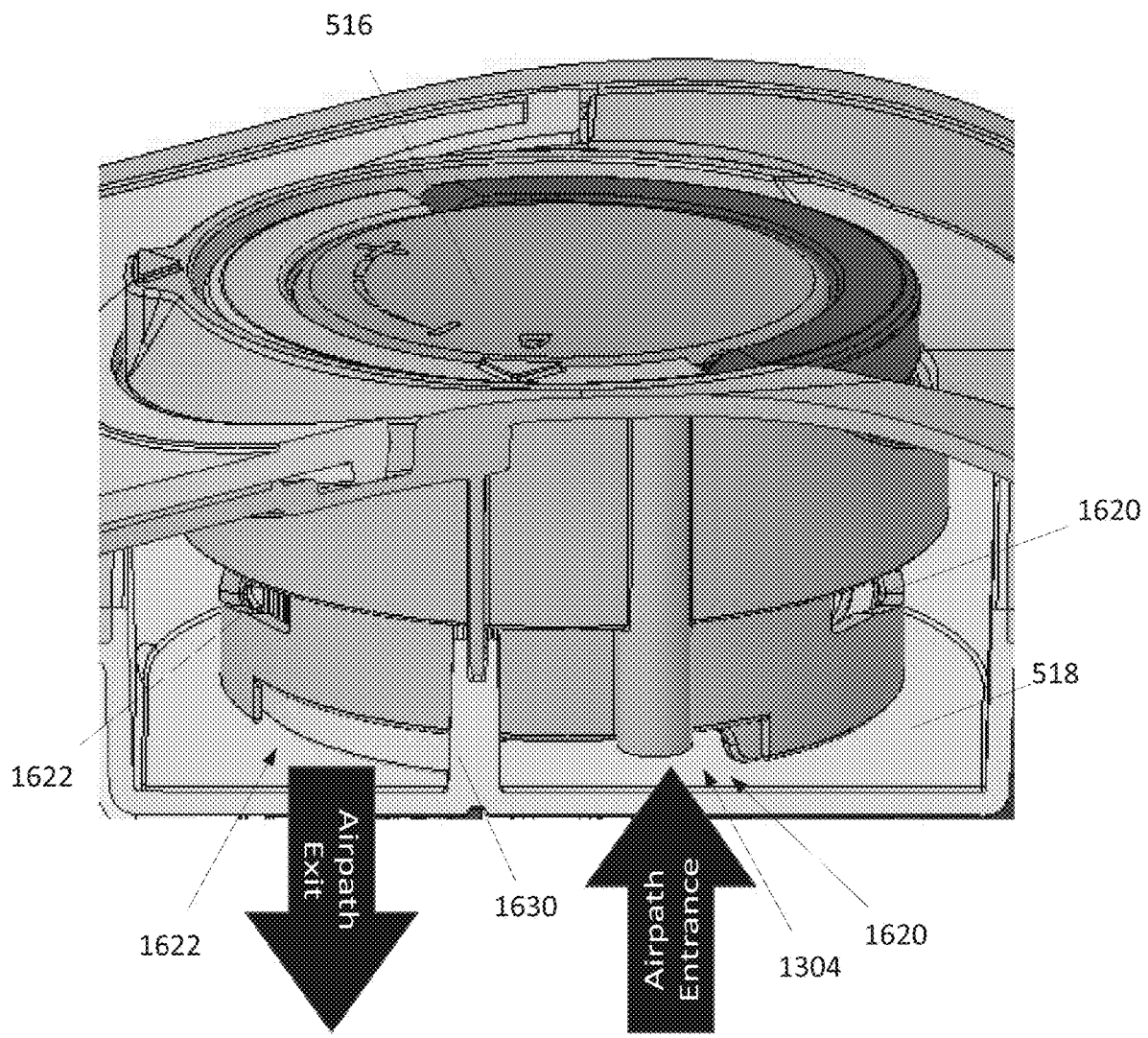
FIGS. 31, 32, and 33 show the odor dial assembly in a second intermediate strength position consistent with the present disclosure.
Figure 32:
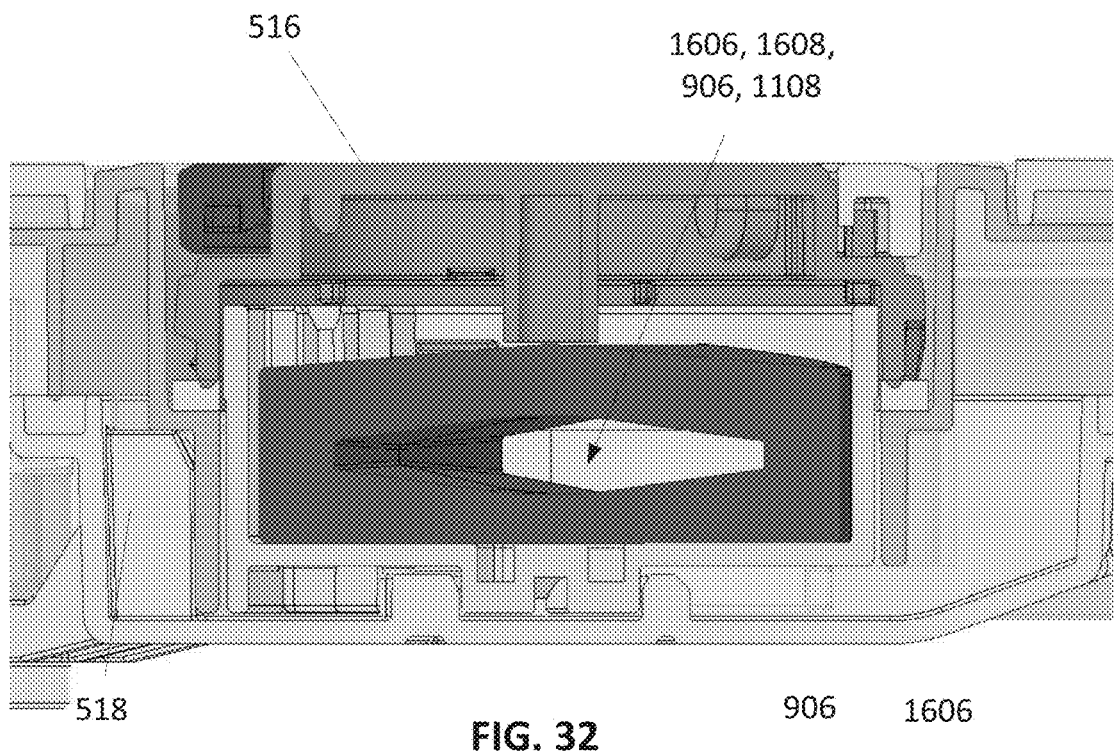
Figure 33:
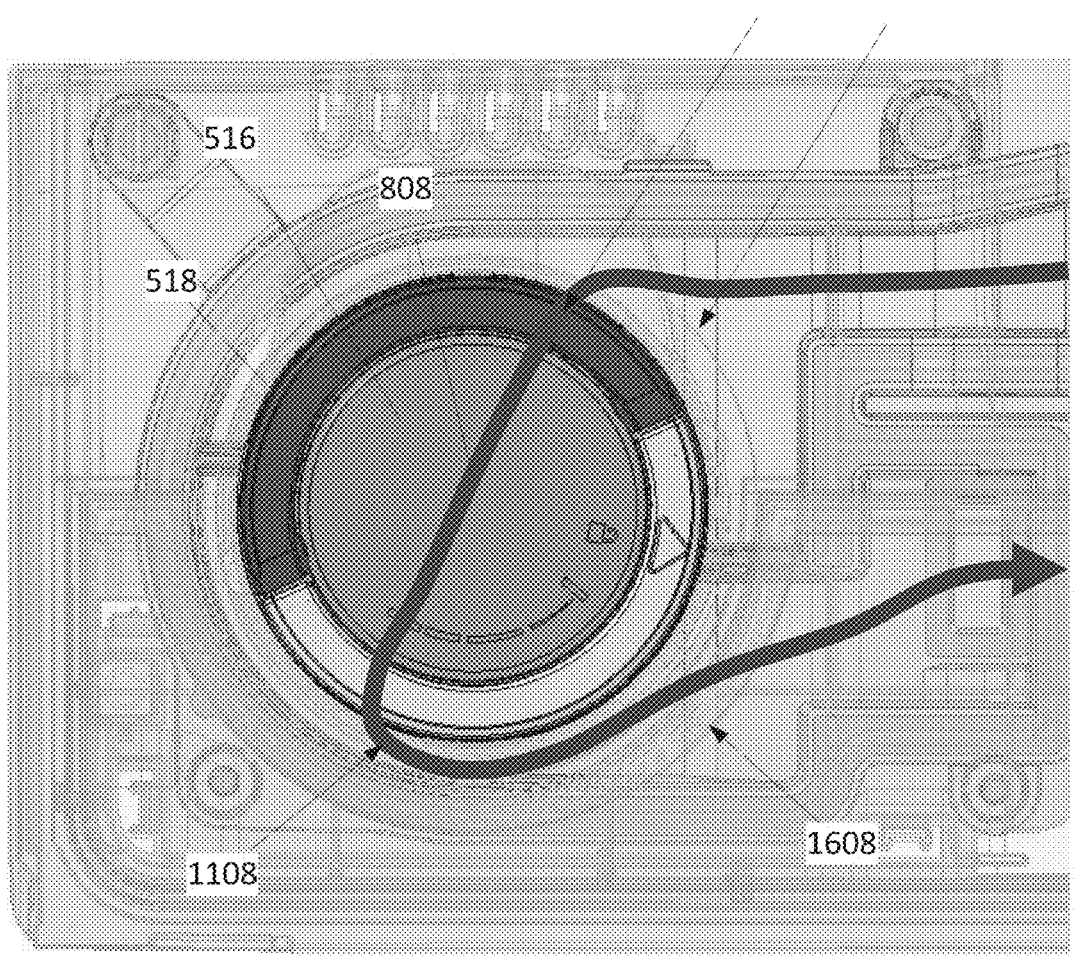

FIGS. 31-33 generally illustrate the odor dial assembly 516 in a second intermediate strength position. In the second intermediate strength position, the by-pass inlet 1620 and/or the by-pass outlet 1622 of the tray 518 are not aligned with the by-pass entrance 1304 and/or by-pass exit 1306 of the odor dial assembly 516 (e.g., the by-pass outlet 1622 is generally sealed by the by-pass sidewall 1302) as generally illustrated in FIG. 31. As such, air by-pass flow path 810 may not flow through the tray 518 and the odor dial assembly 516. In addition, the odor inlet 1606 and odor outlet 1608 of the tray 518 are partially aligned with the entrance 906 and exit 1108 of the odor dial assembly 516 as generally illustrated in FIG. 32 such that some air will flow through the fragrance passageways 808 of the odor dial assembly 516 as generally illustrated in FIG. 33.

It should be appreciated that the surface cleaning devices and the nozzles described herein may include any surface cleaning devices and the nozzles known to those skilled in the art including, but not limited to, upright vacuums, cordless vacuums, stick vacuums, wand vacuums, canister vacuums, robot vacuums, or the like.

While the principles of the disclosure have been described herein, it is to be understood by those skilled in the art that this description is made only by way of example and not as a limitation as to the scope of the disclosure. Other embodiments are contemplated within the scope of the present disclosure in addition to the exemplary embodiments shown and described herein. It will be appreciated by a person skilled in the art that a surface cleaning apparatus may embody any one or more of the features contained herein and that the features may be used in any particular combination or sub-combination. Modifications and substitutions by one of ordinary skill in the art are considered to be within the scope of the present disclosure, which is not to be limited except by the claims.

What is claimed is:

1. A surface cleaning device comprising:
   a nozzle including a nozzle housing and a dirty air passageway; and
   an odor dial assembly including:
      a fragrance member; and
      a dial body configured to be removably coupled to the nozzle housing, the dial body at least partially defining a fragrance cavity configured to at least partially receive the fragrance member and a fragrance passageway extending therethrough;
   wherein the odor dial assembly is configured to transition between a plurality of user-selectable positions to adjust an amount of fragrance particles released by the fragrance member into the dirty air passageway; and
   wherein the nozzle housing includes a tray configured to receive at least a portion of the odor dial assembly, the tray including an odor inlet and an odor outlet, the odor inlet configured to be in fluid communication with atmospheric air, wherein a position of the odor dial assembly relative to the tray defines, at least in part, an amount of air flowing through the fragrance passageway and the fragrance particles released by the fragrance member into the dirty air passageway.

2. The surface cleaning device of claim 1, wherein the fragrance passageway includes an entrance and an exit defined by the dial body, wherein the odor dial assembly is configured to be rotated to adjust and alignment of the entrance and exit relative to the odor inlet and odor outlet to defines, at least in part, the amount of air flowing through the fragrance passageway and the fragrance particles released by the fragrance member into the dirty air passageway.

3. The surface cleaning device of claim 2, wherein at least one of the entrance or the exit of the fragrance passageway defined by the dial body has a width extending between a first and a second end and a height, the height being smaller proximate one or more of the ends of the width than in-between.

4. The surface cleaning device of claim 1, wherein the nozzle housing further includes at least one drive motor and wherein the odor inlet is in fluid communication with atmospheric air which is heated by heat generated by the drive motor.

5. The surface cleaning device of claim 4, wherein the nozzle further includes at least one rotating agitator configured to be rotated by the drive motor.

6. The surface cleaning device of claim 5, wherein the odor dial assembly is configured to be disposed adjacent a first lateral end of the nozzle housing and the drive motor is configured to be disposed adjacent a second lateral end of the nozzle housing.

7. The surface cleaning device of claim 1, wherein the tray further includes a by-pass inlet and a by-pass outlet, the by-pass inlet configured to be in fluid communication with a bypass path, wherein the position of the odor dial assembly relative to the tray defines, at least in part, an amount of by-pass air flowing through the tray which does not flow through the fragrance passageway.

8. The surface cleaning device of claim 7, wherein the dial body further includes a by-pass entrance and a by-pass exit, wherein the odor dial assembly is configured to be rotated to adjust and alignment of the by-pass entrance and the by-pass exit relative to the by-pass inlet and the by-pass outlet to define, at least in part, the amount of by-pass air flowing through the tray which does not flow through the fragrance passageway.

9. The surface cleaning device of claim 8, wherein the dial body includes one or more by-pass sidewalls and one or more divider walls extending downwardly from a base of the dial body, the by-pass sidewalls and the divider walls at least partially defining the by-pass entrance and the by-pass exit.

10. The surface cleaning device of claim 2, wherein the dial body includes a cartridge configured to be removably secured to a cap, the cartridge and the cap configured to define the fragrance cavity configured to at least partially receive the fragrance member.

11. The surface cleaning device of claim 10, wherein the cartridge includes at least one sidewall and at least one base, the at least one sidewall defining the entrance and the exit of the fragrance passageway.

12. The surface cleaning device of claim 11, wherein the cartridge and the tray include a detent lever and a cam having a plurality of detent grooves, wherein the detent lever is configured to engage the plurality detent grooves to align the odor dial assembly in a selected one of a plurality of predefined positions relative to the tray, wherein the predefined positions correspond to different amounts of fragrance particles being released by the fragrance member into the dirty air passageway.

13. The surface cleaning device of claim 12, wherein the plurality of predefined positions includes at least a first open position to release a first predetermined amount of fragrance from the fragrance member into the dirty air passageway and a closed position to substantially prevent fragrance from the fragrance member being released into the dirty air passageway.

14. A surface cleaning device comprising:
a nozzle including a nozzle housing and a dirty air passageway; and
an odor dial assembly including:
a fragrance member; and
a dial body configured to be removably coupled to the nozzle housing, the dial body at least partially defining a fragrance cavity configured to at least partially receive the fragrance member and a fragrance passageway extending therethrough, wherein the dial body further includes a handle;
wherein the odor dial assembly is configured to transition between a plurality of user-selectable positions to adjust an amount of fragrance particles released by the fragrance member into the dirty air passageway.

15. The surface cleaning device of claim 14, wherein the handle is hingedly coupled to the dial body.

16. The surface cleaning device of claim 1, wherein both the odor dial assembly and the nozzle includes indicia representative of the amount of fragrance particles released by the fragrance member into the dirty air passageway.

17. A surface cleaning device comprising:
an odor dial assembly including:
a fragrance member; and
a dial body comprising:
a cartridge configured to be removably secured to a cap, the cartridge and the cap configured to define a fragrance cavity configured to at least partially receive the fragrance member; and
a fragrance passageway extending through the dial body, the dial body defining an entrance and an exit of the fragrance passageway;
wherein the odor dial assembly is configured to be removably coupled to a nozzle and to transition between a plurality of user-selectable positions to adjust an amount of fragrance particles released by the fragrance member into a dirty air passageway; and
wherein the dial body includes one or more by-pass sidewalls and one or more divider walls extending downwardly from a base of the dial body, the by-pass sidewalls and the divider walls at least partially defining a by-pass entrance and a by-pass exit.

18. A surface cleaning device comprising:
an odor dial assembly including:
a fragrance member; and
a dial body comprising:
a cartridge configured to be removably secured to a cap, the cartridge and the cap configured to define a fragrance cavity configured to at least partially receive the fragrance member; and
a fragrance passageway extending through the dial body, the dial body defining an entrance and an exit of the fragrance passageway;
wherein the odor dial assembly is configured to be removably coupled to a nozzle and to transition between a plurality of user-selectable positions to adjust an amount of fragrance particles released by the fragrance member into a dirty air passageway; and
wherein the fragrance member includes a through hole aligned with the entrance and the exit of the fragrance passageway.

19. The surface cleaning device of claim 17, further comprising the cap.

20. The surface cleaning device of claim 17, wherein the fragrance member includes at least one of Ethylene-vinyl Acetate, Thermoplastic Polyurethane, and/or Polyolefin.

21. The surface cleaning device of claim 18, further comprising the cap.

22. The surface cleaning device of claim 18, wherein the fragrance member includes at least one of Ethylene-vinyl Acetate, Thermoplastic Polyurethane, and/or Polyolefin.

* * * * *